(12) United States Patent
Kwak et al.

(10) Patent No.: US 6,562,347 B1
(45) Date of Patent: May 13, 2003

(54) CHEMOKINE-TUMOR ANTIGEN FUSION PROTEINS AS CANCER VACCINES

(75) Inventors: Larry W. Kwak, Frederick, MD (US); Arya Biragyn, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/646,028

(22) PCT Filed: Mar. 12, 1999

(86) PCT No.: PCT/US99/05345

§ 371 (c)(1),
(2), (4) Date: Sep. 12, 2000

(87) PCT Pub. No.: WO99/46392

PCT Pub. Date: Sep. 16, 1999

Related U.S. Application Data

(60) Provisional application No. 60/077,745, filed on Mar. 12, 1998.

(51) Int. Cl.⁷ .................. A61K 38/19; A61K 39/00; C07K 14/52; C07K 19/00
(52) U.S. Cl. ............... 424/192.1; 424/85.1; 424/184.1; 424/185.1; 424/277.1; 424/278.1; 530/350; 530/351; 530/395; 530/806; 514/1; 514/2; 514/8; 514/885
(58) Field of Search ................ 530/350, 351, 530/395, 806; 424/85.1, 184.1, 185.1, 192.1, 277.1, 278.1; 514/1, 2, 8, 885

(56) References Cited

U.S. PATENT DOCUMENTS 5,989,552 A * 11/1999 McKenzie et al.

6,001,649 A * 12/1999 Caput et al.

FOREIGN PATENT DOCUMENTS

| EP | 0 706 799 A2 | 4/1996 |
| WO | WO 97/35008 | 9/1997 |
| WO | WO 98/01564 | 1/1998 |

OTHER PUBLICATIONS

Boon Adv. Cancer Res. 1992; 58:177–210.*
Hellstrom et al. Immunol. Rev. 1995; 145:123–145.*
Biragyn et al. "E. Coli Expressed Lymphoma IG Idiotype Antigen Fusion Proteins and Chimeric HBcAG Particles Bearing Tumor Epitopes" *Cancer Biotherapy* 10(1):85 (Mar. 3, 1995).
Kwak et al. "Idiotypes as Vaccines for the Treatment of B–Cell Malignancies" *Immunotechnology* 2(4):268 (Nov. 1, 1996).
Cocchi et al. "The V3 Domain of the HIV–1 gp120 Envelope Glycoprotein Is Critical for Chemokine–Mediated Blockade of Infection" *Nature Medicine* 2(11):1244–7 (Nov. 1996).
Biragyn et al. "Genetic Fusion of Chemokines to a Self Tumor Antigen Induces Protective, T–Cell Dependent Antitumor Immunity" *Nature Biotechnology* 17(3):253–8 (Mar., 1999).

* cited by examiner

Primary Examiner—Phillip Gambel
Assistant Examiner—Jessica H. Roark
(74) Attorney, Agent, or Firm—Needle & Rosenberg, PC.

(57) ABSTRACT

The present invention provides a fusion polypeptide comprising a chemokine and either a tumor or viral antigen which is administered as either a protein or nucleic acid vaccine to elicit an immune response effective in treating cancer or effective in treating or preventing HIV infection.

4 Claims, No Drawings

SEQUENCE LISTING

<160> NUMBER OF SEQ ID NOS: 57

<210> SEQ ID NO 1
<211> LENGTH: 134
<212> TYPE: PRT
<213> ORGANISM: Artificial Sequence
<220> FEATURE:
<223> OTHER INFORMATION: Description of artificial sequence:
       /note=synthetic construct

<400> SEQUENCE: 1

```
Met Val Pro Leu Ser Arg Thr Val Arg Cys Thr Cys Ile Ser Ile Ser
 1               5                  10                  15
Asn Gln Pro Val Asn Pro Arg Ser Leu Glu Lys Leu Glu Ile Pro Ala
                20                  25                  30
Ser Gln Phe Cys Pro Arg Val Glu Ile Ile Ala Thr Met Lys Lys Lys
            35                  40                  45
Gly Glu Lys Arg Cys Leu Asn Pro Glu Ser Lys Ala Ile Lys Asn Leu
        50                  55                  60
Leu Lys Ala Val Ser Lys Glu Met Ser Lys Arg Ser Glu Phe Asn Asp
 65                  70                  75                  80
Ala Gln Ala Pro Lys Ser Leu Asp Gly Val Thr Ser Ala Pro Asp Thr
                85                  90                  95
Arg Pro Ala Pro Gly Ser Thr Ala Pro Pro Ala His Ala Asn Ser Pro
            100                 105                 110
Asp Thr Arg Pro Ala Pro Gly Ser Thr Pro Pro Ala His Gly Val
        115                 120                 125
Thr Ser Ala Ala Leu Glu
        130
```

<210> SEQ ID NO 2
<211> LENGTH: 137
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 2

```
Met Ala Gln Pro Val Gly Ile Asn Thr Ser Thr Thr Cys Cys Tyr Arg
 1               5                  10                  15
Phe Ile Asn Lys Lys Ile Pro Lys Gln Arg Leu Glu Ser Tyr Arg Arg
                20                  25                  30
Thr Thr Ser Ser His Cys Pro Arg Glu Ala Val Ile Phe Lys Thr Lys
            35                  40                  45
Leu Asp Lys Glu Ile Cys Ala Asp Pro Thr Gln Lys Trp Val Gln Asp
        50                  55                  60
Phe Met Lys His Leu Asp Lys Lys Thr Gln Thr Pro Lys Leu Glu Phe
 65                  70                  75                  80
Asn Asp Ala Gln Ala Pro Lys Ser Leu Glu Asp Gly Val Thr Ser Ala
                85                  90                  95
Pro Asp Thr Arg Pro Ala Pro Gly Ser Thr Ala Pro Ala His Ala
            100                 105                 110
Asn Ser Pro Asp Thr Arg Pro Ala Pro Gly Ser Thr Pro Pro Ala
        115                 120                 125
His Gly Val Thr Ser Ala Ala Leu Glu
        130                 135
```

<210> SEQ ID NO 3
<211> LENGTH: 138
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 3

```
Met Ala Ile Pro Leu Ala Arg Thr Val Arg Cys Asn Cys Ile His Ile
1               5                   10                  15

Asp Asp Gly Pro Val Arg Met Arg Ala Ile Gly Lys Leu Glu Ile Ile
            20                  25                  30

Pro Ala Ser Leu Ser Cys Pro Arg Val Glu Ile Ile Ala Thr Met Lys
        35                  40                  45

Lys Asn Asp Glu Gln Arg Cys Leu Asn Pro Ser Lys Thr Ile Lys
50                  55                  60

Asn Leu Met Lys Ala Phe Ser Gln Lys Arg Ser Lys Arg Ala Pro Glu
65                  70                  75                  80

Phe Asn Asp Ala Gln Ala Pro Lys Ser Leu Glu Asp Gly Val Thr Ser
                85                  90                  95

Ala Pro Asp Thr Arg Pro Ala Pro Gly Ser Thr Ala Pro Ala His
                100                 105                 110

Ala Asn Ser Pro Asp Thr Arg Pro Ala Pro Gly Ser Thr Pro Pro Pro
            115                 120                 125

Ala His Gly Val Thr Ser Ala Ala Leu Glu
            130                 135
```

```
<210> SEQ ID NO 4
<211> LENGTH: 156
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 4
```

```
Met Arg Ile Ser Ala Thr Leu Leu Cys Leu Leu Leu Ile Ala Ala Ala
1               5                   10                  15

Phe Ser Ile Gln Val Trp Ala Gln Pro Asp Gly Pro Asn Ala Ser Thr
            20                  25                  30

Cys Cys Tyr Val Lys Lys Gln Lys Ile Pro Lys Arg Asn Leu Lys Ser
        35                  40                  45

Tyr Arg Arg Ile Thr Ser Ser Arg Cys Pro Trp Glu Ala Val Ile Phe
    50                  55                  60

Lys Thr Lys Lys Gly Met Glu Val Cys Ala Glu Ala His Gln Lys Trp
65                  70                  75                  80

Val Glu Glu Ala Ile Ala Tyr Leu Asp Met Lys Thr Pro Thr Pro Lys
                85                  90                  95

Pro Glu Phe Asn Asp Ala Gln Ala Pro Lys Ser Leu Glu Asp Gly Val
            100                 105                 110

Thr Ser Ala Pro Asp Thr Arg Pro Ala Pro Gly Ser Thr Ala Pro Pro
        115                 120                 125

Ala His Ala Asn Ser Pro Asp Thr Arg Pro Ala Pro Gly Ser Thr Pro
    130                 135                 140

Pro Pro Ala His Gly Val Thr Ser Ala Ala Leu Glu
145                 150                 155
```

```
<210> SEQ ID NO 5
<211> LENGTH: 166
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 5
```

-continued

```
Met Asn Ala Lys Val Val Val Leu Val Leu Val Thr Ala Leu
 1               5                  10                  15

Cys Leu Ser Asp Gly Lys Pro Val Ser Leu Ser Tyr Arg Cys Pro Cys
                 20                  25                  30

Arg Phe Phe Glu Ser His Val Ala Arg Ala Asn Val Lys His Leu Lys
                 35                  40                  45

Ile Leu Asn Thr Pro Asn Cys Ala Leu Gln Ile Val Ala Arg Leu Lys
         50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys Arg Phe Lys Met Glu Phe Asn
                 85                  90                  95

Asp Ala Gln Ala Pro Lys Ser Leu Glu Asn Cys Thr Arg Pro Asn Asn
                100                 105                 110

Asn Thr Arg Lys Arg Ile Arg Ile Gln Arg Gly Pro Gly Arg Ala Phe
                115                 120                 125

Val Thr Ile Gly Lys Ile Gly Asn Met Arg Gln Ala His Cys Asn Ile
        130                 135                 140

Ser Gly Ser Ala Glu Glu Gln Lys Leu Ile Ser Glu Glu Asp Leu Ala
145                 150                 155                 160

His His His His His His
                165

<210> SEQ ID NO 6
<211> LENGTH: 149
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 6

Met Val Pro Leu Ser Arg Thr Val Arg Cys Thr Cys Ser Ile Ser Asn
 1               5                  10                  15

Gln Pro Val Asn Pro Arg Ser Leu Glu Lys Leu Glu Ile Ile Pro Ala
                 20                  25                  30

Ser Gln Phe Cys Pro Arg Val Glu Ile Ile Ala Thr Met Lys Lys Lys
                 35                  40                  45

Gly Glu Lys Arg Cys Leu Asn Pro Glu Ser Lys Ala Ile Lys Asn Leu
         50                  55                  60

Leu Lys Ala Val Ser Lys Glu Met Ser Lys Arg Ser Glu Phe Asn Asp
 65                  70                  75                  80

Ala Gln Ala Pro Lys Ser Leu Glu Asn Cys Thr Arg Pro Asn Asn Asn
                 85                  90                  95

Thr Arg Lys Arg Ile Arg Ile Gln Arg Gly Pro Gly Arg Ala Phe Val
                100                 105                 110

Thr Ile Gly Lys Ile Gly Asn Met Arg Gln Ala His Cys Asn Ile Ser
        115                 120                 125

Gly Ser Ala Glu Glu Gln Lys Leu Ile Ser Glu Glu Asp Leu Ala His
        130                 135                 140

His His His His His
145

<210> SEQ ID NO 7
<211> LENGTH: 151
<212> TYPE: PRT
<213> ORGANISM: Artificial Sequence
```

```
<220> FEATURE:
<223> OTHER INFORMATION: Description of artificial sequence:
      /note=synthetic construct

<400> SEQUENCE: 7

Met Ala Gln Pro Val Gly Ile Asn Thr Ser Thr Thr Cys Cys Tyr Arg
1               5                   10                  15

Phe Ile Asn Lys Lys Ile Pro Lys Gln Arg Leu Glu Ser Tyr Arg Arg
                20                  25                  30

Thr Thr Ser Ser His Cys Pro Arg Glu Ala Val Ile Phe Lys Thr Lys
            35                  40                  45

Leu Asp Lys Glu Ile Cys Ala Asp Pro Thr Gln Lys Trp Val Gln Asp
    50                  55                  60

Phe Met Lys His Leu Asp Lys Lys Thr Gln Thr Pro Lys Leu Glu Phe
65                  70                  75                  80

Asn Asp Ala Gln Ala Pro Lys Ser Leu Glu Asn Cys Thr Arg Pro Asn
                85                  90                  95

Asn Asn Thr Arg Lys Arg Ile Arg Ile Gln Arg Gly Pro Gly Arg Ala
                100                 105                 110

Phe Val Thr Ile Gly Lys Ile Gly Asn Met Arg Gln Ala His Cys Asn
            115                 120                 125

Ile Ser Gly Ser Ala Glu Glu Gln Lys Leu Ile Ser Glu Glu Asp Leu
    130                 135                 140

Ala His His His His His
145                 150

<210> SEQ ID NO 8
<211> LENGTH: 152
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 8

Met Ala Ile Pro Leu Ala Arg Thr Val Arg Cys Asn Cys Ile His Ile
1               5                   10                  15

Asp Asp Gly Pro Val Arg Met Arg Ala Ile Gly Lys Leu Glu Ile Ile
                20                  25                  30

Pro Ala Ser Leu Ser Cys Pro Arg Val Glu Ile Ile Ala Thr Met Lys
            35                  40                  45

Lys Asn Asp Glu Gln Arg Cys Leu Asn Pro Glu Ser Lys Thr Ile Lys
    50                  55                  60

Asn Leu Met Lys Ala Phe Ser Gln Lys Arg Ser Lys Arg Ala Pro Glu
65                  70                  75                  80

Phe Asn Asp Ala Gln Ala Pro Lys Ser Leu Glu Asn Cys Thr Arg Pro
                85                  90                  95

Asn Asn Asn Thr Arg Lys Arg Ile Arg Ile Gln Arg Gly Pro Gly Arg
                100                 105                 110

Ala Phe Val Thr Ile Gly Lys Ile Gly Asn Met Arg Gln Ala His Cys
            115                 120                 125

Asn Ile Ser Gly Ser Ala Glu Glu Gln Lys Leu Ile Ser Glu Glu Asp
    130                 135                 140

Leu Ala His His His His His
145                 150

<210> SEQ ID NO 9
```

```
<211> LENGTH: 171
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 9

Met Arg Ile Ser Ala Thr Leu Leu Cys Leu Leu Leu Ile Ala Ala Ala
 1               5                  10                  15

Phe Ser Ile Gln Val Trp Ala Gln Pro Asp Gly Pro Asn Ala Ser Thr
            20                  25                  30

Cys Cys Tyr Val Lys Lys Gln Lys Ile Pro Lys Arg Asn Leu Lys Ser
        35                  40                  45

Tyr Arg Arg Ile Thr Ser Ser Arg Cys Pro Arg Trp Glu Ala Val Ile
 50                  55                  60

Phe Lys Thr Lys Lys Gly Met Glu Val Cys Ala Glu Ala His Gln Lys
 65                  70                  75                  80

Trp Val Glu Glu Ala Ile Ala Tyr Leu Asp Met Lys Thr Pro Thr Pro
                85                  90                  95

Lys Pro Glu Phe Asn Asp Ala Gln Ala Pro Lys Ser Leu Glu Asn Cys
            100                 105                 110

Thr Arg Pro Asn Asn Asn Thr Arg Lys Arg Ile Arg Ile Gln Arg Gly
        115                 120                 125

Pro Gly Pro Ala Phe Val Thr Ile Gly Lys Ile Gly Asn Met Arg Gln
130                 135                 140

Ala His Cys Asn Ile Ser Gly Ser Ala Glu Glu Gln Lys Leu Ile Ser
145                 150                 155                 160

Glu Glu Asp Leu Ala His His His His His His
                165                 170

<210> SEQ ID NO 10
<211> LENGTH: 40
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 10

Asn Cys Thr Arg Pro Asn Asn Asn Thr Arg Lys Arg Ile Arg Ile Gln
 1               5                  10                  15

Arg Gly Pro Gly Arg Ala Phe Val Thr Ile Gly Lys Ile Gly Asn Met
            20                  25                  30

Arg Gln Ala His Cys Asn Ile Ser
        35                  40

<210> SEQ ID NO 11
<211> LENGTH: 11
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 11

Glu Phe Asn Asp Gln Ala Pro Lys Ser Leu Glu
 1               5                  10

<210> SEQ ID NO 12
<211> LENGTH: 348
```

```
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 12

Met Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Met Ser Lys Arg Ser Met Gly Leu
65                  70                  75                  80

Glu Ala Glu Glu Gln Lys Leu Ile Ser Glu Asp Leu Pro Ser Asp
                85                  90                  95

Val Glu Val Gln Leu Gln Gln Ser Gly Pro Asp Leu Val Lys Pro Gly
            100                 105                 110

Met Ser Val Lys Leu Ser Cys Lys Thr Leu Gly Tyr Asn Phe Ser Asp
        115                 120                 125

Lys Arg Ile His Trp Ile Lys Gln Lys Pro Gly Arg Gly Leu Glu Trp
    130                 135                 140

Val Gly Arg Ile Asp Pro Ser Asn Gly Asp Thr Asp Tyr Asn Ala Asp
145                 150                 155                 160

Phe Lys Thr Pro Ala Thr Leu Thr Val Asp Arg Pro Ser Asn Thr Ala
                165                 170                 175

Tyr Leu Glu Leu Ser Asn Leu Thr Ser Gly Asp Ser Ala Val Tyr Tyr
            180                 185                 190

Cys Ser Ile Ser Gly Asp Tyr Ser Ala Cys Asp Tyr Trp Gly Gln Gly
        195                 200                 205

Thr Glu Leu Thr Val Ser Ser Gly Gly Gly Gly Ser Gly Gly Gly Gly
    210                 215                 220

Ser Gly Gly Gly Gly Ser Asp Val Val Met Thr Gln Thr Pro Leu Ser
225                 230                 235                 240

Leu Ala Val Ser Leu Gly Asp His Val Lys Met Ser Cys Arg Cys Asn
                245                 250                 255

Gln Ser Leu Val Asn Ser His Gly Asp Ser Phe Leu His Trp Phe Leu
            260                 265                 270

Gln Lys Pro Gly Gln Ser Pro Lys Leu Leu Ile Tyr Lys Val Ser Ser
        275                 280                 285

Arg Phe Phe Gly Val Pro Glu Arg Phe Ser Gly Ser Gly Ser Gly Thr
    290                 295                 300

Asp Phe Thr Leu Glu Ile Ser Arg Val Glu Ala Glu Asp Leu Gly Val
305                 310                 315                 320

Tyr Phe Cys Ser Gln Gly Ala His Val Pro Trp Thr Phe Gly Gly Gly
                325                 330                 335

Thr Lys Leu Glu Val Lys His His His His His His
            340                 345

<210> SEQ ID NO 13
<211> LENGTH: 361
<212> TYPE: PRT
<213> ORGANISM: Artificial Sequence
```

```
<220> FEATURE:
<223> OTHER INFORMATION: Description of artificial sequence:
      /note=synthetic construct

<400> SEQUENCE: 13

Met Val Pro Leu Ser Arg Thr Val Arg Cys Thr Cys Ile Ser Ile Ser
 1               5                  10                  15

Asn Gln Pro Val Asn Pro Arg Ser Leu Glu Lys Leu Glu Ile Ile Pro
             20                  25                  30

Ala Ser Gln Phe Cys Pro Arg Val Glu Ile Ile Ala Thr Met Lys Lys
         35                  40                  45

Lys Gly Glu Lys Arg Cys Leu Asn Pro Glu Ser Lys Ala Ile Lys Asn
 50                  55                  60

Leu Leu Lys Ala Val Ser Lys Glu Met Ser Lys Arg Ser Ala Arg Lys
 65                  70                  75                  80

Leu Asn Asp Ala Gln Ala Pro Lys Ser Asp Leu Glu Val Lys Leu Val
                 85                  90                  95

Glu Ser Gly Gly Gly Leu Val Gln Pro Gly Gly Ser Leu Ser Leu Ser
            100                 105                 110

Cys Ala Ala Ser Gly Phe Thr Phe Thr Asp Tyr Tyr Met Ser Trp Val
        115                 120                 125

Arg Gln Pro Pro Gly Lys Ala Leu Glu Trp Leu Ala Leu Ile Arg Asn
130                 135                 140

Lys Ala Asn Gly Tyr Thr Thr Glu Tyr Ser Ala Ser Val Lys Gly Arg
145                 150                 155                 160

Phe Thr Ile Ser Arg Asp Asn Ser Gln Ser Ile Leu Tyr Leu Gln Met
                165                 170                 175

Asn Ala Leu Arg Ala Glu Asp Ser Ala Thr Tyr Tyr Cys Ala Arg Asp
            180                 185                 190

Pro Asn Tyr Tyr Asp Gly Ser Tyr Glu Gly Tyr Phe Asp Tyr Trp Ala
        195                 200                 205

Gln Gly Thr Thr Leu Thr Val Ser Ser Gly Gly Gly Ser Gly Gly
    210                 215                 220

Gly Gly Ser Gly Gly Gly Ser Gly Ser Asp Ile Gln Met Thr Gln
225                 230                 235                 240

Ser Pro Ser Ser Leu Ser Ala Ser Leu Gly Gly Lys Val Thr Ile Thr
                245                 250                 255

Cys Lys Ala Ser Gln Asp Ile Asn Lys Tyr Ile Ala Trp Tyr Gln His
            260                 265                 270

Lys Pro Gly Lys Gly Pro Arg Leu Leu Ile His Tyr Thr Ser Thr Leu
        275                 280                 285

Gln Pro Gly Ile Pro Ser Arg Phe Ser Gly Ser Gly Ser Gly Arg Asp
    290                 295                 300

Tyr Ser Phe Ser Ile Ser Asn Leu Glu Pro Glu Asp Ile Ala Thr Tyr
305                 310                 315                 320

Tyr Cys Leu Gln Tyr Asp Asn Leu Tyr Thr Phe Gly Gly Gly Thr Lys
                325                 330                 335

Leu Glu Ile Lys Gly Ser Ala Glu Glu Gln Lys Leu Ile Ser Glu Glu
            340                 345                 350

Asp Leu Ala His His His His His His
        355                 360

<210> SEQ ID NO 14
<211> LENGTH: 361
<212> TYPE: PRT
```

<213> ORGANISM: Artificial Sequence
<220> FEATURE:
<223> OTHER INFORMATION: Description of artificial sequence:
      /note=synthetic construct

<400> SEQUENCE: 14

```
Met Ala Gln Pro Val Gly Ile Asn Thr Ser Thr Thr Cys Cys Tyr Arg
  1               5                  10                  15

Phe Ile Asn Lys Lys Ile Pro Lys Gln Arg Leu Glu Ser Tyr Arg Arg
                 20                  25                  30

Thr Thr Ser Ser His Cys Pro Arg Glu Ala Val Ile Phe Lys Thr Lys
             35                  40                  45

Leu Asp Lys Glu Ile Cys Ala Asp Pro Thr Gln Lys Trp Val Gln Asp
 50                  55                  60

Phe Met Lys His Leu Asp Lys Lys Thr Gln Thr Pro Lys Leu Glu Phe
 65                  70                  75                  80

Asn Asp Ala Gln Ala Pro Lys Ser Leu Asp Met Gly Leu Glu Ala Glu
                 85                  90                  95

Glu Gln Lys Leu Ile Ser Glu Glu Asp Leu Pro Ser Asp Val Glu Val
                100                 105                 110

Gln Leu Gln Gln Ser Gly Pro Asp Leu Val Lys Pro Gly Met Ser Val
            115                 120                 125

Lys Leu Ser Cys Lys Thr Leu Gly Tyr Asn Phe Ser Asp Lys Arg Ile
130                 135                 140

His Trp Ile Lys Gln Lys Pro Gly Arg Gly Leu Glu Trp Val Gly Arg
145                 150                 155                 160

Ile Asp Pro Ser Asn Gly Asp Thr Asp Tyr Asn Ala Asp Phe Lys Thr
                165                 170                 175

Pro Ala Thr Leu Thr Val Asp Arg Pro Ser Asn Thr Ala Tyr Leu Glu
                180                 185                 190

Leu Ser Asn Leu Thr Ser Gly Asp Ser Ala Val Tyr Tyr Cys Ser Ile
            195                 200                 205

Ser Gly Asp Tyr Ser Ala Cys Asp Tyr Trp Gly Gln Gly Thr Glu Leu
210                 215                 220

Thr Val Ser Ser Gly Gly Gly Ser Gly Gly Gly Ser Gly Gly Gly Gly
225                 230                 235                 240

Gly Gly Ser Asp Val Val Met Thr Gln Thr Pro Leu Ser Leu Ala Val
                245                 250                 255

Ser Leu Gly Asp His Val Lys Met Ser Cys Arg Cys Asn Gln Ser Leu
                260                 265                 270

Val Asn Ser His Gly Asp Ser Phe Leu His Trp Phe Leu Gln Lys Pro
            275                 280                 285

Gly Gln Ser Pro Lys Leu Leu Ile Tyr Lys Val Ser Ser Arg Phe Phe
290                 295                 300

Gly Val Pro Glu Arg Phe Ser Gly Ser Gly Ser Gly Thr Asp Phe Thr
305                 310                 315                 320

Leu Glu Ile Ser Arg Val Glu Ala Glu Asp Leu Gly Val Tyr Phe Cys
                325                 330                 335

Ser Gln Gly Ala His Val Pro Trp Thr Phe Gly Gly Gly Thr Lys Leu
            340                 345                 350

Glu Val Lys His His His His His His
355                 360
```

<210> SEQ ID NO 15
<211> LENGTH: 374

```
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 15
```

| Met | Ala | Ile | Pro | Leu | Ala | Arg | Thr | Val | Arg | Cys | Asn | Cys | Ile | His | Ile |
|---|---|---|---|---|---|---|---|---|---|---|---|---|---|---|---|
| 1 | | | | 5 | | | | | 10 | | | | | 15 | |

| Asp | Asp | Gly | Pro | Val | Arg | Met | Arg | Ala | Ile | Gly | Lys | Leu | Glu | Ile | Ile |
|---|---|---|---|---|---|---|---|---|---|---|---|---|---|---|---|
| | | | 20 | | | | | 25 | | | | | 30 | | |

| Pro | Ala | Ser | Leu | Ser | Cys | Pro | Arg | Val | Glu | Ile | Ile | Ala | Thr | Met | Lys |
| | | | 35 | | | | | 40 | | | | | 45 | | |

| Lys | Asn | Asp | Glu | Gln | Arg | Cys | Leu | Asn | Pro | Glu | Ser | Lys | Thr | Ile | Lys |
| 50 | | | | | 55 | | | | | 60 | | | | | |

| Asn | Leu | Met | Lys | Ala | Phe | Ser | Gln | Lys | Arg | Ser | Lys | Arg | Ala | Pro | Ala |
| 65 | | | | | 70 | | | | | 75 | | | | | 80 |

| Lys | Lys | Leu | Asn | Asp | Ala | Gln | Ala | Pro | Lys | Ser | Asp | Leu | Glu | Asp | Ile |
| | | | | 85 | | | | | 90 | | | | | 95 | |

| Gln | Met | Thr | Gln | Ser | Pro | Ser | Ser | Leu | Ser | Ala | Ser | Leu | Gly | Gly | Lys |
| | | | | 100 | | | | | 105 | | | | | 110 | |

| Val | Thr | Ile | Thr | Cys | Lys | Ala | Ser | Gln | Asp | Ile | Asn | Lys | Tyr | Ile | Ala |
| | | | | 115 | | | | | 120 | | | | | 125 | |

| Trp | Tyr | Gln | His | Lys | Pro | Gly | Lys | Gly | Pro | Arg | Leu | Leu | Ile | His | Tyr |
| | 130 | | | | | 135 | | | | | 140 | | | | |

| Thr | Ser | Thr | Leu | Gln | Pro | Gly | Ile | Pro | Ser | Arg | Phe | Ser | Gly | Ser | Gly |
| 145 | | | | | 150 | | | | | 155 | | | | | 160 |

| Ser | Gly | Arg | Asp | Tyr | Ser | Phe | Ser | Ile | Ser | Asn | Leu | Glu | Pro | Glu | Asp |
| | | | | 165 | | | | | 170 | | | | | 175 | |

| Ile | Ala | Thr | Tyr | Tyr | Cys | Leu | Gln | Tyr | Asp | Asn | Leu | Tyr | Thr | Phe | Gly |
| | | | | 180 | | | | | 185 | | | | | 190 | |

| Gly | Gly | Thr | Lys | Leu | Glu | Ile | Lys | Glu | Gly | Lys | Ser | Ser | Gly | Ser | Gly |
| | | | 195 | | | | | 200 | | | | | 205 | | |

| Ser | Glu | Ser | Lys | Glu | Phe | Glu | Val | Lys | Leu | Val | Glu | Ser | Gly | Gly | Gly |
| | 210 | | | | | 215 | | | | | 220 | | | | |

| Leu | Val | Gln | Pro | Gly | Gly | Ser | Leu | Ser | Leu | Ser | Cys | Ala | Ala | Ser | Gly |
| 225 | | | | | 230 | | | | | 235 | | | | | 240 |

| Phe | Thr | Phe | Thr | Asp | Tyr | Tyr | Met | Ser | Trp | Val | Arg | Gln | Pro | Pro | Gly |
| | | | | 245 | | | | | 250 | | | | | 255 | |

| Lys | Ala | Leu | Glu | Trp | Leu | Ala | Leu | Ile | Arg | Asn | Lys | Ala | Asn | Gly | Tyr |
| | | | | 260 | | | | | 265 | | | | | 270 | |

| Thr | Thr | Glu | Tyr | Ser | Ala | Ser | Val | Lys | Gly | Arg | Phe | Thr | Ile | Ser | Arg |
| | | | 275 | | | | | 280 | | | | | 285 | | |

| Asp | Asn | Ser | Gln | Ser | Ile | Leu | Tyr | Leu | Gln | Met | Asn | Ala | Leu | Arg | Ala |
| | 290 | | | | | 295 | | | | | 300 | | | | |

| Glu | Asp | Ser | Ala | Thr | Tyr | Tyr | Cys | Ala | Arg | Asp | Pro | Asn | Tyr | Tyr | Asp |
| 305 | | | | | 310 | | | | | 315 | | | | | 320 |

| Gly | Ser | Tyr | Glu | Gly | Tyr | Phe | Asp | Tyr | Trp | Ala | Gln | Gly | Thr | Thr | Leu |
| | | | | 325 | | | | | 330 | | | | | 335 | |

| Thr | Val | Ser | Ser | Gly | Gly | Gly | Ser | Gly | Gly | Gly | Ser | Gly | Gly | Ser | Gly |
| | | | 340 | | | | | 345 | | | | | 350 | | |

| Gly | Gly | Ser | Ala | Glu | Glu | Gln | Lys | Leu | Ile | Ser | Glu | Glu | Asp | Leu | Ala |
| | | | 355 | | | | | 360 | | | | | 365 | | |

| His | His | His | His | His |
| | 370 | | | | |

```
<210> SEQ ID NO 16
<211> LENGTH: 359
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 16

Met Ala Gln Pro Val Gly Ile Asn Thr Ser Thr Thr Cys Cys Tyr Arg
 1               5                  10                  15

Phe Ile Asn Lys Lys Ile Pro Lys Gln Arg Leu Glu Ser Tyr Arg Arg
             20                  25                  30

Thr Thr Ser Ser His Cys Pro Arg Glu Ala Val Ile Phe Lys Thr Lys
         35                  40                  45

Leu Asp Lys Glu Ile Cys Ala Asp Pro Thr Gln Lys Trp Val Gln Asp
 50                  55                  60

Phe Met Lys His Leu Asp Lys Lys Thr Gln Thr Pro Lys Leu Glu Phe
65                  70                  75                  80

Asn Asp Ala Gln Ala Pro Lys Ser Leu Glu Val Lys Leu Val Glu Ser
                 85                  90                  95

Gly Gly Gly Leu Val Gln Pro Gly Gly Ser Leu Ser Leu Ser Cys Ala
            100                 105                 110

Ala Ser Gly Phe Thr Phe Thr Asp Tyr Tyr Met Ser Trp Val Arg Gln
        115                 120                 125

Pro Pro Gly Lys Ala Leu Glu Trp Leu Ala Leu Ile Arg Asn Lys Ala
    130                 135                 140

Asn Gly Tyr Thr Thr Glu Tyr Ser Ala Ser Val Lys Gly Arg Phe Thr
145                 150                 155                 160

Ile Ser Arg Asp Asn Ser Gln Ser Ile Leu Tyr Leu Gln Met Asn Ala
                165                 170                 175

Leu Arg Ala Glu Asp Ser Ala Thr Tyr Tyr Cys Ala Arg Asp Pro Asn
            180                 185                 190

Tyr Tyr Asp Gly Ser Tyr Glu Gly Tyr Phe Asp Tyr Trp Ala Gln Gly
        195                 200                 205

Thr Thr Leu Thr Val Ser Ser Gly Gly Gly Ser Gly Gly Gly Gly
    210                 215                 220

Ser Gly Gly Gly Ser Gly Ser Asp Ile Gln Met Thr Gln Ser Pro
225                 230                 235                 240

Ser Ser Leu Ser Ala Ser Leu Gly Gly Lys Val Thr Ile Thr Cys Lys
                245                 250                 255

Ala Ser Gln Asp Ile Asn Lys Tyr Ile Ala Trp Tyr Gln His Lys Pro
            260                 265                 270

Gly Lys Gly Pro Arg Leu Leu Ile His Tyr Thr Ser Thr Leu Gln Pro
        275                 280                 285

Gly Ile Pro Ser Arg Phe Ser Gly Ser Gly Ser Gly Arg Asp Tyr Ser
    290                 295                 300

Phe Ser Ile Ser Asn Leu Glu Pro Glu Asp Ile Ala Thr Tyr Tyr Cys
305                 310                 315                 320

Leu Gln Tyr Asp Asn Leu Tyr Thr Phe Gly Gly Gly Thr Lys Leu Glu
                325                 330                 335

Ile Lys Gly Ser Ala Glu Glu Gln Lys Leu Ile Ser Glu Glu Asp Leu
            340                 345                 350

Ala His His His His His His
```

355

<210> SEQ ID NO 17
<211> LENGTH: 27
<212> TYPE: DNA
<213> ORGANISM: Artificial Sequence
<220> FEATURE:
<223> OTHER INFORMATION: Description of artificial sequence:/
      note=synthetic construct

<400> SEQUENCE: 17
ctcgaggtga agctggtgga gtctgga                                      27

<210> SEQ ID NO 18
<211> LENGTH: 26
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 18
agaggagact gtgagagtgg tgcctt                                       26

<210> SEQ ID NO 19
<211> LENGTH: 24
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 19
gacatccaga tgacacagtc tcca                                         24

<210> SEQ ID NO 20
<211> LENGTH: 36
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 20 ggatccttttt atttccagct tggtcccccc tccgaa                           36

<210> SEQ ID NO 21
<211> LENGTH: 32
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 21
ccatggtcca actgcagcag tcagggcctg ac                                32

<210> SEQ ID NO 22
<211> LENGTH: 30
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 22
tgaggagact gtgagttcgg taccttggcc                                   30

<210> SEQ ID NO 23
<211> LENGTH: 27
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 23
gatgttgtga tgacgcagac tccactc                                27

<210> SEQ ID NO 24
<211> LENGTH: 31
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 24
ggatcctttg acttccagct ttgtgcctcc a                           31

<210> SEQ ID NO 25
<211> LENGTH: 72
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 25
ggatccgcag aagaacagaa actgatctca gaagaggatc tggcccacca ccatcaccat    60
cactaacccg gg                                                       72

<210> SEQ ID NO 26
<211> LENGTH: 32
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 26
ccatggccat ccctctcgca aggacggtcc gc                          32

<210> SEQ ID NO 27
<211> LENGTH: 30
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 27
gaattcagga gcccttttag acctttttg                              30

<210> SEQ ID NO 28
<211> LENGTH: 30
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 28
accatggccc aaccagatgg gcccaatgca 30

<210> SEQ ID NO 29
<211> LENGTH: 30
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 29
gaattcaggc tttggagttg gggttttcat 30

<210> SEQ ID NO 30
<211> LENGTH: 34
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 30
accatggcgc aaccggtagg tataaacaca agca 34

<210> SEQ ID NO 31
<211> LENGTH: 31
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 31
gaattccagt ttcggcgtct gtgtcttttt a 31

<210> SEQ ID NO 32
<211> LENGTH: 27
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 32
cccatggtac ctctctctag aaccgta 27

<210> SEQ ID NO 33
<211> LENGTH: 40
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 33
ggatccttaa ggagatcttt tagacatttc cttgctaact 40

<210> SEQ ID NO 34
<211> LENGTH: 36
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 34
gaattcaacg acgctcaggc gccgaagagt ctcgag 36

<210> SEQ ID NO 35
<211> LENGTH: 1047
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 35

| | | | | | |
|---|---|---|---|---|---|
| atggtacctc | tctctagaac | cgtacgctgt | acctgcatca | gcattagtaa | tcaacctgtt | 60 |
| aatccaaggt | ctttagaaaa | acttgaaatt | attcctgcaa | gccaattttg | tccacgtgtt | 120 |
| gagatcattg | ctacaatgaa | aaagaagggt | gagaagagat | gtctgaatcc | agaatcgaag | 180 |
| gccatcaaga | atttactgaa | agcagttagc | aaggaaatgt | ctaaaagatc | catgggcctc | 240 |
| gaggcagaag | aacagaaact | gatctcagaa | gaggatctgc | cgagtgatgt | cgaggtccaa | 300 |
| ctgcagcagt | cagggcctga | ccttgtgaaa | cctgggatgt | ccgtgaaact | gtcctgtaag | 360 |
| actttgggtt | acaatttctc | cgacaagcgg | attcactgga | ttaaacagaa | gcctggccga | 420 |
| ggccttgaat | gggttggaag | gattgatcct | tctaacggtg | atactgacta | taatgcggac | 480 |
| ttcaagaccc | cggccacact | aactgttgac | agaccctcca | acacagccta | cttagaactc | 540 |
| agcaacctga | catctgggga | ctctgcggtc | tattattgtt | caatatcggg | tgattattcc | 600 |
| gcctgcgact | attggggcca | aggtaccgaa | ctcacagtct | cctcaggtgg | tggtggttct | 660 |
| ggcggcggcg | gatctggtgg | cggtgggagc | gatgttgtga | tgacgcagac | tccactctcc | 720 |
| ctggccgtca | gtcttggaga | tcacgtgaaa | atgtcttgta | gatgtaatca | gagccttgta | 780 |
| aacagtcatg | gagactcctt | tttacactgg | tttctgcaga | agccaggcca | gtctccaaag | 840 |
| ctcctgatct | acaaggtttc | cagccgattt | tttggggtcc | cagagaggtt | cagtggcagt | 900 |
| ggttcaggga | cagatttcac | actcgagatc | agtcgagtgg | aggctgagga | tctgggagtt | 960 |
| tatttctgtt | ctcaaggtgc | acatgttccg | tggacgttcg | gtggaggcac | aaagctggaa | 1020 |
| gtcaaacacc | accatcacca | tcactag | | | | 1047 |

<210> SEQ ID NO 36
<211> LENGTH: 1086
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 36

| | | | | | |
|---|---|---|---|---|---|
| atggtacctc | tctctagaac | cgtacgctgt | acctgcatca | gcattagtaa | tcaacctgtt | 60 |
| aatccaaggt | ctttagaaaa | acttgaaatt | attcctgcaa | gccaattttg | tccacgtgtt | 120 |
| gagatcattg | ctacaatgaa | aaagaagggt | gagaagagat | gtctgaatcc | agaatcgaag | 180 |
| gccatcaaga | atttactgaa | agcagttagc | aaggaaatgt | ctaaaagatc | tgccaggaaa | 240 |
| ctgaacgacg | ctcaggcgcc | gaagagtgat | ctcgaggtga | agctggtgga | gtctggagga | 300 |
| ggcttggtac | agcctggggg | ttctctgagt | ctctcctgtg | cagcttctgg | attcaccttc | 360 |
| actgattact | acatgagctg | ggtccgccag | cctccaggga | aggcacttga | gtggttggct | 420 |
| ttgattagaa | acaaagctaa | tggttacaca | acagagtaca | gtgcatctgt | gaagggtcgg | 480 |
| ttcaccatct | ccagagataa | ttcccaaagc | atcctctatc | ttcaaatgaa | tgccctgaga | 540 |
| gctgaggaca | gtgccactta | ttactgtgca | agagatccca | attactacga | tggtagctac | 600 |

| | |
|---|---:|
| gaagggtact tgactactg ggcgcaaggc accactctca cagtctcctc tggtggtggt | 660 |
| ggttctggcg gcggcggcag cggtggcggt gggagcggat ctgacatcca gatgacacag | 720 |
| tctccatcct cactgtctgc atctctggga ggcaaagtca ccatcacttg caaggcaagc | 780 |
| caagacatta acaagtatat agcttggtac aacacaagc ctggaaaagg tcctaggctg | 840 |
| ctcatacatt acacatctac attacagcca ggcatcccat caaggttcag tggaagtggg | 900 |
| tctgggagag attattcctt cagcatcagc aacctggagc ctgaagatat tgcaacttat | 960 |
| tattgtctac agtatgataa tctgtacacg ttcggagggg ggaccaagct ggaaataaaa | 1020 |
| ggatccgcag aagaacagaa actgatctca gaagaggatc tggcccacca ccatcaccat | 1080 |
| cactaa | 1086 |

<210> SEQ ID NO 37
<211> LENGTH: 1086
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 37

| | |
|---|---:|
| atggcgcaac cggtaggtat aaacacaagc acaacctgtt gctatcgttt cataaataaa | 60 |
| aagataccga agcaacgtct ggaaagctat cgccgtacca cttctagcca ctgtccgcgt | 120 |
| gaagctgtta tattcaaaac gaaactggat aaggagatct cgccgaccc tacacagaaa | 180 |
| tgggttcagg actttatgaa gcacctggat aaaaagacac agacgccgaa actggaattc | 240 |
| aacgacgctc aggcgccgaa gagtctcgac atgggcctcg aggcagaaga acagaaactg | 300 |
| atctcagaag aggatctgcc gagtgatgtc gaggtccaac tgcagcagtc agggcctgac | 360 |
| cttgtgaaac tgggatgtc cgtgaaactg tcctgtaaga cttggggtta caatttctcc | 420 |
| gacaagcgga ttcactggat taaacagaag cctggccgag gccttgaatg ggttggaagg | 480 |
| attgatcctt ctaacggtga tactgactat aatgcggact tcaagacccc ggccacacta | 540 |
| actgttgaca gaccctccaa cacagcctac ttagaactca gcaacctgac atctggggac | 600 |
| tctgcggtct attattgttc aatatcgggt gattattccg cctgcgacta ttggggccaa | 660 |
| ggtaccgaac tcacagtctc ctcaggtggt ggtggttctg gcggcggcgg atctggtggc | 720 |
| ggtgggagcg atgttgtgat gacgcagact ccactctccc tggccgtcag tcttggagat | 780 |
| cacgtgaaaa tgtcttgtag atgtaatcag agccttgtaa acagtcatgg agactccttt | 840 |
| ttacactggt ttctgcagaa gccaggccag tctccaaagc tcctgatcta caaggttttcc | 900 |
| agccgatttt ttggggtccc agagaggttc agtggcagtg gttcagggac agatttcaca | 960 |
| ctcgagatca gtcgagtgga ggctgaggat ctgggagttt atttctgttc tcaaggtgca | 1020 |
| catgttccgt ggacgttcgg tggaggcaca aagctggaag tcaaacacca ccatcaccat | 1080 |
| cactag | 1086 |

<210> SEQ ID NO 38
<211> LENGTH: 1113
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 38

| | |
|---|---:|
| atggcgcaac cggtaggtat aaacacaagc acaacctgtt gctatcgttt cataaataaa | 60 |

```
aagataccga agcaacgtct ggaaagctat cgccgtacca cttctagcca ctgtccgcgt    120
gaagctgtta tattcaaaac gaaactggat aaggagatct gcgccgaccc tacacagaaa    180
tgggttcagg actttatgaa gcacctggat aaaaagacac agacgccgaa actggaattc    240
aacgacgctc aggcgccgaa gagtctcgag gacatccaga tgacacagtc tccatcctca    300
ctgtctgcat ctctgggagg caaagtcacc atcacttgca aggcaagcca agacattaac    360
aagtatatag cttggtacca acacaagcct ggaaaggtc ctaggctgct catacattac     420
acatctacat tacagccagg catcccatca aggttcagtg aagtgggtc tgggagagat     480 tattccttca gcatcagcaa cctggagcct gaagatattg caacttatta ttgtctacag    540
tatgataatc tgtacacgtt cggagggggg accaagctgg aaataaaaga gggtaaatcc    600
tcaggatctg gctccgaatc caaagaattc gaggtgaagc tggtggagtc tggaggaggc    660
ttggtacagc ctgggggttc tctgagtctc tcctgtgcag cttctggatt caccttcact    720
gattactaca tgagctgggt ccgccagcct ccagggaagg cacttgagtg gttggctttg    780
attagaaaca aagctaatgg ttacacaaca gagtacagtg catctgtgaa gggtcggttc    840
accatctcca gagataattc ccaaagcatc ctctatcttc aaatgaatgc cctgagagct    900
gaggacagtg ccacttatta ctgtgcaaga gatcccaatt actacgatgg tagctacgaa    960
gggtactttg actactggc gcaaggcacc actctcacag tctcctctgg tggtggtggt   1020
tctggcggcg gcggcagcgg tggcggtgga tccgcagaag aacagaaact gatctcagaa   1080
gaggatctgg cccaccacca tcaccatcac taa                                1113
```

<210> SEQ ID NO 39  
<211> LENGTH: 1080  
<212> TYPE: DNA  
<213> ORGANISM: Artificial Sequence  
<220> FEATURE:  
<223> OTHER INFORMATION: Description of artificial sequence: /note=synthetic construct

<400> SEQUENCE: 39

```
atggcgcaac cggtaggtat aaacacaagc acaacctgtt gctatcgttt cataaataaa     60
aagataccga agcaacgtct ggaaagctat cgccgtacca cttctagcca ctgtccgcgt    120
gaagctgtta tattcaaaac gaaactggat aaggagatct gcgccgaccc tacacagaaa    180
tgggttcagg actttatgaa gcacctggat aaaaagacac agacgccgaa actggaattc    240
aacgacgctc aggcgccgaa gagtctcgag gtgaagctgg tggagtctgg aggaggcttg    300
gtacagcctg ggggttctct gagtctctcc tgtgcagctt ctggattcac cttcactgat    360
tactacatga gctgggtccg ccagcctcca gggaaggcac ttgagtggtt ggctttgatt    420
agaaacaaag ctaatggtta cacaacagag tacagtgcat ctgtgaaggg tcggttcacc    480
atctccagag ataattccca aagcatcctc tatcttcaaa tgaatgccct gagagctgag    540
gacagtgcca cttattactg tgcaagagat cccaattact acgatggtag ctacgaaggg    600
tactttgact actgggcgca aggcaccact ctcacagtct cctctggtgg tggttct       660 ggcggcggcg gcagcggtgg cggtgggagc ggatctgaca tccagatgac acagtctcca    720
tcctcactgt ctgcatctct gggaggcaaa gtcaccatca cttgcaaggc aagccaagac    780
attaacaagt atatagcttg gtaccaacac aagcctggaa aaggtcctag gctgctcata    840
cattacacat ctacattaca gccaggcatc ccatcaaggt tcagtggaag tgggtctggg    900
agagattatt ccttcagcat cagcaacctg agcctgaag atattgcaac ttattattgt    960
```

```
ctacagtatg ataatctgta cacgttcgga gggggggacca agctggaaat aaaaggatcc    1020
gcagaagaac agaaactgat ctcagaagag gatctggccc accaccatca ccatcactaa   1080
```

<210> SEQ ID NO 40
<211> LENGTH: 20
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 40

Pro Asp Thr Arg Pro Ala Pro Gly Ser Thr Ala Pro Pro Ala His Gly
 1               5                  10                  15

Val Thr Ser Ala
            20

<210> SEQ ID NO 41
<211> LENGTH: 1005
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 41

```
atgggcccct acggcgccaa catggaagac agcgtctgct gccgtgatta cgtccgttac     60
cgtctgcccc tgcgcgtggt gaaacacttc tactggacct cagactcctg cccgaggcct    120
ggcgtggtgt tgctaacctt cagggataag gagatctgtg ccgatcccag agtgccctgg    180
gtgaagatga ttctcaataa gctgagccaa aacgacgctc aggcgccgaa gagtctcgag    240
gtacaactgt tggaatctgg gggggggcttg gtgcagtctg gggggtccct gagactgtcc    300
tgtgtagcct ctggactcac ctttagtagt tctgccatta cttgggtccg ccaggctccg    360
gggaaggggc tggagtgggt ctcaggtatc agttttttctg gtgataccac atactacgca    420
gactccgtga agggtcgctt cagcgcctcc agagacaact ccaagaacac agtgtacctg    480
caaatgaaca atctgagacc caatgacacg gcagtgtatt tctgtgcgaa caatcaaacg    540
gggaattttt gccttgacaa ctgggggccag ggaaccctgg tcaccgtctc ctctagaggt    600
ggtggtggtt ctggcggcgg cggcagcggt ggcggtggga gcggatctca atctgttcta    660
actcaacccc cctctgtttc tgcagctccc ggtcagaggg tcaccatctc ttgcactggg    720
agcaggtcca acatcggggc aggttatgat gtcaactggt accaaaaatt cccagaaaca    780
gcacccaaag tcctcatata tagtaataat aatcgaccct ccggtgtccc tgaccgattc    840
tctggctcca agtctggcac ttcagcctcc ctggccatca ctgggctcca acttgaggat    900
gagggtactt attactgcca gtgcaatgac gacagcctga gtggttggct tttcggggga    960
gggaccaagc tgaccgtcct acgtcatcac catcatcacc actag                  1005
```

<210> SEQ ID NO 42
<211> LENGTH: 519
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 42

```
atgggcccct acggcgccaa catggaagac agcgtctgct gccgtgatta cgtccgttac     60
```

| | |
|---|---|
| cgtctgcccc tgcgcgtggt gaaacacttc tactggacct cagactcctg cccgaggcct | 120 |
| ggcgtggtgt tgctaacctt cagggataag gagatctgtg ccgatcccag agtgccctgg | 180 |
| gtgaagatga ttctcaataa gctgagccaa aacgacgctc aggcgccgaa gagtctcgac | 240 |
| ggtgtaactt ctgccccgga cactcgccca gcaccgggtt ctactgctcc gccggcacac | 300 |
| gcgaattctc cggacactcg cccagcaccg ggttctactg ctccgccggc acacggtgta | 360 |
| acttctgccg ccctcgacgg tgtaacttct gccccggaca ctcgcccagc accgggttct | 420 |
| actgctccgc cggcacacgc gaattctccg gacactcgcc cagcaccggg ttctactgct | 480 |
| ccgccggcac acggtgtaac ttctgccgcc ctcgagtaa | 519 |

<210> SEQ ID NO 43
<211> LENGTH: 1763
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 43

| | |
|---|---|
| atgggcccct acggcgccaa catggaagac agcgtctgct gccgtgatta cgtccgttac | 60 |
| cgtctgcccc tgcgcgtggt gaaacacttc tactggacct cagactcctg cccgaggcct | 120 |
| ggcgtggtgt tgctaacctt cagggataag gagatctgtg ccgatcccag agtgccctgg | 180 |
| gtgaagatga ttctcaataa gctgagccaa aacgacgctc aggcgccgaa gagtctcgag | 240 |
| gctgcagaaa acttgtgggt cacagtctat tatggggtac ctgtgtggaa agaagcaacc | 300 |
| accactctat tttgtgcatc agatgctaaa gcatatgaaa cagaagtaca taatgtctgg | 360 |
| gccacacatg cctgtgtacc cacagacccc aacccacaag aagtattatt ggaaaatgtg | 420 |
| acagaaaact taacatgtgt gaagaataac atggtagaac agatgcagga ggatataatc | 480 |
| agtttatggg atcaaagcct aaagccatgt gtaaaattaa ccccactctg tgttacttta | 540 |
| gagtgtcatg atgtgaatgt gaatggcact gctaataatg gcactactaa tgtcactgag | 600 |
| agtggtgtca atagtagtga tgtcactagt aataatgtca ctaatagtaa ttggggaaca | 660 |
| atggaaaagg gagaaataaa aaactgctct ttcaatatca ccacaaacat aagagataag | 720 |
| atgcagaaag aaactgcaca gttttataaa cttgatatag taccaataga ggatcagaat | 780 |
| aagacgaata atactctcta tagattaata aattgtaata cctcagtcat tacacaggcc | 840 |
| tgtccaaagg tatcctttga accaattccc atacattatt gtaccccggc tggttttgcg | 900 |
| attctaaagt gtaatgatag gaatttcaat ggaacaggac catgtaaaaa tgtcagcaca | 960 |
| gtacaatgta cacatggcat taagccagta gtgtcaactc aactgctgtt aaatggcagt | 1020 |
| ctagcagaag cagaggtagt aatcagatct gaaaatttca cgaacaatgc taaaactata | 1080 |
| ataatacagc tgaatgaaac tgtagagatt aattgtacaa gacccaacaa caatacaagc | 1140 |
| aaaagaatat ctataggacc agggagagca tttcgcgcaa caagataat aggaaaatata | 1200 |
| agacaagcac attgtaacat tagtagagca acatggaaca gcactttaaa aagatagtt | 1260 |
| gcaaaattaa gagaacaatt tgggaataaa acaatagtct ttcaaccatc ctcaggaggg | 1320 |
| gacccagaaa ttgtaatgca cagttttaat tgtggagggg aattcttcta ctgtaataca | 1380 |
| acacaactgt ttaatagtac ttggaatagt actgaagagt caaatagcac tgaagaaggc | 1440 |
| acaatcactc tcccatgtag aataaaacaa attataaaca tgtggcaaga agtaggaaaa | 1500 |
| gcaatgtatg cccctcccat tgaaggacaa attagatgtt catcaaatat tacagggctg | 1560 |

```
ctattaacaa gagatggtgg taacaataac aaaacaaacg ggactgagat cttcagacct    1620
ggaggaggag atatgaggga caattggaga agtgaattat ataaatataa agtagtaaaa    1680
attgaaccat taggagtagc acccaccaag gcaaagagaa gagtggtgca gagagaaaaa    1740
agagcagtgg ggatagtagg taa                                            1763
```

<210> SEQ ID NO 44
<211> LENGTH: 1047
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 44

```
atggcgcaac cggtaggtat aaacacaagc acaacctgtt gctatcgttt cataaataaa      60
aagataccga agcaacgtct ggaaagctat cgccgtacca cttctagcca ctgtccgcgt     120
gaagctgtta tattcaaaac gaaactggat aaggagatct cgccgaccc tacacagaaa     180 tgggttcagg actttatgaa gcacctggat aaaaagacac agacgccgaa actggaattc    240
aacgacgctc aggcgccgaa gagtctcgac atgggcctcg aggtacaact gttggaatct    300 gggggggct tggtgcagtc tgggggggtcc ctgagactgt cctgtgtagc ctctggactc    360
acctttagta gttctgccat tacttgggtc cgccaggctc cggggaaggg gctggagtgg    420
gtctcaggta tcagttttttc tggtgatacc acatactacg cagactccgt gaagggtcgc    480
ttcagcgcct ccagagacaa ctccaagaac acagtgtacc tgcaaatgaa caatctgaga    540
cccaatgaca cggcagtgta tttctgtgcg aacaatcaaa cggggaattt ttgccttgac    600
aactggggcc agggaaccct ggtcaccgtc tcctctagag gtggtggtgg ttctggcggc    660
ggcggcagcg gtggcggtgg gagcggatct caatctgttc taactcaacc cccctctgtt    720
tctgcagctc ccggtcagag ggtcaccatc tcttgcactg ggagcaggtc caacatcggg    780
gcaggttatg atgtcaactg gtaccaaaaa tttccagaaa cagcacccaa agtcctcata    840
tatagtaata ataatcgacc ctccggtgtc cctgaccgat tctctggctc caagtctggc    900
acttcagcct ccctggccat cactgggctc caacttgagg atgagggtac ttattactgc    960
cagtgcaatg acgacagcct gagtggttgg cttttcgggg agggaccaa gctgaccgtc   1020 ctacgtcatc accatcatca ccactag                                       1047
```

<210> SEQ ID NO 45
<211> LENGTH: 1805
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 45

```
atggcgcaac cggtaggtat aaacacaagc acaacctgtt gctatcgttt cataaataaa      60
aagataccga agcaacgtct ggaaagctat cgccgtacca cttctagcca ctgtccgcgt     120
gaagctgtta tattcaaaac gaaactggat aaggagatct cgccgaccc tacacagaaa     180 tgggttcagg actttatgaa gcacctggat aaaaagacac agacgccgaa actggaattc    240
aacgacgctc aggcgccgaa gagtctcgac atgggcctcg aggctgcaga aaacttgtgg    300
gtcacagtct attatggggt acctgtgtgg aagaagcaa ccaccactct attttgtgca     360
```

```
tcagatgcta aagcatatga aacagaagta cataatgtct gggccacaca tgcctgtgta    420
cccacagacc ccaacccaca agaagtatta ttggaaaatg tgacagaaaa ctttaacatg    480
tggaagaata acatggtaga acagatgcag gaggatataa tcagtttatg ggatcaaagc    540
ctaaagccat gtgtaaaatt aaccccactc tgtgttactt tagagtgtca tgatgtgaat    600
gtgaatggca ctgctaataa tggcactact aatgtcactg agagtggtgt caatagtagt    660
gatgtcacta gtaataatgt cactaatagt aattgggaa caatggaaaa gggagaaata     720
aaaaactgct ctttcaatat caccacaaac ataagagata gatgcagaa agaaactgca     780 cagtttata aacttgatat agtaccaata gaggatcaga ataagacgaa taatactctc      840
tatagattaa taaattgtaa tacctcagtc attacacagg cctgtccaaa ggtatccttt    900
gaaccaattc ccatacatta ttgtaccccg gctggttttg cgattctaaa gtgtaatgat    960
aggaatttca atggaacagg accatgtaaa atgtcagca cagtacaatg tacacatggc     1020
attaagccag tagtgtcaac tcaactgctg ttaaatggca gtctagcaga agcagaggta    1080
gtaatcagat ctgaaaattt cacgaacaat gctaaaacta ataatacaa gctgaatgaa     1140 actgtagaga ttaattgtac aagacccaac aacaatacaa gcaaaagaat atctatagga    1200
ccagggagag catttcgcgc aacaaagata ataggaaata taagacaagc acattgtaac    1260
attagtagag caacatggaa cagcacttta aaaaagatag ttgcaaaatt aagagaacaa    1320
tttgggaata aaacaatagt cttcaacca tcctcaggag gggacccaga aattgtaatg     1380 cacagttta attgtggagg ggaattcttc tactgtaata caacaact gtttaatagt      1440 acttggaata gtactgaaga gtcaaatagc actgaagaag gcacaatcac tctcccatgt    1500
agaataaaac aaattataaa catgtggcaa gaagtaggaa aagcaatgta tgcccctccc    1560
attgaaggac aaattagatg ttcatcaaat attacagggc tgctattaac aagagatggt    1620
ggtaacaata acaaaacaaa cgggactgag atcttcagac tggaggagg agatatgagg    1680 gacaattgga gaagtgaatt atataaaatat aaagtagtaa aaattgaacc attaggagta   1740
gcacccacca aggcaaagag aagagtggtg cagagagaaa aaagagcagt ggggatagta    1800
ggtaa                                                                1805
```

<210> SEQ ID NO 46
<211> LENGTH: 534
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 46

```
atggacggga agcccgtcag cctgagctac agatgcccat gccgattctt cgaaagccat     60
gttgccagag ccaacgtcaa gcatctcaaa attctcaaca ctccaaactg tgcccttcag    120
attgtagccc ggctgaagaa caacaacaga caagtgtgca ttgacccgaa gctaaagtgg    180
attcaggagt acctggagaa agctttaaac aagaggttca agatgaacga cgctcaggcg    240
ccgaagagtc tcgacggtgt aacttctgcc ccggacactc gcccagcacc gggttctact    300
gctccgccgg cacacgcgaa ttctccggac actcgcccag caccgggttc tactgctccg    360
ccggcacacg gtgtaacttc tgccgccctc gacggtgtaa cttctgcccc ggacactcgc    420
ccagcaccgg gttctactgc tccgccggca cacgcgaatt ctccggacac tcgcccagca    480
ccgggttcta ctgctccgcc ggcacacggt gtaacttctg ccgccctcga gtaa          534
```

<210> SEQ ID NO 47
<211> LENGTH: 1020
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 47

| | | | | | |
|---|---|---|---|---|---|
| atggacggga | agcccgtcag | cctgagctac | agatgcccat | gccgattctt | cgaaagccat | 60 |
| gttgccagag | ccaacgtcaa | gcatctcaaa | attctcaaca | ctccaaactg | tgcccttcag | 120 |
| attgtagccc | ggctgaagaa | caacaacaga | caagtgtgca | ttgacccgaa | gctaaagtgg | 180 |
| attcaggagt | acctggagaa | agctttaaac | aagaggttca | agatgaacga | cgctcaggcg | 240 |
| ccgaagagtc | tcgaggtaca | actgttggaa | tctggggggg | gcttggtgca | gtctgggggg | 300 |
| tccctgagac | tgtcctgtgt | agcctctgga | ctcaccttta | gtagttctgc | cattacttgg | 360 |
| gtccgccagg | ctccggggaa | ggggctggag | tgggtctcag | gtatcagttt | ttctggtgat | 420 |
| accacatact | acgcagactc | cgtgaagggt | cgcttcagcg | cctccagaga | caactccaag | 480 |
| aacacagtgt | acctgcaaat | gaacaatctg | agacccaatg | acacggcagt | gtatttctgt | 540 |
| gcgaacaatc | aaacggggaa | ttttttgcctt | gacaactggg | gccagggaac | cctggtcacc | 600 |
| gtctcctcta | gaggtggtgg | tggttctggc | ggcggcggca | gcggtggcgg | tgggagcgga | 660 |
| tctcaatctg | ttctaactca | acccccctct | gtttctgcag | ctcccggtca | gagggtcacc | 720 |
| atctcttgca | ctgggagcag | gtccaacatc | ggggcaggtt | atgatgtcaa | ctggtaccaa | 780 |
| aaatttccag | aaacagcacc | caagtcctc | atatatagta | ataataatcg | accctccggt | 840 |
| gtccctgacc | gattctctgg | ctccaagtct | ggcacttcag | cctccctggc | catcactggg | 900 |
| ctccaacttg | aggatgaggg | tacttattac | tgccagtgca | atgacgacag | cctgagtggt | 960 |
| tggcttttcg | ggggagggac | caagctgacc | gtcctacgtc | atcaccatca | tcaccactag | 1020 |

<210> SEQ ID NO 48
<211> LENGTH: 1787
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 48

| | | | | | |
|---|---|---|---|---|---|
| atggtacctc | tctctagaac | cgtacgctgt | acctgcatca | gcattagtaa | tcaacctgtt | 60 |
| aatccaaggt | ctttagaaaa | acttgaaatt | attcctgcaa | gccaattttg | tccacgtgtt | 120 |
| gagatcattg | ctacaatgaa | aaagaagggt | gagaagagat | gtctgaatcc | agaatcgaag | 180 |
| gccatcaaga | atttactgaa | agcagttagc | aaggaaatgt | ctaaaagatc | tcctaacgac | 240 |
| gctcaggcgc | cgaagagtct | cgaggctgca | gaaaacttgt | gggtcacagt | ctattatggg | 300 |
| gtacctgtgt | ggaaagaagc | aaccaccact | ctattttgtg | catcagatgc | taaagcatat | 360 |
| gaaacagaag | tacataatgt | ctgggccaca | catgcctgtg | tacccacaga | ccccaaccca | 420 |
| caagaagtat | tattgaaaaa | tgtgacagaa | aactttaaca | tgtggaagaa | taacatggta | 480 |
| gaacagatgc | aggaggatat | aatcagttta | tgggatcaaa | gcctaaagcc | atgtgtaaaa | 540 |
| ttaaccccac | tctgtgttac | tttagagtgt | catgatgtga | atgtgaatgg | cactgctaat | 600 |
| aatggcacta | ctaatgtcac | tgagagtggt | gtcaatagta | gtgatgtcac | tagtaataat | 660 |
| gtcactaata | gtaattgggg | aacaatggaa | aagggagaaa | taaaaaactg | ctcttttcaat | 720 |

```
atcaccacaa acataagaga taagatgcag aaagaaactg cacagttta taaacttgat      780
atagtaccaa tagaggatca gaataagacg aataatactc tctatagatt aataaattgt     840
aatacctcag tcattacaca ggcctgtcca aaggtatcct ttgaaccaat tcccatacat     900
tattgtaccc cggctggttt tgcgattcta aagtgtaatg ataggaattt caatggaaca     960
ggaccatgta aaaatgtcag cacagtacaa tgtacacatg gcattaagcc agtagtgtca    1020
actcaactgc tgttaaatgg cagtctagca gaagcagagg tagtaatcag atctgaaaat    1080
ttcacgaaca atgctaaaac tataataata cagctgaata aaactgtaga gattaattgt    1140
acaagaccca caacaatac aagcaaaaga atatctatag gaccagggag agcatttcgc     1200
gcaacaaaga taataggaaa tataagacaa gcacattgta acattagtag agcaacatgg    1260
aacagcactt taaaaagat agttgcaaaa ttaagagaac aatttgggaa taaaacaata    1320
gtctttcaac catcctcagg aggggaccca gaaattgtaa tgcacagttt taattgtgga    1380
ggggaattct tctactgtaa tacaacacaa ctgtttaata gtacttggaa tagtactgaa    1440
gagtcaaata gcactgaaga aggcacaatc actctcccat gtagaataaa acaaattata    1500
aacatgtggc aagaagtagg aaaagcaatg tatgcccctc ccattgaagg acaaattaga    1560
tgttcatcaa atattacagg gctgctatta acaagagatg tggtaacaa taacaaaaca    1620
aacgggactg agatcttcag acctggagga ggagatatga gggacaattg gagaagtgaa    1680
ttatataaat ataagtagt aaaaattgaa ccattaggag tagcacccac caaggcaaag    1740
agaagagtgg tgcagagaga aaaaagagca gtggggatag taggtaa                  1787
```

<210> SEQ ID NO 49
<211> LENGTH: 172
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 49

Met Gly Pro Tyr Gly Ala Asn Met Glu Asp Ser Val Cys Cys Arg Asp
 1               5                  10                  15

Tyr Val Arg Tyr Arg Leu Pro Leu Arg Val Val Lys His Phe Tyr Trp
            20                  25                  30

Thr Ser Asp Ser Cys Pro Arg Pro Gly Val Val Leu Leu Thr Phe Arg
        35                  40                  45

Asp Lys Glu Ile Cys Ala Asp Pro Arg Val Pro Trp Val Lys Met Ile
    50                  55                  60

Leu Asn Lys Leu Ser Gln Asn Asp Ala Gln Ala Pro Lys Ser Leu Asp
65                  70                  75                  80

Gly Val Thr Ser Ala Pro Asp Thr Arg Pro Ala Pro Gly Ser Thr Ala
                85                  90                  95

Pro Pro Ala His Ala Asn Ser Pro Asp Thr Arg Pro Ala Pro Gly Ser
            100                 105                 110

Thr Ala Pro Pro Ala His Gly Val Thr Ser Ala Ala Leu Asp Gly Val
        115                 120                 125

Thr Ser Ala Pro Asp Thr Asn Pro Ala Pro Gly Ser Thr Ala Pro Pro
    130                 135                 140

Ala His Ala Asn Ser Pro Asp Thr Arg Pro Ala Pro Gly Ser Thr Ala
145                 150                 155                 160

Pro Pro Ala His Gly Val Thr Ser Ala Ala Leu Glu
                165                 170

```
<210> SEQ ID NO 50
<211> LENGTH: 587
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 50

Met Gly Pro Tyr Gly Ala Asn Met Glu Asp Ser Val Cys Cys Arg Asp
 1               5                  10                  15

Tyr Val Arg Tyr Arg Leu Pro Leu Arg Val Lys His Phe Tyr Trp
                20                  25                  30

Thr Ser Asp Ser Cys Pro Arg Pro Gly Val Val Leu Leu Thr Phe Arg
                35                  40                  45

Asp Lys Glu Ile Cys Ala Asp Pro Arg Val Pro Trp Val Lys Met Ile
 50                  55                  60

Leu Asn Lys Leu Ser Gln Asn Asp Ala Gln Ala Pro Lys Ser Leu Glu
 65                  70                  75                  80

Ala Ala Glu Asn Leu Trp Val Thr Val Tyr Tyr Gly Val Pro Val Trp
                85                  90                  95

Lys Glu Ala Thr Thr Thr Leu Phe Cys Ala Ser Asp Ala Lys Ala Tyr
                100                 105                 110

Glu Thr Glu Val His Asn Val Trp Ala Thr His Ala Cys Val Pro Thr
                115                 120                 125

Asp Pro Asn Pro Gln Glu Val Leu Leu Glu Asn Val Thr Glu Asn Phe
 130                 135                 140

Asn Met Trp Lys Asn Asn Met Val Glu Gln Met Gln Glu Asp Ile Ile
145                  150                 155                 160

Ser Leu Trp Asp Gln Ser Leu Lys Pro Cys Val Lys Leu Thr Pro Leu
                165                 170                 175

Cys Val Thr Leu Glu Cys His Asp Val Asn Val Asn Gly Thr Ala Asn
                180                 185                 190

Asn Gly Thr Thr Asn Val Thr Glu Ser Gly Val Asn Ser Ser Asp Val
                195                 200                 205

Thr Ser Asn Asn Val Thr Asn Ser Asn Trp Gly Thr Met Glu Lys Gly
 210                 215                 220

Glu Ile Lys Asn Cys Ser Phe Asn Ile Thr Thr Asn Ile Arg Asp Lys
225                  230                 235                 240

Met Gln Lys Glu Thr Ala Gln Phe Tyr Lys Leu Asp Ile Val Pro Ile
                245                 250                 255

Glu Asp Gln Asn Lys Thr Asn Asn Thr Leu Tyr Arg Leu Ile Asn Cys
                260                 265                 270

Asn Thr Ser Val Ile Thr Gln Ala Cys Pro Lys Val Ser Phe Glu Pro
                275                 280                 285

Ile Pro Ile His Tyr Cys Thr Pro Ala Gly Phe Ala Ile Leu Lys Cys
                290                 295                 300

Asn Asp Arg Asn Phe Asn Gly Thr Gly Pro Cys Lys Asn Val Ser Thr
305                  310                 315                 320

Val Gln Cys Thr His Gly Ile Lys Pro Val Val Ser Thr Gln Leu Leu
                325                 330                 335

Leu Asn Gly Ser Leu Ala Glu Ala Glu Val Val Ile Arg Ser Glu Asn
                340                 345                 350
```

-continued

```
Phe Thr Asn Asn Ala Lys Thr Ile Ile Ile Gln Leu Asn Glu Thr Val
            355                 360                 365

Glu Ile Asn Cys Thr Arg Pro Asn Asn Asn Thr Ser Lys Arg Ile Ser
    370                 375                 380

Ile Gly Pro Gly Arg Ala Phe Arg Ala Thr Lys Ile Ile Gly Asn Ile
385                 390                 395                 400

Arg Gln Ala His Cys Asn Ile Ser Arg Ala Thr Trp Asn Ser Thr Leu
                405                 410                 415

Lys Lys Ile Val Ala Lys Leu Arg Glu Gln Phe Gly Asn Lys Thr Ile
            420                 425                 430

Val Phe Gln Pro Ser Ser Gly Gly Asp Pro Glu Ile Val Met His Ser
        435                 440                 445

Phe Asn Cys Gly Gly Glu Phe Phe Tyr Cys Asn Thr Thr Gln Leu Phe
    450                 455                 460

Asn Ser Thr Trp Asn Ser Thr Glu Glu Ser Asn Ser Thr Glu Glu Gly
465                 470                 475                 480

Thr Ile Thr Leu Pro Cys Arg Ile Lys Gln Ile Ile Asn Met Trp Gln
                485                 490                 495

Glu Val Gly Lys Ala Met Tyr Ala Pro Pro Ile Glu Gly Gln Ile Arg
            500                 505                 510

Cys Ser Ser Asn Ile Thr Gly Leu Leu Leu Thr Arg Asp Gly Gly Asn
        515                 520                 525

Asn Asn Lys Thr Asn Gly Thr Glu Ile Phe Arg Pro Gly Gly Gly Asp
    530                 535                 540

Met Arg Asp Asn Trp Arg Ser Glu Leu Tyr Lys Tyr Lys Val Val Lys
545                 550                 555                 560

Ile Glu Pro Leu Gly Val Ala Pro Thr Lys Ala Lys Arg Arg Val Val
                565                 570                 575

Gln Arg Glu Lys Arg Ala Val Gly Ile Val Gly
            580                 585
```

<210> SEQ ID NO 51
<211> LENGTH: 348
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 51

```
Met Ala Gln Pro Val Gly Ile Asn Thr Ser Thr Thr Cys Cys Tyr Arg
1               5                   10                  15

Phe Ile Asn Lys Lys Ile Pro Lys Gln Arg Leu Glu Ser Tyr Arg Arg
            20                  25                  30

Thr Thr Ser Ser His Cys Pro Arg Glu Ala Val Ile Phe Lys Thr Lys
        35                  40                  45

Leu Asp Lys Glu Ile Cys Ala Asp Pro Thr Gln Lys Trp Val Gln Asp
    50                  55                  60

Phe Met Lys His Leu Asp Lys Lys Thr Gln Thr Pro Lys Leu Glu Phe
65                  70                  75                  80

Asn Asp Ala Gln Ala Pro Lys Ser Leu Asp Met Gly Leu Glu Val Gln
                85                  90                  95

Leu Leu Glu Ser Gly Gly Gly Leu Val Gln Ser Gly Gly Ser Leu Arg
            100                 105                 110

Leu Ser Cys Val Ala Ser Gly Leu Thr Phe Ser Ser Ser Ala Ile Thr
        115                 120                 125
```

```
Trp Val Arg Gln Ala Pro Gly Lys Gly Leu Glu Trp Val Ser Gly Ile
    130                 135                 140

Ser Phe Ser Gly Asp Thr Thr Tyr Tyr Ala Asp Ser Val Lys Gly Arg
145                 150                 155                 160

Phe Ser Ala Ser Arg Asp Asn Ser Lys Asn Thr Val Tyr Leu Gln Met
                165                 170                 175

Asn Asn Leu Arg Pro Asn Asp Thr Ala Val Tyr Phe Cys Ala Asn Asn
            180                 185                 190

Gln Thr Gly Asn Phe Cys Leu Asp Asn Trp Gly Gln Gly Thr Leu Val
        195                 200                 205

Thr Val Ser Ser Arg Gly Gly Gly Ser Gly Gly Gly Gly Ser Gly
    210                 215                 220

Gly Gly Gly Ser Gly Ser Gln Ser Val Leu Thr Gln Pro Pro Ser Val
225                 230                 235                 240

Ser Ala Ala Pro Gly Gln Arg Val Thr Ile Ser Cys Thr Gly Ser Arg
                245                 250                 255

Ser Asn Ile Gly Ala Gly Tyr Asp Val Asn Trp Tyr Gln Lys Phe Pro
            260                 265                 270

Glu Thr Ala Pro Lys Val Leu Ile Tyr Ser Asn Asn Asn Arg Pro Ser
        275                 280                 285

Gly Val Pro Asp Arg Phe Ser Gly Ser Lys Ser Gly Thr Ser Ala Ser
290                 295                 300

Leu Ala Ile Thr Gly Leu Gln Leu Glu Asp Glu Gly Thr Tyr Tyr Cys
305                 310                 315                 320

Gln Cys Asn Asp Asp Ser Leu Ser Gly Trp Leu Phe Gly Gly Gly Thr
                325                 330                 335

Lys Leu Thr Val Leu Arg His His His His His His
            340                 345

<210> SEQ ID NO 52
<211> LENGTH: 601
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 52

Met Ala Gln Pro Val Gly Ile Asn Thr Ser Thr Thr Cys Cys Tyr Arg
1               5                   10                  15

Phe Ile Asn Lys Lys Ile Pro Lys Gln Arg Leu Glu Ser Tyr Arg Arg
            20                  25                  30

Thr Thr Ser Ser His Cys Pro Arg Glu Ala Val Ile Phe Lys Thr Lys
        35                  40                  45

Leu Asp Lys Glu Ile Cys Ala Asp Pro Thr Gln Lys Trp Val Gln Asp
    50                  55                  60

Phe Met Lys His Leu Asp Lys Lys Thr Gln Thr Pro Lys Leu Glu Phe
65                  70                  75                  80

Asn Asp Ala Gln Ala Pro Lys Ser Leu Asp Met Gly Leu Glu Ala Ala
                85                  90                  95

Glu Asn Leu Trp Val Thr Val Tyr Tyr Gly Val Pro Val Trp Lys Glu
            100                 105                 110

Ala Thr Thr Thr Leu Phe Cys Ala Ser Asp Ala Lys Ala Tyr Glu Thr
        115                 120                 125

Glu Val His Asn Val Trp Ala Thr His Ala Cys Val Pro Thr Asp Pro
```

```
                 130                 135                 140
Asn Pro Gln Glu Val Leu Leu Glu Asn Val Thr Glu Asn Phe Asn Met
145                 150                 155                 160
Trp Lys Asn Asn Met Val Glu Gln Met Gln Glu Asp Ile Ile Ser Leu
                165                 170                 175
Trp Asp Gln Ser Leu Lys Pro Cys Val Lys Leu Thr Pro Leu Cys Val
                180                 185                 190
Thr Leu Glu Cys His Asp Val Asn Val Asn Gly Thr Ala Asn Asn Gly
                195                 200                 205
Thr Thr Asn Val Thr Glu Ser Gly Val Asn Ser Ser Asp Val Thr Ser
                210                 215                 220
Asn Asn Val Thr Asn Ser Asn Trp Gly Thr Met Glu Lys Gly Glu Ile
225                 230                 235                 240
Lys Asn Cys Ser Phe Asn Ile Thr Thr Asn Ile Arg Asp Lys Met Gln
                245                 250                 255
Lys Glu Thr Ala Gln Phe Tyr Lys Leu Asp Ile Val Pro Ile Glu Asp
                260                 265                 270
Gln Asn Lys Thr Asn Asn Thr Leu Tyr Arg Leu Ile Asn Cys Asn Thr
                275                 280                 285
Ser Val Ile Thr Gln Ala Cys Pro Lys Val Ser Phe Glu Pro Ile Pro
                290                 295                 300
Ile His Tyr Cys Thr Pro Ala Gly Phe Ala Ile Leu Lys Cys Asn Asp
305                 310                 315                 320
Arg Asn Phe Asn Gly Thr Gly Pro Cys Lys Asn Val Ser Thr Val Gln
                325                 330                 335
Cys Thr His Gly Ile Lys Pro Val Val Ser Thr Gln Leu Leu Leu Asn
                340                 345                 350
Gly Ser Leu Ala Glu Ala Glu Val Val Ile Arg Ser Glu Asn Phe Thr
                355                 360                 365
Asn Asn Ala Lys Thr Ile Ile Ile Gln Leu Asn Glu Thr Val Glu Ile
                370                 375                 380
Asn Cys Thr Arg Pro Asn Asn Asn Thr Ser Lys Arg Ile Ser Ile Gly
385                 390                 395                 400
Pro Gly Arg Ala Phe Arg Ala Thr Lys Ile Ile Gly Asn Ile Arg Gln
                405                 410                 415
Ala His Cys Asn Ile Ser Arg Ala Thr Trp Asn Ser Thr Leu Lys Lys
                420                 425                 430
Ile Val Ala Lys Leu Arg Glu Gln Phe Gly Asn Lys Thr Ile Val Phe
                435                 440                 445
Gln Pro Ser Ser Gly Gly Asp Pro Glu Ile Val Met His Ser Phe Asn
                450                 455                 460
Cys Gly Gly Glu Phe Phe Tyr Cys Asn Thr Thr Gln Leu Phe Asn Ser
465                 470                 475                 480
Thr Trp Asn Ser Thr Glu Glu Ser Asn Ser Thr Glu Glu Gly Thr Ile
                485                 490                 495
Thr Leu Pro Cys Arg Ile Lys Gln Ile Ile Asn Met Trp Gln Glu Val
                500                 505                 510
Gly Lys Ala Met Tyr Ala Pro Pro Ile Glu Gly Gln Ile Arg Cys Ser
                515                 520                 525
Ser Asn Ile Thr Gly Leu Leu Leu Thr Arg Asp Gly Gly Asn Asn Asn
                530                 535                 540
Lys Thr Asn Gly Thr Glu Ile Phe Arg Pro Gly Gly Asp Met Arg
545                 550                 555                 560
```

```
Asp Asn Trp Arg Ser Glu Leu Tyr Lys Tyr Lys Val Lys Ile Glu
                565                 570                 575

Pro Leu Gly Val Ala Pro Thr Lys Ala Lys Arg Arg Val Gln Arg
            580                 585                 590

Glu Lys Arg Ala Val Gly Ile Val Gly
        595                 600

<210> SEQ ID NO 53
<211> LENGTH: 334
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 53

Met Gly Pro Tyr Gly Ala Asn Met Glu Asp Ser Val Cys Cys Arg Asp
 1               5                  10                  15

Tyr Val Arg Tyr Arg Leu Pro Leu Arg Val Val Lys His Phe Tyr Trp
            20                  25                  30

Thr Ser Asp Ser Cys Pro Arg Pro Gly Val Val Leu Leu Thr Phe Arg
        35                  40                  45

Asp Lys Glu Ile Cys Ala Asp Pro Arg Val Pro Trp Val Lys Met Ile
    50                  55                  60

Leu Asn Lys Leu Ser Gln Asn Asp Ala Gln Ala Pro Lys Ser Leu Glu
65                  70                  75                  80

Val Gln Leu Leu Glu Ser Gly Gly Leu Val Gln Ser Gly Gly Ser
                85                  90                  95

Leu Arg Leu Ser Cys Val Ala Ser Gly Leu Thr Phe Ser Ser Ala
                100                 105                 110

Ile Thr Trp Val Arg Gln Ala Pro Gly Lys Gly Leu Glu Trp Val Ser
                115                 120                 125

Gly Ile Ser Phe Ser Gly Asp Thr Thr Tyr Tyr Ala Asp Ser Val Lys
    130                 135                 140

Gly Arg Phe Ser Ala Ser Arg Asp Asn Ser Lys Asn Thr Val Tyr Leu
145                 150                 155                 160

Gln Met Asn Asn Leu Arg Pro Asn Asp Thr Ala Val Tyr Phe Cys Ala
                165                 170                 175

Asn Asn Gln Thr Gly Asn Phe Cys Leu Asp Asn Trp Gly Gln Gly Thr
            180                 185                 190

Leu Val Thr Val Ser Ser Arg Gly Gly Gly Ser Gly Gly Gly Gly
            195                 200                 205

Ser Gly Gly Gly Ser Gly Ser Gln Ser Val Leu Thr Gln Pro Pro
    210                 215                 220

Ser Val Ser Ala Ala Pro Gly Gln Arg Val Thr Ile Ser Cys Thr Gly
225                 230                 235                 240

Ser Arg Ser Asn Ile Gly Ala Gly Tyr Asp Val Asn Trp Tyr Gln Lys
                245                 250                 255

Phe Pro Glu Thr Ala Pro Lys Val Leu Ile Tyr Ser Asn Asn Asn Arg
                260                 265                 270

Pro Ser Gly Val Pro Asp Arg Phe Ser Gly Ser Lys Ser Gly Thr Ser
            275                 280                 285

Ala Ser Leu Ala Ile Thr Gly Leu Gln Leu Glu Asp Glu Gly Thr Tyr
        290                 295                 300

Tyr Cys Gln Cys Asn Asp Asp Ser Leu Ser Gly Trp Leu Phe Gly Gly
```

```
305                 310                 315                 320
Gly Thr Lys Leu Thr Val Leu Arg His His His His His
                325                 330
```

<210> SEQ ID NO 54
<211> LENGTH: 177
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 54

```
Met Asp Gly Lys Pro Val Ser Leu Ser Tyr Arg Cys Pro Cys Arg Phe
 1               5                  10                  15

Phe Glu Ser His Val Ala Arg Ala Asn Val Lys His Leu Lys Ile Leu
                20                  25                  30

Asn Thr Pro Asn Cys Ala Leu Gln Ile Val Ala Arg Leu Lys Asn Asn
            35                  40                  45

Asn Arg Gln Val Cys Ile Asp Pro Lys Leu Lys Trp Ile Gln Glu Tyr
        50                  55                  60

Leu Glu Lys Ala Leu Asn Lys Arg Phe Lys Met Asn Asp Ala Gln Ala
65                  70                  75                  80

Pro Lys Ser Leu Asp Gly Val Thr Ser Ala Pro Asp Thr Arg Pro Ala
                85                  90                  95

Pro Gly Ser Thr Ala Pro Pro Ala His Ala Asn Ser Pro Asp Thr Arg
            100                 105                 110

Pro Ala Pro Gly Ser Thr Ala Pro Pro Ala His Gly Val Thr Ser Ala
        115                 120                 125

Ala Leu Asp Gly Val Thr Ser Ala Pro Asp Thr Arg Pro Ala Pro Gly
    130                 135                 140

Ser Thr Ala Pro Pro Ala His Ala Asn Ser Pro Asp Thr Arg Pro Ala
145                 150                 155                 160

Pro Gly Ser Thr Ala Pro Pro Ala His Gly Val Thr Ser Ala Ala Leu
                165                 170                 175

Glu
```

<210> SEQ ID NO 55
<211> LENGTH: 339
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 55

```
Met Asp Gly Lys Pro Val Ser Leu Ser Tyr Arg Cys Pro Cys Arg Phe
 1               5                  10                  15

Phe Glu Ser His Val Ala Arg Ala Asn Val Lys His Leu Lys Ile Leu
                20                  25                  30

Asn Thr Pro Asn Cys Ala Leu Gln Ile Val Ala Arg Leu Lys Asn Asn
            35                  40                  45

Asn Arg Gln Val Cys Ile Asp Pro Lys Leu Lys Trp Ile Gln Glu Tyr
        50                  55                  60

Leu Glu Lys Ala Leu Asn Lys Arg Phe Lys Met Asn Asp Ala Gln Ala
65                  70                  75                  80

Pro Lys Ser Leu Glu Val Gln Leu Leu Glu Ser Gly Gly Gly Leu Val
                85                  90                  95
```

-continued

Gln Ser Gly Gly Ser Leu Arg Leu Ser Cys Val Ala Ser Gly Leu Thr
                100                 105                 110

Phe Ser Ser Ser Ala Ile Thr Trp Val Arg Gln Ala Pro Gly Lys Gly
            115                 120                 125

Leu Glu Trp Val Ser Gly Ile Ser Phe Ser Gly Asp Thr Thr Tyr Tyr
        130                 135                 140

Ala Asp Ser Val Lys Gly Arg Phe Ser Ala Ser Arg Asp Asn Ser Lys
145                 150                 155                 160

Asn Thr Val Tyr Leu Gln Met Asn Asn Leu Arg Pro Asn Asp Thr Ala
                165                 170                 175

Val Tyr Phe Cys Ala Asn Asn Gln Thr Gly Asn Phe Cys Leu Asp Asn
            180                 185                 190

Trp Gly Gln Gly Thr Leu Val Thr Val Ser Ser Arg Gly Gly Gly Gly
        195                 200                 205

Ser Gly Gly Gly Gly Ser Gly Gly Gly Ser Gly Ser Gln Ser Val
210                 215                 220

Leu Thr Gln Pro Pro Ser Val Ser Ala Ala Pro Gly Gln Arg Val Thr
225                 230                 235                 240

Ile Ser Cys Thr Gly Ser Arg Ser Asn Ile Gly Ala Gly Tyr Asp Val
                245                 250                 255

Asn Trp Tyr Gln Lys Phe Pro Glu Thr Ala Pro Lys Val Leu Ile Tyr
                260                 265                 270

Ser Asn Asn Asn Arg Pro Ser Gly Val Pro Asp Arg Phe Ser Gly Ser
            275                 280                 285

Lys Ser Gly Thr Ser Ala Ser Leu Ala Ile Thr Gly Leu Gln Leu Glu
        290                 295                 300

Asp Glu Gly Thr Tyr Tyr Cys Gln Cys Asn Asp Asp Ser Leu Ser Gly
305                 310                 315                 320

Trp Leu Phe Gly Gly Gly Thr Lys Leu Thr Val Leu Arg His His His
                325                 330                 335

His His His

<210> SEQ ID NO 56
<211> LENGTH: 595
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 56

Met Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Met Ser Lys Arg Ser Pro Asn Asp
65                  70                  75                  80

Ala Gln Ala Pro Lys Ser Leu Glu Ala Ala Glu Asn Leu Trp Val Thr
                85                  90                  95

Val Tyr Tyr Gly Val Pro Val Trp Lys Glu Ala Thr Thr Thr Leu Phe
                100                 105                 110

-continued

```
Cys Ala Ser Asp Ala Lys Ala Tyr Glu Thr Glu Val His Asn Val Trp
        115                 120                 125
Ala Thr His Ala Cys Val Pro Thr Asp Pro Asn Pro Gln Glu Val Leu
130                 135                 140
Leu Glu Asn Val Thr Glu Asn Phe Asn Met Trp Lys Asn Asn Met Val
145                 150                 155                 160
Glu Gln Met Gln Glu Asp Ile Ile Ser Leu Trp Asp Gln Ser Leu Lys
                165                 170                 175
Pro Cys Val Lys Leu Thr Pro Leu Cys Val Thr Leu Glu Cys His Asp
            180                 185                 190
Val Asn Val Asn Gly Thr Ala Asn Asn Gly Thr Thr Asn Val Thr Glu
        195                 200                 205
Ser Gly Val Asn Ser Ser Asp Val Thr Ser Asn Asn Val Thr Asn Ser
    210                 215                 220
Asn Trp Gly Thr Met Glu Lys Gly Glu Ile Lys Asn Cys Ser Phe Asn
225                 230                 235                 240
Ile Thr Thr Asn Ile Arg Asp Lys Met Gln Lys Glu Thr Ala Gln Phe
                245                 250                 255
Tyr Lys Leu Asp Ile Val Pro Ile Glu Asp Gln Asn Lys Thr Asn Asn
            260                 265                 270
Thr Leu Tyr Arg Leu Ile Asn Cys Asn Thr Ser Val Ile Thr Gln Ala
        275                 280                 285
Cys Pro Lys Val Ser Phe Glu Pro Ile Pro Ile His Tyr Cys Thr Pro
    290                 295                 300
Ala Gly Phe Ala Ile Leu Lys Cys Asn Asp Arg Asn Phe Asn Gly Thr
305                 310                 315                 320
Gly Pro Cys Lys Asn Val Ser Thr Val Gln Cys Thr His Gly Ile Lys
                325                 330                 335
Pro Val Val Ser Thr Gln Leu Leu Asn Gly Ser Leu Ala Glu Ala
            340                 345                 350
Glu Val Val Ile Arg Ser Glu Asn Phe Thr Asn Asn Ala Lys Thr Ile
        355                 360                 365
Ile Ile Gln Leu Asn Glu Thr Val Glu Ile Asn Cys Thr Arg Pro Asn
370                 375                 380
Asn Asn Thr Ser Lys Arg Ile Ser Ile Gly Pro Gly Arg Ala Phe Arg
385                 390                 395                 400
Ala Thr Lys Ile Ile Gly Asn Ile Arg Gln Ala His Cys Asn Ile Ser
                405                 410                 415
Arg Ala Thr Trp Asn Ser Thr Leu Lys Lys Ile Val Ala Lys Leu Arg
            420                 425                 430
Glu Gln Phe Gly Asn Lys Thr Ile Val Phe Gln Pro Ser Ser Gly Gly
        435                 440                 445
Asp Pro Glu Ile Val Met His Ser Phe Asn Cys Gly Gly Glu Phe Phe
    450                 455                 460
Tyr Cys Asn Thr Thr Gln Leu Phe Asn Ser Thr Trp Asn Ser Thr Glu
465                 470                 475                 480
Glu Ser Asn Ser Thr Glu Glu Gly Thr Ile Thr Leu Pro Cys Arg Ile
                485                 490                 495
Lys Gln Ile Ile Asn Met Trp Gln Glu Val Gly Lys Ala Met Tyr Ala
            500                 505                 510
Pro Pro Ile Glu Gly Gln Ile Arg Cys Ser Ser Asn Ile Thr Gly Leu
        515                 520                 525
```

```
Leu Leu Thr Arg Asp Gly Gly Asn Asn Asn Lys Thr Asn Gly Thr Glu
        530             535             540

Ile Phe Arg Pro Gly Gly Gly Asp Met Arg Asp Asn Trp Arg Ser Glu
545             550             555             560

Leu Tyr Lys Tyr Lys Val Val Lys Ile Glu Pro Leu Gly Val Ala Pro
                565             570             575

Thr Lys Ala Lys Arg Arg Val Val Gln Arg Glu Lys Arg Ala Val Gly
            580             585             590

Ile Val Gly
        595

<210> SEQ ID NO 57
<211> LENGTH: 17
<212> TYPE: PRT
<213> ORGANISM: Artificial Sequence
<220> FEATURE:
<223> OTHER INFORMATION: Description of artificial sequence:
      /note=synthetic construct

<400> SEQUENCE: 57

Gly Gly Gly Gly Ser Gly Gly Gly Gly Ser Gly Gly Gly Gly Ser Gly
1               5                   10                  15

Ser
```

CHEMOKINE-TUMOR ANTIGEN FUSION PROTEINS AS CANCER VACCINES

This application claims priority to, and is a 35 U.S.C. § 371 national phase application of international application serial number PCT/US99/05345, filed Mar. 12, 1999 (published Sep. 16, 1999 under PCT Article 21(2) in English), which claims priority to U.S. provisional application Ser. No. 60/077,745, filed Mar. 12, 1998, which prior applications are hereby incorporated herein in their entirety by reference.

BACKGROUND OF THE INVENTION

1. Field of the Invention

The present invention relates to a vaccine that treats cancer as well as a vaccine that treats or prevents human immunodeficiency virus (HIV) infection. In particular, the present invention provides a fusion polypeptide comprising a chemokine and either a tumor or viral antigen which is administered as either a protein or nucleic acid vaccine to elicit an immune response effective in treating cancer or effective in treating or preventing HIV infection.

2. Background Art

Tumor cells are known to express tumor-specific antigens on the cell surface. These antigens are believed to be poorly immunogenic, largely because they represent gene products of oncogenes or other cellular genes which are normally present in the host and are therefore not clearly recognized as nonself. Although numerous investigators have tried to target immune responses against epitopes from various tumor specific antigens, none have been successful in eliciting adequate tumor immunity in vivo (71).

Humans are particularly vulnerable to cancer as a result of an ineffective immunogenic response (72). In fact, the poor immunogenicity of relevant cancer antigens has proven to be the single greatest obstacle to successful immunotherapy with tumor vaccines (73). Over the past 30 years, literally thousands of patients have been administered tumor cell antigens as vaccine preparations, but the results of these trials have demonstrated that tumor cell immunization has failed to provide a rational basis for the design or construction of effective vaccines. Even where patients express tumor-specific antibodies or cytotoxic T-cells, this immune response does not correlate with a suppression of the associated disease. This failure of the immune system to protect the host may be due to expression of tumor antigens that are poorly immunogenic or to heterologous expression of specific antigens by various tumor cells. The appropriate presentation of tumor antigens in order to elicit an immune response effective in inhibiting tumor growth remains a central issue in the development of an effective cancer vaccine.

Chemokines are a group of usually small secreted proteins (7–15 kDa) induced by inflammatory stimuli and are involved in orchestrating the selective migration, diapedesis and activation of blood-born leukocytes that mediate the inflammatory response (23,26). Chemokines mediate their function through interaction with specific cell surface receptor proteins (23). At least four chemokine subfamilies have been identified as defined by a cysteine signature motif, termed CC, CXC, C and $CX_3C$, where C is a cysteine and X is any amino acid residue. Structural studies have revealed that at least both CXC and CC chemokines share very similar tertiary structure (monomer), but different quaternary structure (dimer) (120–124). For the most part, conformational differences are localized to sections of loop or the N-terminus.

Monocyte chemotactic protein-3 (MCP-3) is a potent chemoattractant of monocytes and dendritic cells, T lymphocytes, basophils and eosinophils (10, 23, 26, 37).

There remains a great need for a method of presenting tumor antigens, which are known to be poorly immunogenic, "self" antigens to a subject's immune system in a manner that elicits an immune response powerful enough to inhibit the growth of tumor cells in the subject. This invention overcomes the previous limitations and shortcomings in the art by providing a fusion protein comprising a chemokine and a tumor antigen which can produce an in vivo immune response, resulting in the inhibition of tumor cells. This invention also overcomes previous shortcomings in the field of HIV vaccine development by providing a fusion protein comprising a chemokine and an HIV antigen which is effective as a vaccine for treating or preventing HIV infection.

SUMMARY OF THE INVENTION

The present invention provides a fusion polypeptide comprising human monocyte chemotactic protein-3 and human Muc-1, a fusion polypeptide comprising human interferon-induced protein 10 and human Muc-1, a fusion polypeptide comprising human macrophage-derived chemokine and human Muc-1 and a fusion polypeptide comprising human SDF-1 and human Muc-1.

The present invention also provides a fusion polypeptide comprising a human chemokine and a human immunodeficiency virus (HIV) antigen, wherein the chemokine can be IP-10, MCP-1, MCP-2, MCP-3, MCP-4, MIP 1, RANTES, SDF-1, MIG and/or MDC and wherein the HIV antigen can be gp120, gp160, gp41, an active fragment of gp120, an active fragment of gp160 and/or an active fragment of gp41.

In addition, the present invention provides a method of producing an immune response in a subject, comprising administering to the subject any of the fusion polypeptides of this invention, comprising a chemokine and a human immunodeficiency virus (HIV) antigen, or a chemokine and a tumor antigen, either as a protein or a nucleic acid encoding the fusion polypeptide.

Also provided is a method of treating a cancer in a subject comprising adminstering to the subject any of the fusion polypeptides of this invention, comprising a chemokine and a tumor antigen, either as a protein or a nucleic acid encoding the fusion polypeptide.

Further provided is a method of treating or preventing HIV infection in a subject, comprising administering to the subject any of the fusion polypeptides of this invention, comprising a chemokine and a human immunodeficiency virus (HIV) antigen, either as a protein or a nucleic acid encoding the fusion polypeptide.

A method of treating a B cell tumor in a subject is also provided, comprising administering to the subject a fusion polypeptide comprising a human chemokine and a B cell tumor antigen.

Various other objectives and advantages of the present invention will become apparent from the following detailed description.

DESCRIPTION OF THE PREFERRED EMBODIMENTS

As used in the claims, "a" can include multiples. For example, "a cell" can mean a single cell or more than one cell.

The present invention is based on the unexpected discovery that the administration of a fusion protein comprising a chemokine and a tumor antigen or administration of a nucleic acid encoding a fusion protein comprising a chemokine and a tumor antigen yields an effective and specific anti-tumor immune response by converting a "self" tumor antigen into a potent immunogen by binding to a chemokine moiety. A further unexpected discovery of the present invention is that the chemokine-scFv fusion polypeptide of this invention is superior to the prototype Id-KLH vaccine in tumor protection studies as described herein.

Thus, the present invention provides a fusion polypeptide comprising a chemokine and a tumor antigen. The fusion polypeptide can be present in a purified form and can induce an immune response against the tumor antigen and inhibit the growth of tumor cells expressing the tumor antigen. "Purified" as used herein means the polypeptide is sufficiently free of contaminants or cell components with which proteins normally occur to allow the peptide to be used therapeutically. It is not contemplated that "purified" necessitates having a preparation that is technically totally pure (homogeneous), but purified as used herein means the fusion polypeptide is sufficiently pure to provide the polypeptide in a state where it can be used therapeutically. As used herein, "fusion polypeptide" means a polypeptide made up of two or more amino acid sequences representing peptides or polypeptides from different sources. Also as used herein, "epitope" refers to a specific amino acid sequence of limited length which, when present in the proper conformation, provides a reactive site for an antibody or T cell receptor. The identification of epitopes on antigens can be carried out by immunology protocols that are standard in the art (74). As further used herein, "tumor antigen" describes a polypeptide expressed on the cell surface of specific tumor cells and which can serve to identify the type of tumor. An epitope of the tumor antigen can be any site on the antigen that is reactive with an antibody or T cell receptor.

As used herein, "chemokine" means a small secreted protein, induced by inflammatory stimuli (e.g., fibroblasts, endothelial cells, epithelial cells, monocytes, macrophages, T cells, B cells, PMNs, etc. stimulated by proinflammatory cytokines such as interferon-gamma, interleukin 4, products of Th1 and Th2 lymphocytes, interleukin-1, tumor necrosis factor-alpha and bacterial products such as lipopolysaccharide, as well as viral infection (75,76), which orchestrates a chemotactic response typically after binding to specific G-protein-coupled cell surface receptors on target cells (e.g., antigen presenting cells (APC), such as dendritic cells, monocytes, macrophages, keratinocytes and B cells), comprising the selective migration, diapedesis and activation of leukocytes which mediate the inflammatory response. Four human CXC chemokine receptors (CXCR1–CXCR4), eight human CC chemokine receptors (CCR1–CCR8) and one CXXXC chemokine receptor ($CX_3CR1$) have been identified. As one example, the chemokine, interferon-induced protein 10 (IP-10) binds to the CXCR3 receptor, thus inducing chemotaxis of activated T cells, NK cells, etc., which express this receptor. As another example, the chemokine monocyte chemotactic protein-3 (MCP-3) acts via binding to the CCR1, CCR2 and CCR3 chemokine receptors on antigen presenting cells (APC) such as dendritic cells, eosinophils, basophils, monocytes and activated T cells. Thus, MCP-3 selectively targets and induces chemotaxis of these cell types.

The chemokine of this invention can include, but is not limited to, interferon-induced protein 10, monocyte chemotactic protein-3, monocyte chemotactic protein-2, monocyte chemotactic protein-1, monocyte chemotactic protein-4, macrophage inflammatory protein 1, RANTES, SDF-1, MIG and macrophage-derived chemokine, as well as any other chemokine now known or later identified.

It will be appreciated by one of skill in the art that chemokines can include active fragments of chemokines which retain the chemotactic activity of the intact molecule. For example, for both CC and CXC chemokines, the N terminal region is the critical region of the molecule for biological activity and leukocyte selectivity. In particular, the N-terminal ELR motif-containing CXC chemokines are chemotactic for neutrophils, whereas those not containing the motif act on lymphocytes. IP-10 and MIG, for example, do not contain the ELR motif and are known to attract activated T cells (77). Addition of a single amino acid residue to the amino terminus of MCP-1 decreases its biological activity up to 1000 fold and deletion of a single amino acid for that region converts the chemokine from an activator of basophils to an eosinophil chemoattractant (78).

A chemokine consists of two structural portions: the amino terminal portion and the carboxy terminal portion. The amino terminal portion is responsible for chemokine receptor binding and the carboxy terminal end binds to heparin and heparan sulfate, for example, in the extracellular matrix and on the surface of endothelial cells. The chemokine gene can be fragmented as desired and the fragments can be fused to a specific marker gene encoding an antigen (e.g., Muc-1 VNT, lymphoma scFv, etc.). The fusion polypeptide comprising the chemokine fragment and the tumor or viral antigen can be produced and purified as described herein and tested for immunogenicity according to the methods provided herein. By producing several fusion polypeptides having chemokine fragments of varying size, the minimal size chemokine fragment which impart an immunological effect can be identified.

The tumor antigen moiety of the fusion polypeptide of this invention can be any tumor antigen now known or later identified as a tumor antigen. The appropriate tumor antigen used in the fusion polypeptide naturally depends on the tumor type being treated. For example, the tumor antigen can be, but is not limited to human epithelial cell mucin (Muc-1; a 20 amino acid core repeat for Muc-1 glycoprotein, present on breast cancer cells and pancreatic cancer cells), the Ha-ras oncogene product, p53, carcino-embryonic antigen (CEA), the raf oncogene product, GD2, GD3, GM2, TF, sTn, MAGE-1, MAGE-3, tyrosinase, gp75, Melan-A/Mart-1, gp100, HER2/neu, EBV-LMP 1 & 2, HPV-F4, 6, 7, prostatic serum antigen (PSA), alpha-fetoprotein (AFP), CO17-1A, GA733, gp72, p53, the ras oncogene product, HPV E7 and melanoma gangliosides, as well as any other tumor antigens now known or identified in the future. Tumor antigens can be obtained following known procedures or are commercially available (79). The effectiveness of the fusion protein in eliciting an immune response against a particular tumor antigen can be determined according to methods standard in the art for determining the efficacy of vaccines and according to the methods set forth in the Examples.

Additionally, the tumor antigen of the present invention can be an antibody which can be produced by a B cell tumor (e.g., B cell lymphoma; B cell leukemia; myeloma) or the tumor antigen can be a fragment of such an antibody, which contains an epitope of the idiotype of the antibody. The epitope fragment can comprise as few as nine amino acids. For example, the tumor antigen of this invention can be a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR.

In a preferred embodiment, the tumor antigen of this invention can be a single chain antibody (scFv), comprising linked $V_H$, and $V_L$ domains and which retains the conformation and specific binding activity of the native idiotype of the antibody (27). Such single chain antibodies are well known in the art and can be produced by standard methods and as described in the Examples herein.

In addition, the tumor antigen of the present invention can be an epitope of the idiotype of a T cell receptor, which can be produced by a T cell tumor (e.g., T cell lymphoma; T cell leukemia; myeloma). The epitope can comprise as few as nine amino acids.

As will be appreciated by those skilled in the art, the invention also includes peptides and polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff et al. (80). These modifications can result in changes in the amino acid sequence, provide silent mutations, modify a restriction site, or provide other specific mutations. The fusion polypeptides can comprise one or more selected epitopes on the same tumor antigen, one or more selected epitopes on different tumor antigens, as well as repeats of the same epitope, either in tandem or interspersed along the amino acid sequence of the fusion polypeptide. The tumor antigen can be positioned in the fusion polypeptide at the carboxy terminus of the chemokine, the amino terminus of chemokine and/or at one or more internal sites within the chemokine amino acid sequence.

The present invention further provides a polypeptide having the amino acid sequence selected from the group consisting of SEQ ID NO:13 (human IP-10 fused to murine scFv38), SEQ ID NO:16 (human MCP-3 fused to murine scFv38), SEQ ID NO:12 (human IP-10 fused to murine scFv20A), SEQ ID NO:14 (human MCP-3 fused to murine scFv20A) SEQ ID NO:1 (human IP-10 fused to human Muc-1 core epitope (VNT)), SEQ ID NO:2 (human MCP-3 fused to human Muc-1 core epitope (VNT)), SEQ ID NO:3 (murine IP-10 fused to human Muc-1 core epitope (VNT)), SEQ ID NO:4 (murine MCP-3 fused to Muc-1 core epitope (VNT)), SEQ ID NO:5 (human SDF-1β fused to the hypervariable region of the envelope glycoprotein, gp120, of HIV-1 (the disulfate loop V3)), SEQ ID NO:6 (human IP-10 fused to the hypervariable region of the envelope glycoprotein gp120 of HIV-1 (the disulfate loop V3), SEQ ID NO:7 (human MCP-3 fused to the hypervariable region of the envelope glycoprotein gp120 of HIV-1 (the disulfate loop V3), SEQ ID NO:8 (murine IP-10 fused to the hypervariable region of the envelope glycoprotein gp120 of HIV-1 (the disulfate loop V3), SEQ ID NO:52 (human IP-10 fused with HIV gp120), SEQ ID NO:56 (human MCP-3 fused with HIV gp120), and SEQ ID NO:9 (murine MCP-3 fused to the hypervariable region of the envelope glycoprotein gp120 of HIV-1 (the disulfate loop V3). It would be routine for an artisan to produce a fusion protein comprising any human chemokine region and any human tumor antigen (e.g., human single chain antibody) region according to the methods described herein, on the basis of the availability in the art of the nucleic acid and/or amino acid sequence of the human chemokine of interest and the human tumor antigen of interest.

The present invention further provides a fusion polypeptide comprising a first region comprising a chemokine selected from the group consisting of interferon-induced protein 10, monocyte chemotactic protein-2, monocyte chemotactic protein-1, macrophage inflammatory protein 1, RANTES, SDF-1 and macrophage-derived chemokine and a second region comprising a tumor antigen selected from the group consisting of human epithelial cell mucin (Muc-1), the Ha-ras oncogene product, p53, carcino-embryonic antigen (CEA), the raf oncogene product, GD2, GD3, GM2, TF, sTn, MAGE-1, MAGE-3, tyrosinase, gp75, Melan-A/Mart-1, gp100, HER2/neu, EBV-LMP 1 & 2, HPV-F4, 6, 7, prostatic serum antigen (PSA), alpha-fetoprotein (AFP), CO17-1A, GA733, gp72, p53, the ras oncogene product, HPV E7, melanoma gangliosides, an antibody produced by a B cell tumor (e.g., B cell lymphoma; B cell leukemia; myeloma), a fragment of such an antibody, which contains an epitope of the idiotype of the antibody, a malignant B cell antigen receptor, a malignant B cell immunoglobulin idiotype, a variable region of an immunoglobulin, a hypervariable region or CDR of a variable region of an immunoglobulin, a malignant T cell receptor (TCR), a variable region of a TCR and/or a hypervariable region of a TCR.

For example, the present invention provides a fusion polypeptide comprising an scFv cloned from a human subject's biopsy tumor material or from a hybridoma cell line producing a lymphoma antibody and a human chemokine moiety (e.g., MCP-3, IP-10, SDF-1, etc.). In addition, the present invention provides a human chemokine fused with the Muc-1 core epitope of human breast cancer or human pancreatic cancer. Muc-1 is a glycoprotein (Mr>200,000) abundantly expressed on breast cancer cells and pancreatic tumor cells. A variable number of tandem (VNT) repeats of a 20 amino acid peptide (PDTRPAPGSTAPPAHGVTSA; SEQ ID NO:40) include B and T cell epitopes. Thus, the present invention provides a fusion protein comprising IP-10 and Muc-1 VNT and MCP-3 and Muc-1 VNT. The expression vector is designed so that a VNT can be changed by routine cloning methods to produce a fusion polypeptide comprising IP-10 or MCP-3 fused with a Muc-1 VNT dimer, trimer, tetramer, pentamer, hexamer, etc.

In specific emobodiments, the present invention also provides a fusion polypeptide comprising human monocyte chemotactic protein-3 and human Muc-1, a fusion polypeptide comprising human interferon-induced protein 10 and human Muc-1, a fusion polypeptide comprising human macrophage-derived chemokine and human Muc-1, a fusion polypeptide comprising human SDF-1 and human Muc-1, a fusion polypeptide comprising the amino acid sequence of SEQ ID NO:2, a fusion polypeptide comprising the amino acid sequence of SEQ ID NO:1, a fusion polypeptide comprising the amino acid sequence of SEQ ID NO:49 (human MDC fused to human Muc-1) and a fusion polypeptide comprising the amino acid sequence of SEQ ID NO:54 (human SDF1 fused to human Muc-1).

The present invention further provides a fusion polypeptide comprising a human chemokine (e.g., IP-10, MCP-3, SDF-1, etc.) and a scFv which recognizes tumor antigens, such as idiotype-specific scFv, Muc-1, etc. Such a fusion polypeptide would allow migration, recruitment and activation of specialized cells of the immune system, such as natural killer (NK) cells, macrophages, dendritic cells (DC), polymorphonuclear (PMN) leukocytes, cytotoxic lymphocytes (CTL), etc., which would destroy the target cell.

The fusion polypeptide of this invention can further comprise a spacer sequence between the chemokine and the tumor antigen or viral antigen, which can have the amino acid sequence EFNDAQAPKSLE (SEQ ID NO:11), which allows for retention of the correct folding of the tumor antigen region of the polypeptide.

In addition, the present invention provides a composition comprising the fusion polypeptide of this invention and a suitable adjuvant. Such a composition can be in a pharmaceutically acceptable carrier, as described herein. As used herein, "suitable adjuvant" describes a substance capable of being combined with the fusion polypeptide to enhance an immune response in a subject without deleterious effect on the subject. A suitable adjuvant can be, but is not limited to, for example, an immunostimulatory cytokine, SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion. The adjuvant, such as an immunostimulatory cytokine can be administered before the administration of the fusion protein or nucleic acid encoding the fusion protein, concurrent with the administration of the fusion protein or nucleic acid or up to five days after the administration of the fusion polypeptide or nucleic acid to a subject. QS-21, similarly to alum, complete Freund's adjuvant, SAF, etc., can be administered within hours of administration of the fusion protein.

Furthermore, combinations of adjuvants, such as immunostimulatory cytokines can be co-administered to the subject before, after or concurrent with the administration of the fusion polypeptide or nucleic acid. For example, combinations of adjuvants, such as immunostimulatory cytokines, can consist of two or more of immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants may be determined by measuring the immune response directed against the fusion polypeptide with and without the adjuvant or combination of adjuvants, using standard procedures, as described herein.

Furthermore, the present invention provides a composition comprising the fusion polypeptide of this invention or a nucleic acid encoding the fusion polypeptide of this invention and an adjuvant, such as an immunostimulatory cytokine or a nucleic acid encoding an adjuvant, such as an immunostimulatory cytokine. Such a composition can be in a pharmaceutically acceptable carrier, as described herein. The immunostimulatory cytokine used in this invention can be, but is not limited to, GM/CSF, interleukin-2, interleukin-12, interferon-gamma, interleukin-4, tumor necrosis factor-alpha, interleukin-1, hematopoietic factor flt3L, CD40L, B7.1 con-stimulatory molecules and B7.2 co-stimulatory molecules.

The present invention further contemplates a fusion polypeptide comprising a chemokine, or active fragment thereof, as described herein and an antigen of human immunodeficiency virus (HIV). For example, the HIV antigen of this invention can be, but is not limited to, the envelope glycoprotein gp120, the third hypervariable region of the envelope glycoprotein, gp120 of HIV-1 (the disulfate loop V3), having the amino acid sequence: NCTRPNNNTRKR-IRIQRGPGRAFVTIGKIGNMRQAHCNIS (SEQ ID NO:10), any other antigenic fragment of gp120, the envelope glycoprotein gp160, an antigenic fragment of gp160, the envelope glycoprotein gp41 and an antigenic fragment of gp41. For example, the nucleic acid encoding the V3 loop can be fused to the 3' end of the nucleic acid encoding a chemokine (e.g., IP-10, MCP-3, SDF-1, MDC) directly or separated by a spacer sequence. The chemokine-V3 loop fusion polypeptide can be produced in an expression system as described herein and purified as also described herein.

In specific embodiments, the present invention provides a fusion polypeptide comprising a human chemokine and a human immunodeficiency virus (HIV) antigen, wherein the chemokine can be IP-10, MCP-1, MCP-2, MCP-3, MCP-4, MIP 1, RANTES, SDF-1, MIG and/or MDC and wherein the HIV antigen can be gp120, gp160, gp41, an active (i.e., antigenic) fragment of gp120, an active (i.e., antigenic) fragment of gp160 and an active (i.e., antigenic) fragment of gp41.

Further provided in this invention is fusion polypeptide comprising human IP-10 and HIV gp120, a fusion polypeptide comprising human MCP-3 and HIV gp120, a fusion polypeptide comprising human MDC and HIV gp120, a fusion polypeptide comprising human SDF-1 and HIV gp120, a fusion polypeptide comprising the amino acid sequence of SEQ ED NO:6 (human IP-10/gp120), a fusion polypeptide comprising the amino acid sequence of SEQ ID NO:7 (human MCP-3/gp120), a fusion polypeptide comprising the amino acid sequence of SEQ ID NO:5 (human SDF1/gp120), a fusion polypeptide comprising the amino acid sequence of SEQ ID NO:52, a fusion polypeptide comprising the amino acid sequence of SEQ ID NO:56 and a fusion polypeptide comprising the amino acid sequence of SEQ ID NO:50 (human MDC/gp120).

An isolated nucleic acid encoding the fusion polypeptides of this invention as described above is also provided. By "isolated nucleic acid" is meant a nucleic acid molecule that is substantially free of the other nucleic acids and other components commonly found in association with nucleic acid in a cellular environment. Separation techniques for isolating nucleic acids from cells are well known in the art and include phenol extraction followed by ethanol precipitation and rapid solubilization of cells by organic solvent or detergents (81).

The nucleic acid encoding the fusion polypeptide can be any nucleic acid that functionally encodes the fusion polypeptide. To functionally encode the polypeptide (i.e., allow the nucleic acid to be expressed), the nucleic acid can include, for example, expression control sequences, such as an origin of replication, a promoter, an enhancer and necessary information processing sites, such as ribosome binding sites, RNA splice sites, polyadenylation sites and transcriptional terminator sequences. Preferred expression control sequences are promoters derived from metallothionine genes, actin genes, immunoglobulin genes, CMV, SV40, adenovirus, bovine papilloma virus, etc. A nucleic acid encoding a selected fusion polypeptide can readily be determined based upon the genetic code for the amino acid sequence of the selected fusion polypeptide and many nucleic acids will encode any selected fusion polypeptide. Modifications in the nucleic acid sequence encoding the fusion polypeptide are also contemplated. Modifications that can be useful are modifications to the sequences controlling expression of the fusion polypeptide to make production of the fusion polypeptide inducible or repressible as controlled by the appropriate inducer or repressor. Such means are standard in the art (81). The nucleic acids can be generated by means standard in the art, such as by recombinant nucleic acid techniques, as exemplified in the examples herein and by synthetic nucleic acid synthesis or in vitro enzymatic synthesis.

A vector comprising any of the nucleic acids of the present invention and a cell comprising any of the vectors of the present invention are also provided. The vectors of the invention can be in a host (e.g., cell line or transgenic animal) that can express the fusion polypeptide contemplated by the present invention.

There are numerous $E. coli$ (*Escherichia coli*) expression vectors known to one of ordinary skill in the art useful for the expression of nucleic acid encoding proteins such as fusion proteins. Other microbial hosts suitable for use include bacilli, such as *Bacillus subtilis*, and other enterobacteria, such as Salmonella, Serratia, as well as various Pseudomonas species. These prokaryotic hosts can support expression vectors which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the protein. Also, the carboxy-terminal extension of the protein can be removed using standard oligonucleotide mutagenesis procedures.

Additionally, yeast expression can be used. There are several advantages to yeast expression systems. First, evidence exists that proteins produced in a yeast secretion system exhibit correct disulfide pairing. Second, post-translational glycosylation is efficiently carried out by yeast secretory systems. The *Saccharomyces cerevisiae* pre-pro-alpha-factor leader region (encoded by the MF α-1 gene) is routinely used to direct protein secretion from yeast (82). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage-signal sequence. The polypeptide coding sequence can be fused in-frame to the pre-pro-alpha-factor leader region. This construct is then put under the control of a strong transcription promoter, such as the alcohol dehydrogenase I promoter or a glycolytic promoter. The protein coding sequence is followed by a translation termination codon which is followed by transcription termination signals. Alternatively, the polypeptide coding sequence of interest can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Efficient post-translational glycosylation and expression of recombinant proteins can also be achieved in Baculovirus systems in insect cells.

Mammalian cells permit the expression of proteins in an environment that favors important post-translational modifications such as folding and cysteine pairing, addition of complex carbohydrate structures and secretion of active protein. Vectors useful for the expression of proteins in mammalian cells are characterized by insertion of the protein coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary (CHO) cell line using a methotrexate resistance-encoding vector. Presence of the vector RNA in transformed cells can be confirmed by Northern blot analysis and production of a cDNA or opposite strand RNA corresponding to the protein coding sequence can be confirmed by Southern and Northern blot analysis, respectively. A number of other suitable host cell lines capable of secreting intact proteins have been developed in the art and include the CHO cell lines, HeLa cells, myeloma cell lines, Jurkat cells and the like. Expression vectors for these cells can include expression control sequences, as described above.

The vectors containing the nucleic acid sequences of interest can be transferred into the host cell by well-known methods, which vary depending on the type of cell host. For example, calcium chloride transfection is commonly utilized for prokaryotic cells, whereas calcium phosphate treatment, lipofection or electroporation may be used for other cell hosts.

Alternative vectors for the expression of protein in mammalian cells, similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been positioned to ensure the functioning of an expression control sequence. These expression vectors are typically replicable in the host organisms either as episomes or as an integral part of the host chromosomal DNA. Commnonly, expression vectors can contain selection markers, e.g., tetracycline resistance or hygromycin resistance, to permit detection and/or selection of those cells transformed with the desired nucleic acid sequences (83).

Additionally, the fusion polypeptides and/or nucleic acids of the present invention can be used in in vitro diagnostic assays, as well as in screening assays for identifying unknown tumor antigen epitopes and fine mapping of tumor antigen epitopes.

Also provided is a method for producing a fusion polypeptide comprising a chemokine, or an active fragment thereof and a tumor antigen or HIV antigen, comprising cloning into an expression vector a first DNA fragment encoding a chemokine or active fragment thereof and a second DNA fragment encoding a tumor antigen or HIV antigen; and expressing the DNA of the expression vector in an expression system under conditions whereby the fusion polypeptide is produced. The expression vector and expression system can be of any of the types as described herein. The cloning of the first and second DNA segments into the expression vector and expression of the DNA under conditions which allow for the production of the fusion protein of this invention can be carried out as described in the Examples section included herein. The method of this invention can further comprise the step of isolating and purifying the fusion polypeptide, according to methods well known in the art and as described herein.

Any of the fusion polypeptides, the nucleic acids and the vectors of the present invention can be in a pharmaceutically acceptable carrier and in addition, can include other medicinal agents, pharmaceutical agents, carriers, diluents, adjuvants (e.g., immunostimulatory cytokines), etc. By "pharmaceutically acceptable" is meant a material that is not biologically or otherwise undesirable, i.e., the material may be administered to an individual along with the selected antigen without causing substantial deleterious biological effects or interacting in a deleterious manner with any of the other components of the composition in which it is contained. Actual methods of preparing such dosage forms are known, or will be apparent, to those skilled in this art (84).

Thus, the present invention provides a method for inducing an immune response in a subject capable of induction of an immune response and preferably human, comprising administering to the subject an immune response-inducing amount of the fusion polypeptide of this invention. As used herein, "an immune response-inducing amount" is that amount of fusion polypeptide which is capable of producing in a subject a humoral and/or cellular immune response capable of being detected by standard methods of measurement, such as, for example, as described herein. For example, the antigenic polypeptide region can induce an antibody response. The antibodies can treat or prevent a pathological or harmful condition in the subject in which the antibodies are produced or the antibodies can be removed from the subject and administered to another subject to treat or prevent a pathological or harmful condition. The fusion polypeptide can also induce an effector T cell (cellular) immune response which is effective in treating or preventing a pathological or harmful conditions in the subject.

In an embodiment wherein the antigen moiety of the fusion polypeptide comprises an immunoglobulin light or heavy chain or a single chain antibody, the immune response can be the production in the subject of anti-idiotype antibodies, which represent the image of the original antigen and can function in a vaccine preparation to induce an immune response to a pathogenic antigen, thereby avoiding immunization with the antigen itself (85). The anti-idiotype antibodies can treat or prevent a pathological or harmful condition in the subject in which the anti-idiotype antibodies are produced or the anti-idiotype antibodies can be removed from the subject and administered to another subject to treat or prevent a pathological or harmful condition.

Further provided is a method for inhibiting the growth of tumor cells in a subject, comprising administering to the subject a tumor cell growth-inhibiting amount of the fusion polypeptide of this invention. The subject of this method can be any subject in which a humoral and/or cellular immune response to a tumor can be induced, which is preferably an animal and most preferably a human. As used herein, "inhibiting the growth of tumor cells" means that following administration of the fusion polypeptide, a measurable humoral and/or cellular immune response against the tumor cell epitope is elicited in the subject, resulting in the inhibition of growth of tumor cells present in the subject. The humoral immune response can be measured by detection, in the serum of the subject, of antibodies reactive with the epitope of the tumor antigen present on the fusion polypeptide, according to protocols standard in the art, such as enzyme linked immunosorbent immunoassay (ELISA) and Western blotting protocols. The cellular immune response can be measured by, for example, footpad swelling in laboratory animals, peripheral blood lymphocyte (PBL) proliferation assays and PBL cytotoxicity assays, as would be known to one of ordinary skill in the art of immunology and particularly as set forth in the available handbooks and texts of immunology protocols (86).

The present invention also provides a method of treating cancer in a subject diagnosed with cancer, comprising administering to the subject an effective amount of the fusion polypeptide of the present invention. The cancer can be, but is not limited to B cell lymphoma, T cell lymphoma, myeloma, leukemia, breast cancer, pancreatic cancer, colon cancer, lung cancer, renal cancer, liver cancer, prostate cancer, melanoma and cervical cancer.

Further provided is a method of treating a B cell tumor in a subject diagnosed with a B cell tumor, comprising administering an effective amount of the fusion polypeptide of this invention, which comprises an antibody or a fragment thereof, as described herein, in a pharmaceutically acceptable carrier, to the subject.

In specific embodiments, the present invention also provides a method of producing an immune response in a subject, comprising administering to the subject a composition comprising a fusion polypeptide of this invention and a pharmaceutically acceptable carrier and wherein the fusion polypeptide can be a fusion polypeptide comprising human monocyte chemotactic protein-3 and human Muc-1, a fusion polypeptide comprising human interferon-induced protein 10 and human Muc-1, a fusion polypeptide comprising human macrophage-derived chemokine and human Muc-1, a fusion polypeptide comprising human SDF-1 and human Muc-1, a fusion polypeptide comprising the amino acid sequence of SEQ ID NO:2, a fusion polypeptide comprising the amino acid sequence of SEQ ID NO:1, a fusion polypeptide comprising the amino acid sequence of SEQ ID NO:49 and a fusion polypeptide comprising the amino acid sequence of SEQ ID NO:54, thereby producing an immune response in the subject.

Also provided is a method of producing an immune response in a subject, comprising administering to the subject a composition comprising a nucleic acid encoding a fusion polypeptide of this invention and a pharmaceutically acceptable carrier and wherein the fusion polypeptide is a fusion polypeptide comprising comprising human monocyte chemotactic protein-3 and human Muc-1, a fusion polypeptide comprising human interferon-induced protein 10 and human Muc-1, a fusion polypeptide comprising human macrophage-derived chemokine and human Muc-1, a fusion polypeptide comprising human SDF-1 and human Muc-1, a fusion polypeptide comprising the amino acid sequence of SEQ ID NO:2, a fusion polypeptide comprising the amino acid sequence of SEQ ID NO:1, a fusion polypeptide comprising the amino acid sequence of SEQ ID NO:49 and a fusion polypeptide comprising the amino acid sequence of SEQ ID NO:54, under conditions whereby the nucleic acid of the composition can be expressed, thereby producing an immune response in the subject.

In further embodiments, the present invention also provides a method of producing an immune response in a subject, comprising administering to the subject a composition comprising a fusion polypeptide of this invention and a pharmaceutically acceptable carrier and wherein the fusion polypeptide can be a fusion polypeptide comprising human IP-10 and HIV gp120, a fusion polypeptide comprising human MCP-3 and HIV gp120, a fusion polypeptide comprising human MDC and HIV gp120, a fusion polypeptide comprising human SDF-1 and HIV gp120, a fusion polypeptide comprising the amino acid sequence of SEQ ID NO:6, a fusion polypeptide comprising the amino acid sequence of SEQ ID NO:7, a fusion polypeptide comprising the amino acid sequence of SEQ ID NO:52, a fusion polypeptide comprising the amino acid sequence of SEQ ID NO:56, a fusion polypeptide comprising the amino acid sequence of SEQ ID NO:5, and/or a fusion polypeptide comprising the amino acid sequence of SEQ ID NO:50, thereby producing an immune response in the subject.

Also provided is a method of producing an immune response in a subject, comprising administering to the subject a composition comprising a nucleic acid encoding a fusion polypeptide of this invention and a pharmaceutically acceptable carrier and wherein the fusion polypeptide is a fusion polypeptide comprising human IP-10 and HIV gp120, a fusion polypeptide comprising human MCP-3 and HIV gp120, a fusion polypeptide comprising human MDC and HIV gp120, a fusion polypeptide comprising human SDF-1 and HIV gp120, a fusion polypeptide comprising the amino acid sequence of SEQ ID NO:6, a fusion polypeptide comprising the amino acid sequence of SEQ ID NO:7, a fusion polypeptide comprising the amino acid sequence of SEQ ID NO:5, a fusion polypeptide comprising the amino acid sequence of SEQ ID NO:52, a fusion polypeptide comprising the amino acid sequence of SEQ ID NO:56, and/or a fusion polypeptide comprising the amino acid sequence of SEQ ID NO:50, under conditions whereby the nucleic acid of the composition can be expressed, thereby producing an immune response in the subject.

Also provided is a method of producing an immune response in a subject, comprising administering to the subject a composition comprising a fusion polypeptide and a pharmaceutically acceptable carrier and wherein the fusion polypeptide is a fusion polypeptide comprising a human chemokine and a human immunodeficiency virus (HIV) antigen, wherein the chemokine can be IP-10, MCP-1, MCP-2, MCP-3, MCP-4, MIP 1, RANTES, SDF-1, MIG and/or MDC and wherein the HIV antigen can be gp120, gp160, gp41, an active (i.e., antigenic) fragment of gp120, an active (i.e., antigenic) fragment of gp160 and/or an active (i.e., antigenic) fragment of gp41, thereby producing an immune response in the subject.

The present invention also provides a method of producing an immune response in a subject, comprising administering to the subject a composition comprising a nucleic acid encoding a fusion polypeptide comprising a human chemokine and a human immunodeficiency virus (HIV) antigen, wherein the chemokine can be IP-10, MCP-1, MCP-2, MCP-3, MCP-4, MIP 1, RANTES, SDF-1, MIG and/or MDC and wherein the HIV antigen can be gp120, gp160, gp41, an active (i.e., antigenic) fragment of gp120, an active (i.e., antigenic) fragment of gp160 and/or an active (i.e., antigenic) fragment of gp41, and a pharmaceutically acceptable carrier, under conditions whereby the nucleic acid can be expressed, thereby producing an immune response in the subject.

In any of the methods provided herein which recite the production of an immune response, the immune response can be humoral and/or an effector T cell (cellular) immune response, as determined according to methods standard in the art.

In another embodiment, the present invention provides a method of treating a cancer in a subject comprising administering to the subject a composition comprising a fusion polypeptide of this invention and a pharmaceutically acceptable carrier and wherein the fusion polypeptide is a fusion polypeptide comprising human monocyte chemotactic protein-3 and human Muc-1, a fusion polypeptide comprising human interferon-induced protein 10 and human Muc-1, a fusion polypeptide comprising human macrophage-derived chemokine and human Muc-1, a fusion polypeptide comprising human SDF-1 and human Muc-1, a fusion polypeptide comprising the amino acid sequence of SEQ ID NO:2, a fusion polypeptide comprising the amino acid sequence of SEQ ID NO:1, a fusion polypeptide comprising the amino acid sequence of SEQ ID NO:49 and a fusion polypeptide comprising the amino acid sequence of SEQ ID NO:54, thereby treating a cancer in the subject.

Additionally provided is a method of treating a cancer in a subject, comprising administering to the subject a composition comprising a nucleic acid encoding a fusion polypeptide of this invention and a pharmaceutically acceptable carrier and wherein the fusion polypeptide is a fusion polypeptide comprising human monocyte chemotactic protein-3 and human Muc-1, a fusion polypeptide comprising human interferon-induced protein 10 and human Muc-1, a fusion polypeptide comprising human macrophage-derived chemokine and human Muc-1, a fusion polypeptide comprising human SDF-1 and human Muc-1, a fusion polypeptide comprising the amino acid sequence of SEQ ID NO:2, a fusion polypeptide comprising the amino acid sequence of SEQ ID NO:1, a fusion polypeptide comprising the amino acid sequence of SEQ ID NO:49 and a fusion polypeptide comprising the amino acid sequence of SEQ ID NO:54, under conditions whereby the nucleic acid of the composition can be expressed, thereby treating a cancer in the subject.

Further provided is a method of treating or preventing HIV infection in a subject, comprising administering to the subject a composition comprising a human chemokine and a human immunodeficiency virus (HIV) antigen, wherein the chemokine can be IP-10, MCP-1, MCP-2, MCP-3, MCP-4, MIP 1, RANTES, SDF-1, MIG and/or MDC and wherein the HIV antigen can be gp120, gp160, gp41, an active (i.e., antigenic) fragment of gp120, an active (i.e., antigenic) fragment of gp160 and/or an active (i.e., antigenic) fragment of gp41, and a pharmaceutically acceptable carrier, thereby treating or preventing HIV infection in the subject.

In addition, a method of treating or preventing HIV infection in a subject is provided herein, comprising administering to the subject a composition comprising a nucleic acid encoding a fusion polypeptide comprising a human chemokine and a human immunodeficiency virus (HIV) antigen, wherein the chemokine can be IP-10, MCP-1, MCP-2, MCP-3, MCP-4, MIP 1, RANTES, SDF-1, MIG and/or MDC and wherein the HIV antigen can be gp120, gp160, gp41, an active (i.e., antigenic) fragment of gp120, an active (i.e., antigenic) fragment of gp160 and/or an active (i.e., antigenic) fragment of gp41, and a pharmaceutically acceptable carrier, under conditions whereby the nucleic acid can be expressed, thereby treating or preventing HIV infection in the subject.

Further provided is a method of treating or preventing HIV infection in a subject, comprising administering to the subject a composition comprising a fusion polypeptide comprising human IP-10 and HIV gp120, a fusion polypeptide comprising human MCP-3 and HIV gp120, a fusion polypeptide comprising human MDC and HIV gp120, a fusion polypeptide comprising human SDF-1 and HIV gp120, a fusion polypeptide comprising the amino acid sequence of SEQ ID NO:6, a fusion polypeptide comprising the amino acid sequence of SEQ ID NO:7, a fusion polypeptide comprising the amino acid sequence of SEQ ID NO:5, a fusion polypeptide comprising the amino acid sequence of SEQ ID NO:52, a fusion polypeptide comprising the amino acid sequence of SEQ ID NO:56 and/or a fusion polypeptide comprising the amino acid sequence of SEQ ID NO:50, and a pharmaceutically acceptable carrier, thereby treating or preventing HIV infection in the subject.

In addition, a method of treating or preventing HIV infection in a subject is provided herein, comprising administering to the subject a composition comprising a nucleic acid encoding a fusion polypeptide comprising human IP-10 and HIV gp120, a fusion polypeptide comprising human MCP-3 and HIV gp120, a fusion polypeptide comprising human MDC and HIV gp120, a fusion polypeptide comprising human SDF-1 and HIV gp120, a fusion polypeptide comprising the amino acid sequence of SEQ ID NO:6, a fusion polypeptide comprising the amino acid sequence of SEQ ID NO:7, a fusion polypeptide comprising the amino acid sequence of SEQ ID NO:5, a fusion polypeptide comprising the amino acid sequence of SEQ ID NO:52, a fusion polypeptide comprising the amino acid sequence of SEQ ID NO:56, and/or a fusion polypeptide comprising the amino acid sequence of SEQ ID NO:50, and a pharmaceutically acceptable carrier, under conditions whereby the nucleic acid can be expressed, thereby treating or preventing HIV infection in the subject.

In a further embodiment, the present invention provides a method of treating a B cell tumor in a subject, comprising administering to the subject a fusion polypeptide comprising a human chemokine and a B cell tumor antigen, wherein the B cell tumor antigen can be an antibody, a single chain antibody or an epitope of an idiotype of an antibody, wherein the human chemokine can be MCP-3, MDC or SDF-1, wherein the fusion polypeptide can be a fusion polypeptide comprising human MCP-3 and human a single chain antibody, a fusion polypeptide comprising human MDC and a human single chain antibody or a fusion polypeptide comprising human SDF-1 and a human single chain antibody and wherein the fusion polypeptide can be a polypeptide having the amino acid sequence of SEQ ID NO:51 (human MCP-3/human scFV fusion), a polypeptide having the amino acid sequence of SEQ ID NO:53 (human MDC/human scFv fusion) and/or a polypeptide having the amino acid sequence of SEQ ID NO:55 (human SDF-1/human scFv fusion), thereby treating a B cell tumor in the subject.

Also provided is a fusion polypeptide comprising the human chemokine, SDF-1β, and the V3 loop of HIV-1 envelope glycoprotein, gp120, as well as a fusion protein comprising SDF-1 and gp160 of HIV-1, a fusion protein comprising SDF-1β and gp41 of HIV-1, a fusion protein comprising SDF-1β and an active fragment of gp120, a fusion protein comprising SDF-1β and an active fragment of gp160 and a fusion polypeptide comprising SDF-1β and an active fragment of gp41.

The methods of this invention comprising administering the fusion protein of this invention to a subject can further comprise the step of administering one or more adjuvants, such as an immunostimulatory cytokine to the subject. The adjuvant or adjuvants can be administered to the subject prior to, concurrent with and/or after the administration of the fusion protein as described herein.

The subject of the present invention can be any animal in which cancer can be treated by eliciting an immune response to a tumor antigen. In a preferred embodiment, the animal is a mammal and most preferably is a human.

To determine the effect of the administration of the fusion polypeptide on inhibition of tumor cell growth in laboratory animals, the animals can either be pre-treated with the fusion polypeptide and then challenged with a lethal dose of tumor cells, or the lethal dose of tumor cells can be administered to the animal prior to receipt of the fusion polypeptide and survival times documented. To determine the effect of administration of the fusion polypeptide on inhibition of tumor cell growth in humans, standard clinical response parameters can be analyzed.

To determine the amount of fusion polypeptide which would be an effective tumor cell growth-inhibiting amount, animals can be treated with tumor cells as described herein and varying amounts of the fusion polypeptide can be administered to the animals. Standard clinical parameters, as described herein, can be measured and that amount of fusion polypeptide effective in inhibiting tumor cell growth can be determined. These parameters, as would be known to one of ordinary skill in the art of oncology and tumor biology, can include, but are not limited to, physical examination of the subject, measurements of tumor size, X-ray studies and biopsies.

The present invention further provides a method for treating or preventing HIV infection in a human subject, comprising administering to the subject an HIV replication-inhibiting amount of the chemokine/HIV antigen fusion polypeptide of this invention. As used herein, "a replication-inhibiting amount" is that amount of fusion polypeptide which produces a measurable humoral and/or effector T cell (cellular) immune response in the subject against the viral antigen, as determined by standard immunological protocols, resulting in the inhibition of HIV replication in cells of the subject, as determined by methods well known in the art for measuring HIV replication, such as viral load measurement, which can be determined by quantitative PCR (QPCR) and branched DNA (bDNA) analysis; reverse transcriptase activity measurement, in situ hybridization, Western immunoblot, ELISA and p24 gag measurement (87,88, 89,90,91). The fusion polypeptide can be administered to the subject in varying amounts and the amount of the fusion polypeptide optimally effective in inhibiting HIV replication in a given subject can be determined as described herein.

The fusion polypeptide of this invention can be administered to the subject orally or parenterally, as for example, by intramuscular injection, by intraperitoneal injection, topically, transdermally, injection directly into the tumor, or the like, although subcutaneous injection is typically preferred. Immunogenic, tumor cell growth inhibiting and HIV replication inhibiting amounts of the fusion polypeptide can be determined using standard procedures, as described. Briefly, various doses of the fusion polypeptide are prepared, administered to a subject and the immunological response to each dose is determined (92). The exact dosage of the fusion polypeptide will vary from subject to subject, depending on the species, age, weight and general condition of the subject, the severity of the cancer or HIV infection that is being treated, the particular antigen being used, the mode of administration, and the like. Thus, it is not possible to specify an exact amount. However, an appropriate amount may be determined by one of ordinary skill in the art using only routine screening given the teachings herein.

Generally, the dosage of fusion protein will approximate that which is typical for the administration of vaccines, and typically, the dosage will be in the range of about 1 to 500

μg of the fusion polypeptide per dose, and preferably in the range of 50 to 250 μg of the fusion polypeptide per dose. This amount can be administered to the subject once every other week for about eight weeks or once every other month for about six months. The effects of the administration of the fusion polypeptide can be determined starting within the first month following the initial administration and continued thereafter at regular intervals, as needed, for an indefinite period of time.

For oral administration of the fusion polypeptide of this invention, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this (84).

The present invention also provides a method for producing single chain antibodies against tumor antigens comprising producing a fusion polypeptide comprising a chemokine region and a region comprising a tumor antigen; immunizing animals with an amount of the fusion polypeptide sufficient to produce a humoral immune response to the fusion polypeptide; isolating spleen cells expressing immunoglobulin specific for the fusion polypeptide; isolating the immunoglobulin variable genes from the spleen cells; cloning the immunoglobulin variable genes into an expression vector; expressing the immunoglobulin variable genes in a bacteriophage; infecting E. coli cells with the bacteriophage; isolating bacteriophage from the E. coli cells which express the immunoglobulin variable genes and isolating the immunoglobulin variable gene products for use as single chain antibodies.

The chemokine-scFv fusion proteins described herein would be better targets than tumor cells or purified tumor antigen peptides for antibody selection approaches such as phage displayed scFv production. For example, there are two ways to produce specific Fv displayed on the surface of phage: (1) Immunize mice with tumor cells; isolate immunoglobulin variable fragment genes from spleen cells by RT/PCR; clone the genes into bacteriophage in frame with genes coding phage surface proteins (e.g., major coat protein subunits gpVIII or gpIII of the filamentous bacteriophage) (93,94); and (2) Construct semisynthetic antibody libraries by PCR as described (95). The specific phage producing scFv are selected by several rounds of binding elution and infection in E. coli, using biotin labeled chemokine-tumor antigen (e.g., Muccore). The biotin enables selection of high affinity scFv-phage through binding to streptavidin conjugated magnetic beads. This approach provides simple, fast and efficient production of specific anti-tumor epitope scFv.

As described herein, the present invention also provides a nucleic acid which encodes a fusion polypeptide of this invention and a vector comprising a nucleic acid which encodes a fusion polypeptide of this invention, either of which can be in a pharmaceutically acceptable carrier. Such nucleic acids and vectors can be used in gene therapy protocols to treat cancer as well as to treat or prevent HIV infection in a subject.

Thus, the present invention further provides a method of treating a cancer in a subject diagnosed with a cancer comprising administering the nucleic acid of this invention to a cell of the subject under conditions whereby the nucleic acid is expressed in the cell, thereby treating the cancer.

A method of treating a B cell tumor in a subject diagnosed with a B cell tumor is also provided, comprising administering the nucleic acid of this invention, encoding a chemokine and an antibody or fragment thereof, in a pharmaceutically acceptable carrier, to a cell of the subject, under conditions whereby the nucleic acid is expressed in the cell, thereby treating the B cell tumor.

The methods of this invention comprising administering nucleic acid encoding the fusion protein of this invention to a subject can further comprise the step of administering a nucleic acid encoding an adjuvant such as an immunostimulatory cytokine to the subject, either before, concurrent with or after the administration of the nucleic acid encoding the fusion protein, as described herein.

The nucleic acid can be administered to the cell in a virus, which can be, for example, adenovirus, retrovirus and adeno-associated virus. Alternatively, the nucleic acid of this invention can be administered to the cell in a liposome. The cell of the subject can be either in vivo or ex vivo. Also, the cell of the subject can be any cell which can take up and express exogenous nucleic acid and produce the fusion polypeptide of this invention. Thus, the fusion polypeptide of this invention can be produced by a cell which secretes it, whereby it binds a chemokine receptor and is subsequently processed by an antigen presenting cell and presented to the immune system for elicitation of an immune response. Alternatively, the fusion polypeptide of this invention can be produced in an antigen presenting cell where it is processed directly and presented to the immune system.

If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

For in vivo methods, the nucleic acid encoding the fusion protein can be administered to the subject in a pharmaceutically acceptable carrier as described herein.

In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid to produce the fusion protein of this invention. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Vector delivery can also be via a viral system, such as a retroviral vector system which can package a recombinant retroviral genome (see e.g., 96,97). The recombinant retrovirus can then be used to infect and thereby deliver to the infected cells nucleic acid encoding the fusion polypeptide. The exact method of introducing the exogenous nucleic acid into mammalian cells is, of course, not limited to the use of retroviral vectors. Other techniques are widely available for this procedure including the use of adenoviral vectors (98), adeno-associated viral (AAV) vectors (99), lentiviral vectors (100), pseudotyped retroviral vectors (101). Physical transduction techniques can also be used, such as liposome delivery and receptor-mediated and other endocytosis mechanisms (see, for example, 102). This invention can be used in conjunction with any of these or other commonly used gene transfer methods.

Various adenoviruses may be used in the compositions and methods described herein. For example, a nucleic acid encoding the fusion protein can be inserted within the genome of adenovirus type 5. Similarly, other types of adenovirus may be used such as type 1, type 2, etc. For an exemplary list of the adenoviruses known to be able to infect human cells and which therefore can be used in the present invention, see Fields, et al. (103). Furthermore, it is contemplated that a recombinant nucleic acid comprising an adenoviral nucleic acid from one type adenovirus can be packaged using capsid proteins from a different type adenovirus.

The adenovirus of the present invention is preferably rendered replication deficient, depending upon the specific application of the compounds and methods described herein. Methods of rendering an adenovirus replication deficient are well known in the art. For example, mutations such as point mutations, deletions, insertions and combinations thereof, can be directed toward a specific adenoviral gene or genes, such as the E1 gene. For a specific example of the generation of a replication deficient adenovirus for use in gene therapy, see WO 94/28938 (Adenovirus Vectors for Gene Therapy Sponsorship) which is incorporated herein in its entirety.

In the present invention, the nucleic acid encoding the fusion protein can be inserted within an adenoviral genome and the fusion protein encoding sequence can be positioned such that an adenovirus promoter is operatively linked to the fusion protein nucleic acid insert such that the adenoviral promoter can then direct transcription of the nucleic acid, or the fusion protein insert may contain its own adenoviral promoter. Similarly, the fusion protein insert may be positioned such that the nucleic acid encoding the fusion protein may use other adenoviral regulatory regions or sites such as splice junctions and polyadenylation signals and/or sites. Alternatively, the nucleic acid encoding the fusion protein may contain a different enhancer/promoter (e.g., CMV or RSV-LTR enhancer/promoter sequences) or other regulatory sequences, such as splice sites and polyadenylation sequences, such that the nucleic acid encoding the fusion protein may contain those sequences necessary for expression of the fusion protein and not partially or totally require these regulatory regions and/or sites of the adenovirus genome. These regulatory sites may also be derived from another source, such as a virus other than adenovirus. For example, a polyadenylation signal from SV40 or BGH may be used rather than an adenovirus, a human, or a murine polyadenylation signal. The fusion protein nucleic acid insert may, alternatively, contain some sequences necessary for expression of the nucleic acid encoding the fusion protein and derive other sequences necessary for the expression of the fusion protein nucleic acid from the adenovirus genome, or even from the host in which the recombinant adenovirus is introduced.

As another example, for administration of nucleic acid encoding the fusion protein to an individual in an AAV vector, the AAV particle can be directly injected intravenously. The AAV has a broad host range, so the vector can be used to transduce any of several cell types, but preferably cells in those organs that are well perfused with blood vessels. To more specifically administer the vector, the AAV particle can be directly injected into a target organ, such as muscle, liver or kidney. Furthermore, the vector can be administered intraarterially, directly into a body cavity, such as intraperitoneally, or directly into the central nervous system (CNS).

An AAV vector can also be administered in gene therapy procedures in various other formulations in which the vector plasmid is administered after incorporation into other delivery systems such as liposomes or systems designed to target cells by receptor-mediated or other endocytosis procedures. The AAV vector can also be incorporated into an adenovirus, retrovirus or other virus which can be used as the delivery vehicle.

As described above, the nucleic acid or vector of the present invention can be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The mode of administration of the nucleic acid or vector of the present invention can vary predictably according to the disease being treated and the tissue being targeted. For example, for administration of the nucleic acid or vector in a liposome, catheterization of an artery upstream from the target organ is a preferred mode of delivery, because it avoids significant clearance of the liposome by the lung and liver.

The nucleic acid or vector may be administered orally as described herein for oral administration of the fusion polypeptides of this invention, parenterally (e.g., intravenously), by intramuscular injection, by intraperitoneal injection, transdermally, extracorporeally, topically or the like, although intravenous administration is typically preferred. The exact amount of the nucleic acid or vector required will vary from subject to subject, depending on the species, age, weight and general condition of the subject, the severity of the disorder being treated, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein (84).

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection (104,105). Ideally, a subject will receive a single injection. If additional injections are necessary, they can be repeated at six month intervals for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety.

The present invention is more particularly described in the following examples which are intended as illustrative only since numerous modifications and variations therein will be apparent to those skilled in the art.

EXAMPLES

Mice and tumor. C3H/HeN female mice 6 to 12 weeks of age were obtained from the Animal Production Area of the National Cancer Institute-Frederick Cancer Research and Development Center (NCI-FCRDC, Frederick, Md.). The cell line 38c13 is a carcinogen-induced murine B cell tumor cell line (125). The 38c13 tumor cell secretes and expresses IgM(κ) on the cell surface and is MHC class I positive but class II negative. 38c13 cells from a common frozen stock were passaged in vitro 3 days before use in RPMI 1640 supplemented with 100 U/ml of penicillin and streptomycin, $2 \times 10^{-5}$ M 2-mercaptoethanol and heat inactivated 10% fetal bovine serum (BioWhitaker).

Construction of expression vectors. Two types of expression systems have been used to produce scFv and scFv fusions. In one system, nucleic acid encoding the fusion protein was expressed in a modified pet11d vector (Stratagene) and purified from inclusion bodies of *E. coli*. In the second system, the nucleic acid encoding the fusion polypeptide was cloned into a pCMVE/AB (Arya Biragyn) vector under regulatory elements of the early promoter and enhancer of CMV and expressed in the epidermis of mice as a naked DNA vaccine.

Fv fragments were cloned from two different B cell lymphomas, 38C13 and A20, respectively (106,107) by RT/PCR and produced as recombinant fusion peptides with either IP-10, respectively designated as IP10scFv38 and IP10scFv20A, or MCP3scFv38 and MCP3scFv20A. Specifically, lymphoma specific Vh and Vl fragments were cloned by RT/PCR techniques as single chain antibody from total RNA of 38c13 and A20 tumor cells, designated scFv38 and scFv20A respectively, using the following primers.

PRVh-5': $PRV_H38\text{-}5'$: CTCGAGG TGAAGCTGGTG-GAGTCTGGA (SEQ ID NO:17)

PRVh-3': $PRV_H38\text{-}3'$: AGAGGAGA CTGTGAGAGTG-GTGCCTT (SEQ ID NO:18)

PRVl-5': $PRV_L38\text{-}5'$: GACATCCAGATGACA-CAGTCTCCA (SEQ ID NO:19)

PRVl-3': $PRV_L38\text{-}3'$: GGATCCTTTTATTTCCAGCTTG-GTCCCCCCTCCGAA (SEQ ID NO:20)

$PRV_H20A\text{-}5'$: CCATGGTCCAAC TGCAGCAGT-CAGGGCCTGAC (SEQ ID NO:21)

$PRV_H20A\text{-}3'$: TGAGGAGACTGTGAGTTCGGTAC-CTT GGCC (SEQ ID NO:22)

$PRV_L20A\text{-}5'$: GATGTTGTGATGACGCAGACTC-CACTC (SEQ ID NO:23)

$PRV_L20A\text{-}3'$: GGATCCTT TGACTTCCAGCTTTGT-GCCTCCA (SEQ ID NO:24)

The resulting scFv contained a $(Gly_4Ser)_3$ linker and was cloned into the expression vector pET11d, which was modified to fuse in frame with c-myc and the His tag peptide sequences, followed by an amber stop codon. The resulting scFv contained a 17 a.a. residue linker, GGGGSGGGGSGGGGSGS $(Gly_4Ser)_3GlySer$ (SEQ ID NO:57) (108).

Constructs for the nDNA vaccination were fused in frame to a leader sequence of IP-10 in pCMVE/AB to enable secretion. The carboxy-terminus of scFv was fused in frame with the tag sequence encoding c-myc peptide and six His residues, respectively: GGA TCC GCA GAA GAA CAG AAA CTG ATC TCA GAA GAG GAT CTG GCC CAC CAC CAT CAC CAT CAC TAA CCCGGG (SEQ ID NO:25). Genes for the mature sequence of murine chemokines, IP-10 and MCP-3, were cloned by RT/PCR technique from RNA of the LPS-induced murine monocyte cell line ANA-1 (109) utilizing the following primers:

PRmIP10-5': CCATGGCCATCCCTCTCGCAAG-GACGGTCCGC (SEQ ID NO:26)

PRmIP10-3': GAATTCAGG AGCCCTTTTAGAC-CTTTTTTG (SEQ ID NO:27)

PRmMCP3-5': ACCATGGCCCAACCAGATGGGCC CAATGCA (SEQ ID NO:28)

PRmMCP3-3': GAATTCAGGCTTTGGAGT-TGGGGTTTTCAT (SEQ ID NO:29)

The cDNA for human monocyte chemotactic protein-3 was PCR amplified and subcloned using the specific primers:

PRhMCP3-5': ACCATGGCGCAACCGGTAGG-TATAAACACAAGCA (SEQ ID NO:30)

PRhMCP3-3': GAATTCCAGTTTCGGCGTCTGT-GTCTTTTA (SEQ ID NO:31)

Human IP10 was PCR amplified and subcloned using specific primers:

PrhIP10-1: CCCATGGTACCTCTCTCTAGAACCGTA (SEQ ID NO:32)

PrhIP10-R1: GGATCCTTAAGGAGATCTTTTAGA-CATTTCCTTGCTAACT (SEQ ID NO:33)

IP-10, MCP-3 or control viral epitope (PreS2 and DomA) fusions were made by fusing them to amino-terminus of scFv through a short spacer sequence: 5' <u>GAA TTC</u> AAC GAC GCT CAG GCG CCG AAG AGT <u>CTC GAG</u> 3' (SEQ ID NO:34), encoding the amino acid sequence: EFNDQAPKSLE (SEQ ID NO:11). Two unique restriction endonuclease sites were introduced at the ends of the space to facilitate cloning: EcoRI at the 5' end (underlined) and XhoI at the 3' end (underlined). All constructs were verified by DNA dideoxy-sequencing method, using T7 SEQUENASE kit (Amersham).

IP10 or MCP-3 chemokines were cloned into the scFv38 expression vector through NcoI and XhoI restriction sites. The resulting fusion nucleic acid contained the chemokine gene ligated to the 5'-end of the scFv38 gene and separated with a short spacer sequence, as described above.

Bacterial expression and scFv purification. The recombinant proteins were expressed in BL21(DE3) cells (InVitrogen) as inclusion bodies after 8 hours of induction in Super-Broth with 0.8 mM IPTG in the presence of 150 µg/ml carbenicillin and 50 µg/ml ampicillin at 30° C. IP10-scFv38, MCP3-scFv38 and scFv38 were purified from the inclusion bodies with a modified method (110). Briefly, inclusion bodies, denatured in 6M GuHCl, 100 mM $NaH_2PO_4$, 10 mM Tris-HCl, pH 8.0, were reduced in 0.3M DTE and refolded at a concentration of 80 µg/ml in the refolding solution (Tris-HCl, pH 8.0, 0.5M arginine-HCL, 4 mM GSSG and 2 mM EDTA) for 72 hours at 10° C. The refolded solution was dialyzed in 100 mM Urea and 20 mM tris-HCl, pH 7.4 and the recombinant protein was purified by binding to heparin-sepharose resins (Pharmacia, Biotech, Uppsala, Sweden). The integrity and purity of the recombinant protein was tested by PAGE gel electrophoresis in reducing conditions and by Western blot hybridization with mAb 9E10. The purification yielded 2–20 mg/l of the soluble protein with greater than 90% purity.

Purified fusion polypeptide was tested for the ability to inhibit binding of native IgM 38c13 (Id38), as compared to positive sera from mice immunized with Id38-KLH. ELISA plates were coated with 10 µg/ml Id38, then wells were incubated with anti-Id38 positive sera (1:500) and titrated amounts of scFv. Id38 (10 µg/ml) and IP10scFv20 (IP-10 fused to an irrelevant scFv) were used as positive and negative control samples, respectively.

Recombinant fusion proteins purified from *E. coli* were characterized for proper idiotype folding by their ability to inhibit 38c13 IgM binding to a monoclonal (SIC5 mAb) or polyclonal anti-idiotypic sera. These results suggest that IP-10 and MCP-3 fusion did not interfere with the proper conformation of scFv38. Next, receptor binding experiments demonstrated that both IP-10 and MCP-3 fused scFv, but not control viral epitope DomA fused scFv38 (DomAscFv38), bound to their respective chemokine receptors on unfractionated murine splenocytes and purified T cells. The native ligands IP-10 or MCP-3 inhibited only binding of respective chemokine-scFv. Moreover, no binding was detected with truncated IP10TFBscFv38, which contained an intact heparin binding domain of IP-10 with a deleted (amino-terminal 9 a.a. residues) chemokine receptor binding portion. Next, chemotactic activity of the fusion proteins was tested. All chemokine-scFv proteins, but not a viral epitope fused scFv38 control (PreS2scFv38), induced in vitro chemotaxis of murine lymphocytes in a dose dependent manner. Chemotactic activity also was confirmed in vivo by histologic evaluation of the skin at the site of injection, which showed that the dermis and subcutaneous layers injected with IP10FBscFv38 or MCP3FBscFv38, but not with control PreS2scFv38, contained significant numbers of infiltrating mononuclear cells and some PMN. Therefore, IP-10 and MCP-3 fused scFv proteins were biologically active and retained functional properties of their corresponding chemokines.

In vivo immunization and tumor protection. Six- to nine-week old female C3H/HeN mice were immunized intraperitoneally (i.p.) with 100 to 200 µg of the soluble protein in PBS and control immunogen Id38-KLH two times at two week intervals or were shaved and immunized by Accell gene delivery device (Agracetus, Inc., Middleton, Wis.) with 1µ gold particles carrying 1–3 µg plasmid DNA. Sera were collected by orbital bleeding two weeks after each vaccination. Serum anti-idiotypic (anti-Id) antibody levels were tested as described (111) over microtiter plates coated with 10 µg/ml native IgM 38c13. Two weeks after the last immunization, mice were inoculated with 2000 38c13 tumor cells i.p. Survival was determined, and significance with the respect to time to death, was assessed using BMDP IL software (BMDP statistical software, Los Angeles). Mice were observed daily for any signs of toxicity and date of death and animals surviving>80 days after tumor challenge were killed and were reported as long-term survivors.

Mice were immunized either with a plasmid coding for MCP3scFv38 fusion or a mixture of DNA constructs expressing unlinked scFv38 and MCP3scFv20A (scFv38D+MCP3scfv20AD).

Ten mice per group were immunized with two types of scFv3 8 fused to IP-10, respectively IP10scFv38 or IP10scFv38(TV), differing only in orientation of variable genes in scFv. Control mice received IgM-KLH (Id38-KLH) and IP10 fusion to A20 lymphoma scFv (IP10scFv20A). Ten mice per group were immunized i.d. with plasmid coding either for chemokine fusion vaccine (MCP3scFv38D), or free scFv (scFv38D), or viral epitope preS2 fused scFv (PreS2scFv38D).

Effector $CD8^+$ and $CD4^+$ cells were depleted two weeks after the last immunization with three i.p. injections of 400 µg α-CD8 mAb 53.6.72, or α-CD4 mAb GK1.5 (both ammonium sulfate purified ascites, Biological Resource Branch, NCI-FCRDC) (32,34), or control rat IgG (Sigma). Control mice were immunized with plasmid expressing MCP3 fused to A20 scFv (MCP3scFv20AD). The α-$CD8^+$ depletion resulted in a drop of $CD8^+$ cells from 9.5% to 0.7%, while $CD4^+$ cell proportions remained unchanged, about 16%, as monitored by fluorescence activated cell sorting (FACS) staining. Similarly, α-$CD4^+$ mAb treatment decreased the proportion of $CD4^+$ cells from 18% to 1.8%, while it did not affect the $CD8^+$ cell count, which remained at 10.6%.

Ten Balb/C mice per group were immunized i.p. twice with 100 µg of IP-10 or MCP-3 fused with scFv20A protein in PBS (IP10scFv20A and MCP3scFv20A, respectively) and challenged i.p. with $10^5$ A20 tumor cells. To determine the role of free versus linked chemokine, IP10scFv20A (which failed to protect, but expressed the correct scFv20A) was co-injected with MCP-3 fused to an irrelevant scFv38 (IPscFv20A+MCP3scFv38). Control mice were immunized with A20 IgM-KLH (Id20A-KLH).

Immunoassays and serum anti-idiotypic antibody. The assessments for correct folding of purified scFv38 and fusion scFv38 were determined by ELISA with mAbs and by inhibition assay with Id38-KLH sera (immunized with native IgM 38c13 conjugated to KLH). Briefly, microliter plates (Nunc, Naperville, Ill.) were coated overnight at 4° C.

with 10 μg/ml anti-c-myc mAb 9E10 in carbonate buffer (50 mM NaHCO$_3$, pH 9.0). The wells were blocked with 5% nonfat dry milk in PBS for 30 min. Plates were washed in 0.05% Triton X-100 in PBS, and serially diluted scFv (starting from 10 μg/ml in 50 μl 2% BSA/PBS) was applied, after which plates were incubated 40 min at room temperature. After washing, the wells were incubated with 50 μl of 1:300 diluted biotinylated anti-Id38 mAb in 2% BSA/PBS for 30 min at room temperature. Wells were washed and incubated with streptavidin-HRP conjugate (1:5000) in 2% BSA/PBS for 30 min at room temperature. Then, wells were washed and incubated with ABTS peroxidase substrate (KPL, Gaithersburg, Md.) and the absorbance at 405 nm was measured.

Inhibition assays were performed as described above, except plates were coated with 10 μg/ml of native IgM 38c13, then, wells were incubated for 30 min at room temperature with a 1:2 dilution of positive Id38-KLH sera mixed with serially diluted purified scFv proteins starting from 50 μg/ml in 2% BSA/PBS. The bound antibodies from the sera were assayed by incubating wells for 30 min at room temperature with anti-mouse IgG-HRP mAb (Jackson).

Serum anti-idiotypic (anti-Id) antibody levels were tested as described (37). Briefly, mouse serum was serially diluted over microtiter plates coated with 10 μg/ml native IgM 38c13. Binding of antibodies in the serum to 38c13 IgM was detected by goat anti-mouse IgG-HRP. Serum anti-Id antibody levels were quantitated by comparing sera titration curves with a standard curve obtained with a known concentration of a mixture of purified monoclonal anti-Id antibodies. Antibody levels were expressed in g/ml of serum for individual mice. In each ELISA, sera obtained from mice immunized with control IgM-KLH were included as negative controls. Such sera never showed any titration binding activity on Id-38c13.

In vitro and in vivo chemotaxis assays. Single cell suspensions were prepared from spleens of untreated C3H/HeJ mice. Murine T cell enrichment columns (R&D System, Minneapolis, Minn.) were then used to prepare a purified murine T cell population via high-affinity negative selection according to the manufacturer's instructions. The isolation procedure typically yielded over 89% CD3$^+$ T cells, as determined by FACS analysis. T cell migration in vitro was assessed by 48-well microchemotaxis chamber technique. Briefly, a 26 μl aliquot of the recombinant scFv fusion protein serially diluted in the chemotaxis medium (RPMI 1640, 1% BSA, 25 mM HEPES) was placed in the lower compartment and 50 μl of cell suspension (5×10$^6$ cells/ml) was placed in the upper compartment of the chamber. The two compartments were separated by a polycarbonate filter (5 μm pore size; Neuroprobe, Cabin John, Md.) coated with 10 μg/ml of fibronectin (Sigma, St. Luis, Mo.) and incubated overnight at 4° C. or for 2 hours at 37° C. The chemotaxis assay was performed at 37° C. for 2 hours. Then the filter was removed, fixed and stained with Diff-Quik (Harlew, Gibbstown, N.J.). The number of migrated cells in three high power fields (400×) was counted by light microscopy after coding the samples. The results are expressed as the mean±SE value of the migration in triplicate samples.

T cell migration in vitro was assessed by the 48-well micro chemotaxis chamber technique as described (112). Single cell suspensions were prepared from spleens of untreated C3H/HeJ mice. Murine T cell enrichment columns (R&D System, Minneapolis, Minn.) were then used to prepare a purified murine T cell population via high-affinity negative selection according to the manufacturer's instruction. The isolation procedure typically yielded over 89% CD3$^+$ T cells, as determined by FACS analysis.

In order to test in vivo effects on cell accumulation, C3H/HeN mice were injected s.c. with a single 10 μg dose of scFv fusion proteins. Portions of the skin from the site of injection were removed 72 hours after the injection, fixed in 10% neutral buffered formalin, embedded in paraffin, sectioned at 5 μm and stained with hematoxylin and eosin (H&E). Slides were evaluated microscopically without knowledge of the experimental treatment.

In vivo cellular infiltration into murine skin. The numbers of PMN and mononuclear (MN) cells infiltrated into murine skin were graded as following:-, no significant lesion; 1, mild; 2, moderate; 3 severe; F, focal; MF, multi focal. Mice were injected with 10 μg of IP10scFv38 (N8), MCP3-scFv38 (N21), preS2scFv38 (N18), or PBS, subcutaneously. After 72 h, the injection site was excised and examined histologically on coded slides to determine the extent of infiltration. The amount of endotoxin injected with samples was 0.5–1 units.

Chemokine binding assay and confocal microscopy. Chemokine binding assays were performed using laser confocal microscopy (113). Purified T cells or spleen cells from C3H mice were used at ~1×10$^6$ per ml and were incubated with 100 nM chemokine-scFv (N6IP10scFv38, N21MCP3scFv38), control viral epitope-scFv (N2 DomAscFv38), or truncated IP10scFv38 (N16IP10TscFv38) for 1 hour at 37° C. For the ligand competition assay, 100 nM chemokine-scFv was incubated with 500 nM of the corresponding chemokine (IP-10 or MCP-3). Samples were washed 2× in PBS and fixed in suspension with 2% paraformaldehyde. The samples were incubated at RT for 15 min. Slides containing the samples were incubated in 9E10 anti c-myc mAb primary antibody at a 1:50 dilution in wash buffer (0.25% gelatin, 0.15% saponin, 1% goat serum in PBS). Slides were then incubated with goat anti-mouse IgG F(ab')2-FITC (Boehringer-Mannheim) at a 1:50 dilution for 30 min at RT in a humidified chamber. Slides were washed 3×5 min in 0.25% gelatin, 0.15% saponin in TBS. Slides were then incubated for 10 min in a 1:100 dilution of DAPI, washed 2× briefly in TBS, then 1× briefly in dH$_2$O, air-dried and mounted using aqueous mounting medium appropriate for immunofluorescence (Gel/Mount, Biomeda).

The traditional approach to enhance immunogenicity by cross linking to KLH is not effective. Several different approaches were used for the production of single chain antibody fragments from 38c13 cells (scFv38) in E. coli. Yield of scFv38 differed significantly depending on the method used. Production of scFv38 through a secretory path using a PelB leader sequence as a native protein was least efficient. The problem was solved when scFv38 was produced as insoluble "inclusion" bodies, which yielded about 2–8 mg of refolded scFv per liter of the batch culture with greater than 90% purity. Folding properties of the produced scFv38 were monitored by either (i) inhibition assay with native Id38; or (ii) modified ELISA assay where scFv38 was captured through an anti-c-myc tag and detected with the biotinylated monoclonal anti-Id38 antibody (anti-Id38 mAb does not recognize linear or incorrectly folded epitope). These experiments demonstrated that scFv38, but not irrelevant scFv20A, specifically binds to anti-Id38c mAb and inhibits binding of the native Id38c to anti-Id38c mAb, 50% binding inhibition by 10–15 fold excess of scFv38. In addition, positive sera from Id38c-KLH immunized mice specifically recognized purified scFv38. These data indicate that purified scFv38 is folded correctly and imitates the idiotype of the native antibody (Id38c) of B cell lymphoma 38c13.

Immunization experiments showed that scFv38, similarly to the native Id38c IgM, is a poor immunogen. Attempts were made to convert scFv38 into a potent immunogen by chemical cross linking with KLH, in analogy to the native Id38c. However, in contrast to Id38-KLH, i.p. immunizations of syngeneic mice with 100 μg of scFv38-KLH did not elicit any anti-Id38c specific antibody response. This inability to induce anti-Id38 response correlates with the loss of ability to affect binding of anti-Id38 mAb (SIC5) to Id38c by samples containing scFv38-KLH, while a control sample of an equimolar mixture of non-cross linked scFv38 and KLH (scFv38+KLH) inhibited anti-Id38/Id38c binding similarly to pure scFv38. These data indicate that a fragile Id conformation of scFv38 was removed by KLH cross linking and that this traditional approach is not applicable for the enhancement of immunogenicity of scFv38.

Design and Production of Chemokine Fused scFv38. Murine IP10 was subcloned from LPS induced monocyte cell line ANA-1 by RT/PCR using specific primers as described herein and inserted in frame in front of the scFv38 DNA sequence. The resulting fusion gene was designated as IP10FBscFv38MH. Similarly MCP-3 fused scFv38 was constructed and designated as MCP3FBscFv38MH. In order to evaluate input of the immunoglobulin V chain specific orientation, two variants of fusion chemokine-scFv genes were designed, one containing a $V_H$-$V_L$ and one containing a $V_L$-$V_H$ sequence, respectively designated as scFv38MH and scFv38(INV)MH.

All fusion proteins used in these experiments were purified from inclusion bodies of E. coli, solubilized and refolded as described herein. A spacer sequence, as described herein, was introduced into the chemokine fusion proteins and correct folding was tested for each recombinant protein. These tests demonstrated that both IP-10 and MCP-3 fused scFv38 recombinant proteins folded correctly, thereby imitating the structure of native idiotype of 38c13 lymphoma Ig.

IP10- and MCP3-scFv38 fusion proteins retain functional properties of chemokines. The ability of the fusion proteins to induce chemotaxis in vitro of spleen cells or purified T cells from C3H/HeN was tested. Both chemokine fusion proteins IP10FBscFv38MH and MCP3FBscFv38MH induced chemotaxis of murine lymphocytes in a dose dependent manner, demonstrating a typical bell shape curve, with the maximum activity at 100 μg/ml concentration. Therefore, these data indicate that scFv38 became chemotactic due to the presence of the fused chemokine. A control sample, the viral epitope, but not chemokine, fused to scFv38 (PreS2FBscFv38MH) did not cause any in vitro chemotaxis.

The ability of IP10FBscFv38MH and MCP3FBscFv38MH proteins to induce chemotaxis in vivo in C3H/HeN mice was also tested. Mice were s.c. injected once with 10 μg of the fusion protein and after 72 hours, the skin around the site of injection was removed and analyzed as described herein. The endotoxin contamination level of samples injected was less than 0.5–1 units. Histologic evaluation of the skin at the site of the injection showed that the dermis and subcutaneous layer contained significant amounts of monocytes and less PMN infiltration in mice injected with IP10FBscFv38MH and MCP3FBscFv38MH. In contrast, the skin from mice injected with control PreS2FBscFv38MH showed no significant cellular infiltration. These data demonstrate that scFv38 is converted into a chemotactic protein by fusion with IP-10 or MCP-3 chemokines and that these proteins are able to induce chemotaxis in vivo.

Chemokine binding competition experiments were performed on purified murine T cells and spleen cells. Confocal microscopy experiments demonstrated that both chemokines IP-10 and MCP-3 fused with scFv38, but not control viral epitope DomA fused with scFv38 (DomAFBscFv38), bound to purified murine T cells and spleen cells. The binding was specifically inhibited by incubation with the corresponding native chemokine, IP-10 or MCP-3, respectively. Thus, chemokine fused scFv38 acts as a chemotactic protein via binding to the corresponding chemokine receptor.

Chemokine fusion enables conversion of scFv into a good immunogen. To test the potency of the chemokine fused to scFv38, syngeneic C3H mice were i.p. injected with 100 μg of the purified fusion protein, without any adjuvants. No significant anti-Id38 antibody response was induced by repeated injections of scFv38 alone (up to 200 μg). However, the anti-Id38 antibody response was induced by injection of IP10FBscFv38 and MCP3FBscFv38 into mice. This response was specific to 38c13 lymphoma Id, because only immune sera from groups IP10FBscFv38, MCP3FBscFv38 and Id38-KLH reacted in ELISA with the IgM from 38c13, but not with an isotype matched irrelevant IgM. The positive anti-Id38 response was not detected when mice were immunized with a IP10-scFv38, which had indistinguishable chemotactic activity and an incorrectly folded scFv38.

The single immunization of 50–100 μg of IP10FBscFv38 induced detectable levels of anti-Id38 titers. However, significantly higher amounts of the specific antibody were detected usually after three immunizations. Interestingly, despite comparable levels of Id folding, as detected in vitro, IP10FBscFv38 was a much more potent anti-Id38 inducer, than MCP3FBscFv38. Three immunizations with IP10FBscFv38 produced about 15 to 233 μg/ml anti-Id38, while MCP3FBscFv38 produced from 1 to 25 μg/ml. However, these levels of anti-Id38 production were lower than the amount produced after a single i.p. injection of 50 μg Id38-KLH antibody, which was within a range of 400–800 μg/ml.

Immunization with chemokine fused scFv38 can protect against tumor challenge. In the 38c13 model, a tumor challenge dose as low as 100 cells is lethal in 100% of control immunized mice (111). It has been shown that a single i.p. immunization with 25–50 μg of tumor-derived Id conjugated to KLH in syngeneic C3H mice produced modest resistance against a subsequent minimum lethal dose i.p. tumor challenge 2 weeks later, with no significant differences between different routes of immunization (111).

Ten animals per group were immunized with 100 μg of IP10FBscFv38 or IP10FBscFv38(INV) three times at biweekly intervals. Control group animals were injected either with IP-10 fused to the irrelevant lymphoma scFv (IP10FBscFv20A), scFv38 alone, or PBS. The survival rate of the control group of animals immunized with IP10FBscFv20A was indistinguishable from the survival rate of the group that received scFv38 alone or PBS injections, suggesting the lack of any antitumor effects of IP10 immunization (all animals died within 14 days). However, immunization with either variant of scFv fused with IP-10 significantly increased survival of mice (P=0.0002, respectively, groups 1 and 2 vs. group 3; n=10 mice per group). Survival data were not different between groups 1 and 2, indicating that linkage in either orientation of variable chains in scFv38 resulted in an equivalent Id38 folding and consequently induced a similar anti-tumor response. A positive control group of animals immunized with native antibody Id38 cross-linked to KLH demonstrated the highest survival with the median at 28 days.

In contrast to IP-10 fused to scFv38, mice immunized with MCP3FBscFv38 were not protected reproducibly, although in some experiments, an increase in survival was observed, which correlates with the ability of this protein to induce an anti-Id38 antibody response. The animals immunized with the incorrectly folded scFv38 fused to IP-10, IP10scFv38, could not elicit an anti-Id38 response and demonstrated no protection against tumor challenge. These data indicate that scFv38 is converted into a potent immunogen through fusion with chemokine IP-10 and that it can induce significant tumor protection. The protection depended mostly from the ability to elicit higher titers of anti-Id38 antibody.

Naked DNA vaccination with IP-10 fused scFv38. In an attempt to improve the potency of the anti-tumor response, expression plasmid vectors were constructed, consisting of the promoter-enhancer sequence from the CMV early gene linked to either a scFv gene alone or fused with MCP-3 or IP-10 for particle-mediated DNA vaccine delivery. Mice received three biweekly i.d. immunizations, consisting of four shots of 0.5 mg gold particles carrying 1–3 µg of plasmid DNA each. Mice receiving control plasmids scFv38D, PreS2scFv38D (50 a.a. preS2 region of the middle surface antigen of HBV, a non-chemokine carrier), or scFv20AD (MCP-3 fusion to the A20 scFv) generated no anti-idiotypic antibody. In contrast, immunization with MCP3 or IP-10 fusions elicited high levels of anti-Id38 antibody (mean 909±625 and 752±660 µg/ml, respectively). Furthermore, these levels of antibody were comparable to those elicited by IgM-KLH (mean 576±104). Groups of ten immunized mice were challenged with tumor two weeks after the final immunization. Significant protective immunity was demonstrated in mice immunized with MCP3scFv38D (40% survival, log rank P=0.005 vs. PreS2scFv38D control). The survival of mice receiving either of control plasmids PreS2scFv38D, free scFv38D or MCP-3 fusion to the irrelevant scFv20D was not significantly different from those receiving PBS. Furthermore, the magnitude of protection with MCP3scFv38D exceeded that demonstrated with IgM-KLH (P<0.03, chi-square analysis of pooled data). In addition, to determine if the chemokine moiety must be linked to scFv to render its immunogenicity, mice were immunized with a mixture of DNA constructs expressing unlinked scFv38 and MCP3scFv20A in a separate experiment. Neither antibody response, nor survival was observed. Thus, this effect required that the chemokine be physically linked with scFv.

In vivo depletion of T-cell subsets. The MCPscFv38D induced protective immunity mediated by effector $CD8^+$ or $CD4^+$ T cells was also investigated. Two weeks after immunization with MCP3scFv38nDNA, groups of ten mice were randomly assigned to treatment with specific mAb depleting $CD8^+$ or $CD4^+$ T cells, or with normal rat IgG as a control every other day for three doses before challenge. Comparison of treated and untreated mice immunized with MCP3scFv38D revealed a loss of protection for the groups receiving either anti-CD8 mAb (0% vs 40% survival, respectively, log rank P=0.08) or anti-CD4 mAb (0% vs 30% survival, respectively). These data indicate that immunization with a naked DNA construct expressing MCP-3 fused to scFv38 elicited efficient anti-Id38 antibody production sufficient to delay tumor growth but complete protection was dependent upon T cells at the effector phase of the response. Thus, these data indicate that, in addition to inducing a vigorous humoral response, MCP3scFv38D induces effector $CD8^+$ and $CD4^+$ T cells, which are required for protective anti-tumor immunity elicited by pMCP3scFv38 (P<0.004 by Fisher's exact test, logrank P=0.02, T-cell depleted vs. rat IgG treated).

MCP-3 fusion also elicits protective anti-tumor immunity in a second lymphoma model. Comparable results were observed with the MCP3scFv20A fusion protein and plasmid MCP3scFv20AD, which also elicited protective immunity against corresponding A20 lymphoma cells. Of particular importance, the potency of MCP3scFv20A fusions was also superior to that of IgM-KLH in this second lymphoma model (40% survival vs 0%, log rank P=0.05). One difference observed between the two models is that IP-10 fusion scFv20a did not produce protective immunity. Thus, the observation that mixing MCP3scFv38 with IP10scFv20A did not produce protection (0% vs 40% survival for MCP3scFv20A, log rank P=0.03), provides further evidence that the chemokine must be physically linked to scFv.

In summary, these data demonstrate that fusion of chemokines MCP-3 and IP-10 to a self tumor antigen can convert non-immunogenic scFv into a potent immunogen. Chemokine fusion did not interfere with correct folding of the native idiotype, the resulting chemokine-scFv was fully biologically active (induced in vitro and in vivo chemotaxis and bound specifically to the corresponding receptors). These data also indicate that the immune response to the chemokine-scFv is mediated through an interaction with the chemokine receptor, as this effect is only seen when chemokine and scFv were physically linked. Immunizations with the truncated IP10TscFv38, which lost its ability to bind to the chemokine receptor and induce T cell chemotaxis in vitro, could not elicit efficient anti-Id production (mean 4±2 µg/ml). These data also demonstrated significantly better tumor protection when immunization was performed by the gene gun delivery of naked DNA expressing MCP-3-scFv38.

The induction of protective anti-tumor immunity required both $CD8^+$ and $CD4^+$ effector T cells. However, a minimum threshold level of anti-idiotypic antibody was probably also important since the improved survival depended on an efficient anti-Id antibody response (114,115). No anti-Id38 antibody response or tumor protection is detected in mice immunized with incorrectly folded idiotype fusion protein or nDNA fusion protein constructs expressing incorrectly folded idiotype. Furthermore, the protective anti-tumor immunity elicited by MCP3scFv fusions as either protein or DNA vaccines was superior to that of Id-KLH protein, the formulation currently in clinical testing (116,117), in both tumor models (P<0.03 and P<0.05 by chi-square test for pooled data and MCP3-scFv vs. Id-KLH for 38c13 and A20, respectively). Moreover, this effect does not require use of adjuvants. Finally, both the superior potency of MCP3-scFv fusions relative to Id-KLH protein and its ability to induce a critical effector $CD8^+$ and $CD4^+$ T cells responses distinguish these fusion proteins from other idiotype proteins and DNA vaccines (118,119).

Production of fusion polypeptides comprising a human chemokine and a human tumor antigen or HIV antigen. To produce the fusion polypeptides of the present invention which comprise a human chemokine region and a human tumor antigen region or HIV antigen region, the following procedures are carried out: Tumor or viral antigen is cloned by PCR or RT/PCR from DNA or RNA of biopsy cells of a patient, using specific primer. The primers are made using standard methods for selecting and synthesizing primer sequences from analysis of known sequences of the genes of interest (e.g., from GenBank, Kabat Ig sequence database and other available genetic databases, as are known in the art). For example, lymphoma or myeloma-specific scFv is cloned by RT/PCR from the nucleic acid from a patient's lymphoma or myeloma biopsy cells or from nucleic acid from hybridoma cells expressing the patient's immunoglobulin. Several sets of primers are used to clone human variable (V) genes based on GenBank and Kabat IG sequence data. As in cloning murine scFv, human tumor V fragments are cloned and sequenced using a family-specific primer or primer mixture for leader and constant region sequences. Next, scFv is constructed using primers based on the sequence of each V gene cloned. These primers can have specific restriction endonuclease sites to facilitate routine cloning, or scFv is made by overlapping PCR, according to methods well known in the art. The vector expressing the fusion polypeptide can contain several unique restriction endonuclease sites (e.g., XhoI, BamHI) between the 3' end of the spacer sequence and the 5' end of the c-myc and six His tag sequences, or the 5' end of the polyA transcription terminator region (if a SmaI site is used), thus enabling routine cloning of any scFv, tumor antigen or viral antigen.

As described herein, nucleic acid encoding the human chemokine-tumor antigen fusion polypeptides of this invention is expressed in yeast (e.g., *Saccharomyces cerevisiae*; *Pichia pastoris*, etc.) or in mammalian cell culture according to methods standard in the art. The proteins produced in these systems are affinity purified with anti-c-myc antibodies (e.g., 9E10; M5546, Sigma) or anti-poly-His antibodies (e.g., H1029, Sigma). Alternatively, immobilized metal chelate affinity chromatography (Ni-NTA resin, Qiagen) is used for purification of soluble or refolded fusion polypeptides.

Administration of fusion polypeptides to human subjects. Immunity and suppression of tumor growth in a human subject. To elicit a tumor cell growth-inhibiting response in a human subject, a fusion polypeptide comprising a human chemokine and a tumor antigen which is present in the human subject is administered to the subject subcutaneously in a dose ranging from 1 to 500 µg of the fusion polypeptide once weekly for about eight weeks or once monthly for about six months. Within the first month following the initial immunization, blood samples can be taken from the subject and analyzed to determine the effects of administration of the fusion polypeptide. Particularly, the presence in the subject's serum, of antibodies reactive with the tumor antigen in the fusion protein can be determined by ELISA, Western blotting or radioimmunoprecipitation, or other methods for detecting the formation of antigen/antibody complexes as would be standard practice for one of ordinary skill in the art of immunology. Also, a cellular immune response to the tumor antigen in the fusion polypeptide can be detected by peripheral blood lymphocyte (PBL) proliferation assays, PBL cytotoxicity assays, cytokine measurements, or other methods for detecting delayed type hypersensitivity and cellular immune response, as would be standard practice for one of ordinary skill in the art of immunology. Additionally, the kinetics of tumor growth and inhibition of tumor cell growth can be determined by monitoring the subject's clinical response, through physical examination, tumor measurement, x-ray analysis and biopsy. The exact dosage can be determined for a given subject by following the teachings as set forth herein, as would be standard practice for one of ordinary skill in the art of vaccine development.

As an example of how the vaccine of this invention can be administered to a patient to treat cancer or to treat or prevent HIV infection (with the additional administration of adjuvants, such as immunostimulatory cytokines, if desired), the following is a complete protocol for a clinical trial describing the administration of Id-KLH and GM-CSF to patients to treat follicular lymphoma. The same study design can be employed for the administration of the chemokine-tumor antigen fusion polypeptide or the chemokine-viral antigen fusion polypeptide of the present invention or nucleic acids encoding the fusion polypeptides of this invention, with appropriate modifications, as would be apparent to one of skill in the art. In particular, studies to test the efficacy of HIV vaccines are well known in the art and the clinical protocol described herein can be readily modified by one of skill in the art as appropriate to test the efficacy of the HIV fusion polypeptide or HIV fusion polypeptide-encoding nucleic acid of this invention according to well known protocols for testing HIV vaccines (126,127).

1.1 Background and Rational

The development of a vaccine against human malignancies has been a long-sought goal which has yet to be achieved. Many of the efforts toward this end have been frustrated by the lack of identification of a tumor-specific antigen which would allow tumor cells to be distinguished from normal cells. Conceptually, such an antigen could be used as a vaccine to induce the hosts immune system to reject cells bearing that antigen.

Immunoglobulin (Ig) molecules are composed of heavy and light chains, which possess highly specific variable regions at their amino termini. The variable regions of heavy and light chains combine to form the unique antigen recognition site of the Ig protein. These variable regions contain determinants that can themselves be recognized as antigens, or idiotopes. B-cell malignancies are composed of clonal proliferations of cells synthesizing a single antibody molecule with unique variable regions in the heavy and light chains. B-cell lymphomas are neoplasms of mature resting and reactive lymphocytes which generally express synthesized Ig at the cell surface. The idiotypic determinants of the surface Ig of a B-cell lymphoma can thus serve as a tumor-specific marker for the malignant clone.

Studies in experimental animals, as well as in man, have demonstrated the utility of the Ig idiotype as a tumor-specific antigen for the study of the biology of B-cell lymphoma in vitro and as a target for passive immunotherapy in vivo (1,2,3). Furthermore, active immunization against idiotypic determinants on malignant B cells has been demonstrated to produce resistance to tumor growth in a number of syngeneic experimental tumor models, as well as specific anti-tumor therapy against established tumors (4–13). These results, taken together, provided the rationale for testing autologous tumor-derived idiotypic surface Ig (Id) as a therapeutic "vaccine" against human B-cell lymphoma. Furthermore, preclinical studies in subhuman primates demonstrated that optimal immunization with human lymphoma-derived Id required conjugation of the protein to an immunogenic protein carrier (keyhole limpet hemocyanin; KLH) and emulsification in an adjuvant (14).

Guided by these observations, nine patients with B-cell lymphoma were immunized with autologous Id protein (15). These patients received no anti-tumor therapy during the time of the study. They were either in complete remission or in a state of minimal residual disease following conventional chemotherapy. In addition, three patients with rapidly progressive recurrent lymphoma were enrolled in a separate safety study; all three required reinstitution of chemotherapy shortly after enrollment, did not complete the immunization series, and were not studied further. They received intramuscular injections of 0.5 mg of Id conjugated to KLH at 0, 2, 6, 10 and 14 weeks, followed by two booster injections at 24 and 28 weeks. Patients in the first trial (five patients)

received Id-KLH alone for the first three immunizations, then Id-KLH emulsified in a Pluronic polymer-based adjuvant vehicle formulation for all subsequent immunizations. Because no idiotype-specific immune responses were observed prior to the addition of the adjuvant to the program in this first group of patients, patients in the second trial (four patients) received the entire series of immunizations with this adjuvant. All patients were analyzed for idiotype-specific antibody production and peripheral blood mononuclear cell (PBMC) proliferative responses in vitro immediately before each immunization and at one to two month intervals following the last immunization. The KLH carrier provided a convenient internal control for immunocompetence of the patients and all patients demonstrated both humoral and PBMC proliferative responses to the KLH protein, with the exception of one patient, who demonstrated only the latter. Seven of the nine patients demonstrated either a humoral (n=2) or a cell-mediated (n=4) anti-idiotypic immunological response, or both (n=1).

Anti-idiotypic antibody responses were detected by analysis of pro- and hyper-immune sera in either direct, or competition, ELISA. The immunization with autologous Id protein induced significant titers of anti-idiotypic antibody that either directly bound or inhibited the binding of a murine anti-idiotype monoclonal antibody (anti Id mAb) to Id on the plate. The specificity of the humoral response for the Ig idiotype was demonstrated by the lack of significant binding of hyperimmune serum to a panel of isotype-matched human Igs of unrelated idiotype, or by the lack of significant inhibition of a panel of heterologous Id-anti-Id systems, respectively. Peak humoral responses were obtained after the fifth immunization and persisted for at least nine months. The anti-idiotypic antibody produced by patient 1 was affinity-purified and shown to contain heterogeneous light chains as well as immunoglobulin G heavy chains. This patient's antibody titer was successfully boosted with a single administration of Id-KLH in adjuvant after a decline of the humoral response after 15 months.

Cellular immune responses were measured by the proliferation of PBMC to KLH and to autologous Id separately at concentrations ranging from 1–100 μg per milliliter of soluble protein in five day in vitro cultures. None of the pre-immune PBMC demonstrated any preexisting proliferation to autologous Id above that to culture medium alone. Hyperimmune PBMC from all patients demonstrated strong proliferative responses to the KLH carrier. Of primary interest, significant hyperimmune proliferative responses to Id were detected in five patients. Although their responses were of lower magnitude than parallel responses to KLH, patients 3, 4, 6, 8 and 9 were classified as responders on the basis of reproducible increases in counts-per minute (cpm) $^3$H-thymidine incorporation in wells containing Id, compared with medium alone, that were sustained over multiple time points. Patients demonstrating occasional increases in cpm in wells containing Id compared with medium alone were classified as non-responders (patients 1 and 5).

Flow cytometry analysis of cultures demonstrating proliferation to Id revealed a predominance of cells staining positively for CD4 (>95%), suggesting the phenotype of the responding cell subpopulation. These cultures could be successfully expanded for approximately four weeks by stimulation alternatively with interleukin-2 (IL-2) and Id-pulsed autologous irradiated PBMC as antigen-presenting cells. Specificity of the responses for Ig idiotype was confirmed by the lack of significant proliferation to an isotype-matched human Ig of unrelated idiotype compared with medium alone. Such idiotype-specific PBMC proliferative responses were observed only after the addition of the adjuvant to the program and also persisted for at least 9–14 months.

The ability of the idiotype-specific humoral response to bind autologous tumor cells was also tested. This was shown by the inhibition of binding of a labeled murine anti-idiotype mAb to tumor cells from a pre-treatment lymph-node specimen from patient 8 by hyperimmune, but not by pre-immune, serum from this patient. In addition, affinity purified anti-idiotypic antibodies from the hyperimmune sera of the two other patients who demonstrated idiotype specific humoral responses were demonstrated by flow cytometry to bind autologous tumor.

All patients were also closely monitored for disease activity with physical examinations and routine laboratory and radiographic studies. Of the two patients with measurable tumor at the initiation of Id immunization, one (patient 1) experienced complete regression of a single 2.5 cm left submandibular lymph node, and the other (patient 4) experienced complete regression of a 4.5 cm cutaneous lymphomatous mass on the right arm. This clinical response in patient 4 correlated with an Id-specific, PBMC proliferative response in vivo. Correlating with the duration of their immunological responses, the clinical responses in both patients have continued at 24 and 10 months, respectively, after completion of the immunization series. Moreover, with a median follow up time of 10 months, the only case of tumor recurrence among those patients who were in remission and completed the immunization series occurred in patient 5, who was one of the two patients who failed to demonstrate an idiotype-specific immunological response.

Toxicity was minimal in all twelve patients. All patients experienced transient local reactions characterized by mild erythema, induration, and discomfort, without skin breakdown, at the injection sites. Splitting the components of the vaccine (Id-KLH and adjuvant) in one patient who had experienced a moderate local reaction and in another patient who had experienced a moderate systemic reaction, characterized by fever, rigors and diffuse arthralgias, established the adjuvant as the component associated with these reactions. Both of these moderate reactions resolved completely after 24–48 hours. The only laboratory abnormality associated with Id immunization was a mild elevation (less than twice the normal value) of serum creatine phosphokinase 24 hours after immunization in an occasional case.

These results demonstrate that patients with B-cell lymphoma can be induced to make sustained idiotype-specific immune responses by active immunization with purified autologous tumor-derived surface Ig. They show that autologous Id, made immunogenic by conjugation to KLH, can serve as an immunogen (antigen) to elicit host immunological responses. The induction of low levels of idiotype-specific immunity was demonstrated in the setting of minimal tumor burden following conventional chemotherapy. These results, taken together with the induction of relatively stronger immune responses to the KLH carrier, and exogenous antigen, suggest that chemotherapy-induced irnmunosuppression is not an obstacle to active immunotherapy administered adjunctively to cytoreductive drug therapy in this manner.

This initial study also established the requirement for an immunological adjuvant, as no Id-specific responses were observed prior to the addition of an adjuvant to the program. The objective of further clinical trials using tumor derived Id as a therapeutic vaccine is to further optimize the immunogenicity of this vaccine. To this end, this study will focus on the use of novel immunological adjuvants which are 1) more potent and 2) more effective in the induction of cell-mediated immune responses, compared with the pluronic polymer-based adjuvant used in the study.

The 38C13 B cell tumor is used as a model system to screen promising immunological adjuvants. A number of these have included cytokines and among these, GM-CSF has emerged as a promising adjuvant for idiotypic Ig antigen. In these experiments (10 mice per group), syngeneic mice were immunized with 50 μg Id-KLH derived from the tumor, either alone or in combination with GM-CSF mixed together with the antigen and administered subcutaneously. Three additional daily doses of GM-CSF were administered s.c. as close to the original site of immunization as possible. Mice immunized with an irrelevant Id-KLH (4C5 IgM) served as negative controls for the vaccine. Two weeks after this single immunization, all mice were challenged with a single preparation of 38C13 tumor cells ($5\times10^3$ cells i.p.) and followed for survival. The results demonstrated that the augmented survival benefit afforded by immunization with relevant Id-KLH alone can be significantly enhanced by the addition of GM-CSF at either the 100 or 10,000 unit dose. The loss of this protective effect at a higher dose of GM-CSF of 50,000 units was also observed. These data suggest that GM-CSF may have a potent adjuvant effect in vivo for Id-KLH antigen, especially at relatively low doses.

Current Treatment of Follicular Lymphomas

The follicular lymphomas are follicular small cleaved cell (FSC) and follicular mixed lymphoma (FM). Stage I and II patients comprise only 10% to 15% of all cases of follicular lymphomas and are best managed with radiation therapy. Eight-five percent of patients with follicular lymphomas present with stage III or IV disease. The optimal management of these patients remains controversial and has generally followed two divergent approaches (16, 17). One is an aggressive approach, which has included radiation therapy, combination chemotherapy, or combined modality therapy and the other is a conservative approach that involves no initial treatment followed by a single-agent chemotherapy or involved-field radiotherapy when required (18; 19). Most forms of systemic therapy have the capacity to produce high complete response rates. However, they have failed to produce long-term disease-free survival or to prolong overall survival; thus, it has become clear that the vast majority of patients with this disease will relapse and die of their lymphoma, despite its usually indolent course.

The NCI study (MB-110, BRMP 8903) begun in 1978, is a prospective randomized study comparing these two distinct approaches to the management of stage III or IV indolent histology lymphoma. Most patients were randomized between no initial therapy or aggressive combined modality therapy with ProMACE/MOPP flexitherapy followed by low dose (2400 cGy) total nodal irradiation. Among the 149 patients treated thus far, 125 (84%) were randomized; 62 to watch and wait (W & W) and 63 to aggressive treatment. Among the 62 patients on the watch and wait arm, 29 continue to be observed for periods up to 10+ years. The median time to cross over to aggressive therapy is 23 months.

It is apparent that patients in whom therapy is initiated after the development of symptoms have a significantly lower complete response rate to therapy than patients randomized to receive the same therapy at diagnosis (74% vs 40%, $P_2=0.0039$). The complete responder (CR) rate of patients randomized to initial aggressive treatment is comparable to those obtained in patients with advanced-stage intermediate grade lymphoma receiving the same treatment. The CR rate in indolent lymphoma does not appear to be significantly higher than what can be achieved with other combination regimens. For patients randomized to watch and wait, median follow-up of CRs is shorter because of the delay in initiating treatment. However, the median duration of remission has not been reached at five years and 57% of patients are projected to be disease-free >8 years and 44% are projected to be in a CR at 12 years. The disease-free survival curves are not significantly different between the two arms. Thus, allowing the patient to reach a greater tumor burden before instituting systemic therapy reduces the likelihood of obtaining a CR, but once achieved, CRs are comparably durable to those obtained from primary aggressive therapy. The lengthening of the remission duration, however, has not resulted in a survival advantage for patients randomized to receive primary aggressive chemotherapy. Furthermore, even though a minority of complete responders have relapsed, the probability of relapse appears to be continuous over time, and the vast majority of patients are expected to eventually succumb to their disease.

Thus, even immediate aggressive therapy has not resulted in improved survival. Therefore, although patients diagnosed with follicular lymphoma enjoy relatively longer survival times compared with patients with solid tumors, follicular lymphoma remains an incurable disease. Novel experimental therapies designed to improve the durability of the remissions already effectively induced by chemotherapy are justified.

1.3 Summary of Treatment Plan

The goal is to treat patients with follicular lymphomas to complete remission or maximal response with ProMACE chemotherapy. After the completion of chemotherapy, in an effort to reduce the relapse rate (by eradicating microscopic disease resistant to chemotherapy), patients will receive an autologous Id vaccine administered in combination with GM-CSF.

The goal of this study is to evaluate the ability of the Id vaccine to clear the bone marrow of malignant cells detectable by pathologic (morphologic) examination or molecular examination (polymerase chain reaction, PCR) in patients with PCR amplifiable translocations. All patients have serial bone marrow and peripheral blood samples collected to search for clonal abnormalities by PCR. Patients are followed after vaccine therapy and their remission status correlated with clinical vs. molecular determinations of response. There should be three categories of complete responders: those who had a clinical complete response before the vaccine but had an abnormal clone by PCR that cleared after the vaccine; those with a clinical CR before the vaccine who were also PCR negative before the vaccine; and those who achieved a clinical complete response but had PCR positive marrows before and after the vaccine. It is a goal of this study to assess whether "molecular complete responses" can be achieved using the vaccine in patients following chemotherapy.

2.0 Objectives

The objectives of this trial are to:

2.1 To induce cellular and humoral immunity against the unique idiotype expressed on the surface of patients' B-cell lymphomas.

2.2 To determine the ability of Id immunization to eradicate bcl-2 positive tumor cells from the bone marrow as detected by PCR.

2.3 As a secondary objective, to determine the more biologically active of the two GM-CSF doses as an adjuvant, as measured by the endpoints in 2.1 and 2.2.

2.4 To determine the impact of Id immunization on disease free survival of patients achieving a CR with chemotherapy.

3.0 Patient Selection 3.1 Patient Sample
  A. Sample size, approximately 42 patients
  B. Sex distribution: male and female
  C. Age: patients must be $\geq 18$ years old 3.2 Eligibility Criteria
  Patient must meet all of the following eligibility criteria:
  A. Tissue diagnosis of: follicular small cleaved cell, or follicular mixed lymphoma with surface IgM, IgG or IgA phenotype with a monoclonal heavy and light chain. Pathology slides must be submitted to the NIH Pathology Department for review.
  B. Stage III or IV lymphoma.
  C. Only previously untreated patients are eligible.
  D. Previous treatment with radiation alone (less than TBI) is permissible.
  E. A single peripheral lymph node of at least 2 cm size accessible for biopsy/harvest.
  F. Karnfsky status $\geq 70\%$.
  G. Life expectancy of >one year.
  H. Serum creatinine $\leq 1.5$ mg/dl unless felt to be secondary to lymphoma.
  I. Bilirubin $\geq 1.5$ mg/dl unless felt to be secondary to lymphoma or Gilbert's disease. SGOT/SGPT<3.5× upper limit of normal.
  J. Ability to give informed consent. Ability to return to clinic for adequate follow-up for the period that the protocol requires.

3.3 Patient Exclusion Criteria
  The presence of any exclusion criteria (listed below) will prohibit entry into study:
  A. Prior total body irradiation.
  B. Presence of antibodies to HIV, hepatitis B surface antigen or other active infectious process.
  C. Pregnancy or lactation. Fertile men and women must plan to use effective contraception. A beta-HCG level will be obtained in women of childbearing potential.
  D. Patients with previous or concomitant malignancy, regardless of site, except curatively treated squamous or basal cell carcinoma of the skin, or effectively treated carcinoma in situ of the cervix.
  E. Patient unwilling to give informed consent.
  F. Failure to meet any of the eligibility criteria in Section 3.2.
  G. Any medical or psychiatric condition that in the opinion of the protocol chairman would compromise the patient's ability to tolerate this treatment.
  H. Patient with CNS lymphoma (current or previously treated) will not be eligible.

4.0 Clinical Evaluation 4.1 Complete history and physical examination.
4.2 CBC, diff., platelet count.
4.3 Serum chemistry, $\beta_2$-microglobulin.
4.4 PT/PTT
4.5 Quantitative immunoglobulins, serum protein electrophoresis, immunoelectrophoresis.
4.6 HIV antibody, HBsAg.
4.7 Urinalysis.
4.8 Serum $\beta$-HCG in women of child-bearing potential.
4.9 EKG and MUGA.
4.10 5 TT for serum storage.
4.11 Leukapheresis to obtain $3 \times 10^9$ lymphocytes. These samples will be used for baseline studies of T-call activation and response to Id.
4.12 Tumor Biopsy—prior to therapy, all patients must undergo biopsy/harvest of a clinically involved peripheral lymph node to obtain tissue for morphological classification, immunophenotypic characterization, determination of immunoglobulin gene rearrangements, bcl-2 translocation, cytogenetics, and to provide starting material for an Id vaccine. The sample should be at least 2 cm in size. Only patients with tumors that are surface immunoglobulin positive with a monoclonal heavy and light chain will be accepted as study candidates. Use standard lymphoma vaccine biopsy orders. See section 11.1 of protocol. Leftover tumor biopsy samples may be used for basic studies of lymphoma biology in vitro. Such future studies may be done without reconsenting the subjects only if the studies involve risks already outlined in the original consent form.
4.13 CXR—PA and LAT.
4.14 CT scan of abdomen and pelvis.
4.15 Lymphangiogram, unless contraindicated by massive pedal edema, severe chronic lung disease, ethiodal sensitivity (Note: sensitivity to other iodine compounds, e.g., renograffin, are relative, but not absolute contraindications).
4.16 Other tests (CT chest, ultrasound, liver scan, bone scan, upper and lower GI series, IVP, MRI) should be performed as needed to evaluate all disease sites adequately.
4.17 Examination of pleural fluid or ascites when present.
4.18 Bilateral bone marrow aspirates and biopsies—In addition to the normal aspirate and biopsy, 5 cc of marrow will be aspirated from each side into 0.5 ml of PFH for PCR analysis. The procedure should be performed in the usual manner with a biopsy performed first. Then a small volume (0.5–1 cc) can be aspirated for the smear and clot tube. A separate Rosenthal needle with bevel should be used for the aspirate. The 5 cc sample for PCR can be obtained from the same site as the initial aspirate.
4.19 CT scan of the head and lumbar puncture with CSF analysis if clinically indicated.

5.0 Patient Registration 5.1 Patients will be registered prior to the initiation of therapy at which time eligibility criteria will be reviewed. Stratification and randomization are described in detail in Section 15.0 Statistical considerations.

6.0 Study Design
(See Schema)

6.1 ProMACE

| Day 0 | Day 7 | Day 28 |
|---|---|---|
| Cyclophosphamide 650 mg/m² IV | Cyclophosphamide 650 mg/m² IV | Next cycle begins |
| Doxorubicin 25 mg/m² IV | Doxorubicin 25 mg/m² IV | |
| Etoposide VP-1 6 120 mg/m² IV | Etoposide BP-1 6 120 mg/m² IV | |
| Prednisone 60 mg/m² po qd × 14 (days 0 to 13) | | |
| Bactrim one double strength tablet po BID throughout therapy | | |

6.1.1 All patients will be treated until a complete remission is obtained and two additional cycles of chemotherapy have been given, or until disease has been stable for two cycles of chemotherapy, or progressive disease develops. A minimum of six cycles will be given to each complete responder before therapy is discontinued. Patients with more than 90% PR or a full CR will be continued on the vaccination part of the protocol. Patients with less than 90% PR or progressive disease will be taken off of the study.

6.2 Postinduction Therapy—Three to six months (or whenever a customized GMP vaccine is available, up to a maximum period of 12 months) after the completion of chemotherapy, all patients in whom either a complete clinical remission or minimal disease status (≧90% partial response) has been achieved will receive a series of five injections of a vaccine consisting of 0.5 mg autologous tumor derived immunoglobulin (Id) conjugated to KLH. The vaccine will be administered together with GM-CSF as an immunological adjuvant. Both the vaccine and GM-CSF will be administered subcutaneously according to the following schedule:

| Schedule: | At 0, 1, 2, 3 and 5 months |
|---|---|
| | Id-KLH (0.5 mg s.c.) day 0 |
| | adjuvant (s.c.) days 0–3 |
| Cohort 1: | GM-CSF 500 mcg/m²/d s.c. for 4 days |
| Cohort 2: | GM-CSF 100 mcg/m²/d s.c. for 4 days |

The sites of injection will be rotated between the upper and lower extremities. Each dose of vaccine or GM-CSF will be split equally between the two upper or lower extremities. All GM-CSF injections will be given in close proximity to the vaccination site, as close to the exact site of injection as possible. If local reactions to GM-CSF are severe, GM-CSF injections may be given elsewhere. Patients will be observed in the clinic for two hours following Id-KLH and/or GM-CSF administration. During the observation period, vital signs will be taken every 15 minutes during the first hour and every 30 minutes during the second hour.

7.0 Supportive Care 7.1 G-CSF 5 mcg/kg/d SC may be used in all patients who are hospitalized for the treatment of febrile neutropenia, regardless of how long the neutropenia persists.

8.0 Grading and Management of Toxicity 8.1 Chemotherapy: Dose modification of chemotherapy will be based on the granulocyte count done at the time of drug administration (day 0 or 7 of each cycle). The percentage of drugs administered may be further modified based on toxicity in prior cycles (see below). If the granulocyte count is <1200, and the patient is due for day 0 drugs, delay day 0 for one week until appropriate parameters are met. In general, delays of up to one week are preferable to starting G-CSF. If after a one week delay, appropriate parameters are still not met, then G-CSF may be started as above. Also, in general, delays of up to one week are preferable to dose reductions. Full doses of all drugs should be given on time if blood count suppression is due to bone marrow involvement with disease.

8.1.1 Dose Modification for Hematologic Toxicity

| IF GRANULOCYTE COUNT IS: On Day 0 | THEN DOSE AS FOLLOWS: |
|---|---|
| ≧1200 | 100% all drugs |
| ≦1200 | Day 0 Delay |

For neutrophil nadir <500 or platelet count <25,000 on previous cycle, 75% of cyclophosphamide, doxorubicin, and etoposide should be considered. For neutrophil nadir (day 21 counts) >750 on a previous cycle, dose escalation of cyclophosphamide, doxorubicin, and etoposide by 10–20% should be prescribed.

| IF PLATELET COUNT IS: | THEN DOSE AS FOLLOWS |
|---|---|
| >100,000 | 100% of all drugs |
| 50–99,999 | 100% Prednisone |
| | 75% Etoposide |
| | 50% Cyclophosphamide, Doxorubicin |
| <50,000 | Delay |

8.1.2 Dose Modification for Non-hematologic Toxicity 8.1.2.1 Assessment of non-hematologic toxicity will be graded according to the CRB/DCS/NCI Common Toxicity Criteria. Chemotherapy will be withheld in patients experiencing grade 2 or greater non-hematologic toxicity until the patient has completely recovered from the toxicity. For nausea/vomiting 2: grade 2, drug therapy should be continued with non-steroid antiemetics.

8.1.2.2 Doxorubicin dosage should be adjusted as follows in the presence of the following LFT abnormalities:

| % Dose | Bilirubin | SGOT |
|---|---|---|
| 100 | <1.5 mg/dl | <75 U |
| 50 | 1.5–2.9 mg/dl | 75–150 U |
| 25 | 3.0–5.9 mg/dl | 151–300 U |
| 0 | ≧6.0 mg/dl | >300 U |

8.2 Immunotherapy 8.2.1 Id-KLH Vaccine

Based on previous experience with autologous Id-KLH vaccines, little or no toxicity is expected from the Id-KLH component of the vaccine (15). Nevertheless, any local skin reactions will be carefully noted and scored for erythema, induration, pain and disruption of the barrier surface. If any patient has a reaction suggestive of sensitization, the vaccine may be split into its component parts; specifically, the patient will be tested with Id-KLH alone and then GM-CSF alone. Toxicities will be graded according to the CRBINCI/DCS common toxicity criteria.

8.2.2 GM-CSF

Anticipated toxicities from GM-CSF administration in this dose range are expected to be mild based on previous experience. Potential toxicities include fever, chills, myalgias, arthralgias, nausea, vomiting, diarrhea, dyspnea, tachycardia, arrhythmias, elevation of liver function tests, elevation of BUN and creatinine. However, local skin reactions, such as erythema and induration, may be observed and will be carefully noted. Attempts will be made to maintain these patients as outpatients. For grade IV fever (not responsive to Indocin or Tylenol), or grade III vomiting (unresponsive to therapy), GM-CSF will be held until toxicity is less than grade II and will be restarted at 50% of the original dose level for the rest of that weekly injection cycle and for subsequent cycles. For neurologic toxicity that affects daily function (unable to carry on simple routine duties, or grade II in the toxicity grading scale), hold treatment until symptoms resolve, then reduce GM-CSF by 50%. If symptoms persist, the adjuvant should be removed for subsequent immunizations. Patients with grade III neurotoxicity will be removed from the study.

For well-documented evidence of cardiac toxicity (i.e., grade III, including evidence of ischemia or ventricular arrhythmia, but not supraventricular tachycardia or atrial fibrillation controlled by digoxin or calcium channel blocking agents), the adjuvant will be removed for subsequent immunizations.

Asymptomatic elevations in serum bilirubin and creatinine (not resulting in hyperkalemia) will be tolerated. For SGOT or SGPT>10×normal, GM-CSF will be held until values return to <5×normal, then resumed at 50% of the GM-CSF dose for all remaining doses.

8.2.3 Fever and chills associated with vaccine administration and/or GM-CSF will be treated with TYLENOL and/or DEMEROL. The use of non-steroidal antiinflammatory drugs and/or steroids should be avoided. Should non-steroidals or steroids be required for unrelated medical conditions for a course exceeding 2 weeks, the patient will be taken off of the study.

9.0 Adverse Drug Reactions 9.1 All toxicities and adverse events will be recorded on the study flow sheet and appropriately graded as to severity and cause. Toxicities that are related to the underlying disease should be clearly differentiated from drug toxicities.

9.2 Adverse drug reactions related to chemotherapy will be submitted based on guidelines for commercial drugs.

9.3 Reports of adverse reactions to Id-KLH and GM-CSF will be made using the Division of Cancer Treatment Common Toxicity Criteria for reference according to the guidelines published by the DCT, NCI. These guidelines can be summarized as follows:

A. Report by telephone to IDB within 24 hours (301) 230-2330
  1. All life-threatening events (grade 4, except for grade 4 myelosuppression) which may be due to administration of the investigational drug(s),
  2. All fatal events (grade 5),
  3. All first occurrences of any previously unknown toxicity (regardless of grade).
B. A written report should follow within 10 working days.
C. All adverse drug reactions will also be reported in writing to the NCI Institutional Review Board within 10 working days.
D. All adverse drug reactions will also be reported to the FDA in accordance with Federal regulations.
E. Data will be submitted at least every two weeks.

10. Study Parameters 10.1 During Chemotherapy
  10.1.1 Weekly: CBC, diff. platelets; except day 14, i.e. CBC on day 0, 7,21, and 28.
  10.1.2 Beginning of each cycle: Chem 20, CXR, LAG follow-up (KUB), CT scans (only after 4 cycles, then every 2 cycles).
  10.1.3 Bilateral bone marrow aspirate and biopsy after four cycles and every additional two cycles thereafter. Include 5 cc of aspirate in PFH from each side for PCR analysis.

10.2 At Maximal Response to Chemotherapy
  10.2.1 If residual disease is obvious, record measurements and perform bone marrows as above.
  10.2.2 For complete responders, complete restaging should be performed. This should include all studies that were positive at initial staging evaluation with the exception of repeat thoracotomy or laparotomy. Bilateral bone marrows should be performed as above.

10.3 During Vaccine Therapy
  10.3.1 If residual disease is obvious, record measurements and perform bone marrows as above.
  10.3.2 PT-PTT day 0
  10.3.3 UA, $\beta_2$ microglobulin day 0 of each immunization.
  10.3.4 Leukapheresis is performed on the day of initiation of vaccine therapy (prior to the first cycle only) to obtain pre-vaccine lymphocytes for storage. Five tiger top tubes are drawn at this time to obtain serum for storage.
  10.3.5 Two tiger top tubes and peripheral blood (60 cc in PFH) are collected on day 0 of each monthly cycle, for preparation of serum and lymphocytes, respectively.
  10.3.6 Skin Biopsy is obtained near a planned immunization site on day 0 prior to the first cycle (baseline sample) and again on day 1, 2, or 3 of cycle 3 at an active site of erythema and/or induration as close to the original biopsy site as possible.
  10.3.7 DTH—Delayed type hypersensitivity test (DTH) to autologous idiotype protein is performed during cycle 4 and again following completion of the immunization regimen, i.e., during or after cycle 5. The DTH-test is performed by intradermal injection of 0.5 mg of idiotype protein in 0.1–0.2 ml of NS. To ascertain the specificity of a positive reaction, 0.5 mg of a heterologous isotype matched Id-protein (from another patient on the same study) in the same volume will be used as a negative control.

The control idiotypes used on these two occasions will be from two different patients, also in the study, in order to minimize the possibility of eliciting an immunologic response against a particular irrelevant idiotype.

A skin biopsy will also be obtained at the site of the intradermal injection of idiotype protein and at the control site, one to three days, after the intradermal injections.

10.3.8 Fine needle aspiration or core biopsy (with or without CT guidance) of any enlarged lymph node draining the vaccination sites is performed to obtain lymphocytes for in vitro assays.

10.4 At Discontinuation of Vaccine 10.4.1 Restaging as described for Chemotherapy in Section 10.2.

10.4.2 Bilateral bone marrow aspirates and biopsies at completion of therapy and every six months for two years after completing therapy and yearly thereafter.

10.4.3 10 cc of serum for storage and 60 cc of peripheral blood in PFH is collected at completion of therapy and every three months for a year.

11.0 Specimen Processing and Immunological Assays 11.1 Lymph Node Harvest/Biopsy Each lymph node biopsy will be divided as follows: (a) one-third of the specimen will be sent in saline to the Hematopathology Section, Laboratory of Pathology, NIH. Biopsies are processed for routine histopathy and for immunophenotypic characterization, particularly with respect to monotypic heavy and light chain expression; and (b) two-thirds of the specimen is sent in sterile saline in a sterile container to Clinical Immunology Services, NCI FCRDC, where it is processed into a single-cell suspension and cryopreserved.

11.2 Blood and Bone Marrow Samples

All peripheral blood and bone marrow aspirate samples are sent in an expedited manner to Clinical Immunology Services, NCI-FCRDC. Tiger top tubes are spun down and serum divided into 1 ml aliquots for frozen storage. Peripheral blood mononuclear cells (PBMC) are isolated prior to freezing by Ficoll-hypaque centrifugation using standard protocols.

11.3 Assay for Serum Antibody

In a direct enzyme-linked immunosorbent assay (ELISA), preimmune and hyperimmune serum samples from each patient are diluted over wells of a microtiter plate that are coated with either autologous immunoglobulin idiotype or a panel of isotype-matched human tumor immunoglobulins of unrelated idiotype. Bound antibody is detected with horseradish peroxidase-goat antihuman light-chain antibodies directed against the light chain not present in the immunoglobulin idiotype (Caltag Laboratories, South San Francisco).

11.4 Assay for Idiotype-Specific Proliferative Response

Whenever feasible, fresh PBMC, isolated above, are used on the same day they are obtained. Stored frozen PBMC are available as a back-up. PBMC are washed and plated at a concentration of $4\times10^5$ cells per well in Iscove's modified Dulbecco's medium (IMDM) with 1 percent human AB7 serum (IMDM-1 percent AB). KLH, autologous immunoglobulin idiotype, or a panel of isotype matched immunoglobulins of irrelevant idiotypes at concentrations of 0 to 100 µg per milliliter in IMDM-1 percent AB preparation are added in triplicate. After the cells are incubated for three days at 37° C. in an atmosphere containing 5 percent carbon dioxide, they are transferred to a preparation of IMDM and 5 percent fetal-.calf serum containing recombinant interleukin-2 (30 U per milliliter). The plates are incubated for two days and pulsed for 16 to 20 hours with $^3$H-labeled thymidine (1 µCi per well). Data are expressed as mean (±SEM) counts per minute of [$^3$H]thymidine incorporation. Initial five-day cultures of PBMCs established as described above are expanded in IMDM-5 percent fetal-calf serum containing interleukin-2 (30 U per milliliter). Harvested cells are replaced in IMDM-1 percent AB containing autologous immunoglobulin idiotype and fresh irradiated (5000 R) autologous PBMCs ($4\times10^5$ cells per well) as antigen-presenting cells for five days, before pulsing with $^3$[H]thymidine.

11.5 Cytotoxicity Assays

The potential cytotoxicity of PBMC cultured with Id as above, or with irradiated fresh cryopreserved tumor cells, is assayed against either autologous lymphoblastoid cell lines (LBL) pulsed with Id or fresh cryopreserved tumor targets. Autologous LBL pulsed with soluble antigen have been used successfully as targets to detect gp160-specific cytotoxic T-lymphocytes (20). Historically, the inability to establish long-term cultures of follicular lymphoma has hindered their availability as targets. However, two recent reports have described the use of fresh cryopreserved lymphoma cell targets, with levels of spontaneous incorporated radioisotope release in the acceptable range of <35% (21–22). Standard four hour $^{51}$Cr release, as well as 18–24 hour $^{111}$In release assays are used.

Autologous LBL are prepared from pre-immune PBMC by the AIDS Monitoring Laboratory, NCI-FDRDC, using published methods.

11.6 Monitoring of T-cell Receptor (TCR) Status

Pre-chemotherapy and pre- and postimmunization serum samples are assayed for TCR status by Western blot assay. Approximately $7\times10^6$ purified T-cells from PBMC are lysed for 5 minutes at 4° C. in lysis buffer (25 mM Tris, pH 7.4 [Sigma Chemical Co., St Louis, Mo.], 300 mM NaCl, 0.05% Triton X-100, 1 mM Na orthovanadate, 10 µg/ml aprotinin, 10 µg/ml leupeptin, 10 mM nitrophenol-guanidine benzoate [NPGB] and 5 mM EDTA). The lysates are centrifuged at 12,000 rpm at 4° C. for 5 minutes and supernatant is removed with a micropipettor, making sure the nuclear pellet is not disturbed. A sample of the supernatant is then used to quantitate protein using the BCA protein assay (Pierce, Rockford, Ill.). The rest of the lysate is boiled with 3× reducing sample buffer for 5 minutes and placed on ice before its use in Western blot.

Varying concentrations of cellular lysate ranging between 1 and 30 µg are electrophoresed in 14% Tris-glycine gels (Novex Experimental Technology, CA) under reducing conditions and then transferred to Imobilon-p PVDF transfer membranes (Millipore Co., Bedford, Mass.). The membranes are incubated with a 5% solution of non-fat dried milk for one hour and then blotted for one hour at room temperature with anti-TCRζ anti-serum (Onco-Zeta 1, OncoTherapeutics, Cranbury, N.J.) at a 1:2000 dilution. The membranes are washed with TBS-T buffer [1 M Tris base, 5M NaCl, 0.1% Tween 20 (pH 7.5)] and incubated with anti-rabbit or anti-mouse Ig horseradish peroxidase (Amersham, Buckinghamshire, UK). After washing with TBS-T, the membranes are developed with the chemiluminescence kit ECL (Amersham, UK) for 1–5 minutes. X-OMAT AR film (Kodak Co., Rochester, N.Y.) is used to detect the chemiluminescence.

11.7 PCR Amplification of Rearranged bcl-2

Nested oligonucleotide amplification is performed at the MBR or mcr of the bcl-2/Ig$_H$ hybrid gene using previously published methods (23). Briefly, samples containing 1 μg of genomic DNA are initially amplified for 25 cycles in a final volume of 50μg containing 50 mmol/L KCl, 10 mmol/L Tris HCL, 2.25 mmol/L MgCl$_2$, 200 mmol/L oligonucleotide primers, 200 mmol/L each of dGTP, dCTP, dTTP and dATP, and 1.5 U Taq polymerase(Cetus, Emeryville, Calif.). Reamplification of an aliquot of product is performed for 30 cycles in a final volume of 50 μl using identical conditions to the original amplification, with oligonucleotide primers internal to the original primers. Aliquots of the final product are analyzed by gel electrophoresis in 4% agarose gels containing ethidium bromide and visualized under UV light. DNA is Southern blotted onto Zeta-probe blotting membrane (BioRad. Richmond, Calif.) and bcl-2-specific DNA is detected by hybridization with oligonucleotide probes radiolabeled with $^{32}$P(ATP) using T4 polynucleotide kinase.

12.0 Removal of Patients From Protocol Therapy

Patients will be removed from protocol for any of the following reasons:

12.1 Unacceptable toxicity (as defined in Section 8.0).
12.2 The patient declines further therapy.
12.3 The patient experiences progressive lymphoma.
12.4 It is deemed in the best interest of the patient. In this instance,
   12.4.1 The Principal Investigator should be notified.
   12.4.2 The reasons for withdrawal should be noted in the flow sheet.

13.0 Response Criteria

Patients will be reevaluated for tumor response after every two cycles of chemotherapy using the following criteria:

13.1 Complete Response—disappearance of all clinical and laboratory (excluding PCR) signs and symptoms of active disease for a minimum of one month.
13.2 Partial Response—a 50% or greater reduction in the size of the lesions as defined by the sum of the products of the longest perpendicular diameters of all measured lesions lasting for a minimum of one month. No lesions may increase in size and no new lesions may appear.
13.3 Minimal Residual Response—a ≧90% partial response. For most patients in this category, this will mean ≦10% residual bone marrow involvement by lymphoma.
13.4 Progressive Disease—an increase of 25% or more in the sum of the products of the longest perpendicular diameters of all measured indicator lesions compared to the smallest previous measurement or the appearance of a new lesion.

14.0 Drug Formulation and Toxicity Data 14.1 Cyclophosphamide (CTX, Cytoxan)-NSC #26271
  14.1.1 Source and Pharmacology—CTX is an alkylating agent, related to nitrogen mustard, which is biochemically inert until it is metabolized to its active components by the liver phosphoramidases. It is non-phase-specific. The drug is excreted exclusively by the kidney after parenteral administration.
  14.1.2 Formulation and Stability—CTX is supplied as a 100, 200, 500, 1000 mg and a 2 gram lyophilized powder with 75 mg mannitol per 100 mg (anhydrous) cyclophosphamide. The vials are stored at room temperature (59–86° F.) and reconstituted with sterile water for injection to yield a final concentration of 20 mg/ml as described in the package insert. Reconstituted cyclophosphamide is stable for at least 6 days under refrigeration and for 24 hours at room temperature. Reconstituted drug and diluted solutions should be stored under refrigeration.
  14.1.3 Supplier—Commercially available.
  14.1.4 Route of Administration—The cyclophosphamide used in this regimen is given IV over 30 minutes and is diluted in 100 cc of either D$_5$W or NSS.
  14.1.5 Toxicity—Toxicities described with cyclophosphamide include nausea, vomiting, myelosuppression, gonadal failure in both males and females, alopecia, interstitial pneumonitis, pulmonary fibrosis, hemorrhagic cystitis, cardiac events (cardiomyopathy), syndrome of inappropriate antidiuretic hormone secretion (SIADH) and rarely, anaphylaxis.

14.2 Prednisone (Deltasone, Meticorten, Liquid Pred) NSC #10023
  14.2.1 Source and Pharmacology—Prednisone is the synthetic congener of hydrocortisone, the natural adrenal hormone. It binds with steroid receptors on the nuclear membrane, blocks mitosis, and inhibits protein synthesis. It kills primarily during the S-phase of the cell cycle. It is catabolized in the liver and excreted in the urine. Peak blood levels occur within two hours after oral intake.

Plasma half-life is 3–6 hours. (Biologic half-life is 12–30 hours.)

| Cortisone | 25 | |
| --- | --- | --- |
| Hydrocortisone | 20 | Equivalent |
| Prednisone | 5 | strength in mg |
| Decadron | 0.75 | |

14.2.2 Formulation and Stability—Available in 1, 2.5, 5, 10, 20 and 50 mg tablets; 5 mg/5 ml liquid.
  14.2.3 Supplier—Prednisone is commercially available.
  14.2.4 Route of Administration—PO; NOTE: May cause GI upset; take with meals or snacks. Take in the morning prior to 9 a.m.
  14.2.5 Toxicity—Toxicities described with prednisone include fluid and electrolyte changes, edema, hypertension, hyperglycemia, gastritis, osteoporosis, myopathy, behavioral and mood changes, poor wound healing, and Cushing's syndrome (moon face, buffalo hump, central obesity, acne, hirsutism and striae).

14.3 VP-16 (Etoposide.VePesid) NSC #141540
  14.3.1 Source and Pharmacology—VP-16 is a semi-synthetic derivative of podophyllotoxin which inhibits toposomerase II and functions as mitotic inhibitor, but does not bind microtubules. Its main effect appears to be in the S and G$_2$-phase of the cell cycle.

The mean terminal half-life is 11.5 hours, with a range of 3 to 15 hours. It is primarily excreted in the urine.

14.3.2 Formulation and Stability—VP-16 is supplied in vials containing either 100 or 500 mg of etoposide (20 mg/ml) in a polyethylene vehicle. VP-16 is diluted in either 500 cc of 5% dextrose or 0.9% Sodium Chloride Injection. Diluted solutions (concentrations of 0.2, 0.4 mg/ml and 1 mg/ml) are stable for 96, 48 hours and 2 hours, respectively at room temperature under normal room fluorescent light in both glass and plastic containers. Do not refrigerate etoposide-containing solutions.

14.3.3 Supplier—VP-16 is commercially available.

14.3.4 Route of Administration—Etoposide is administered as an IV infusion over 60 minutes.

14.3.5 Toxicity—Toxicities described with etoposide administration include myelosuppression (neutropenia), nausea, vomiting, mucositis, allergic reactions characterized by anaphylactic symptoms and hypotension and alopecia.

14.4 Doxorubricin (Adriamycin) NSC #123127

14.4.1 Source and Pharmacology—Doxorubicin is an anthracycline antibiotic isolated from cultures of *Streptomyces peucetius*. It binds to DNA and inhibits nucleic acid synthesis, with its major lethal effect occurring during the S-phase of the cell cycle. Since it is primarily excreted by the liver, any liver impairment may enhance toxicity. Some of the drug has a very short $\alpha T$ ½ of <20 minutes and $\beta$ ½ of 17 hours. Animal studies indicate cytotoxic levels persist in tissue for as long as 24 hours. Biliary excretion also is a source of elimination for Doxorubicin; therefore, patients with hyperbilirubinemia/cholestasis caused by something other than lymphoma should have dosage modification.

14.4.2 Formulation and stability—Doxorubicin is available as a freeze-dried powder in 10, 50 and 150 mg vials. The drug is stored at room temperature, protected from light, and is reconstituted with sodium chloride 0.9% (NSS) to yield a final concentration of 5 mg/ml. The reconstituted solution is stable for 7 days at room temperature (15–30° C.) or if stored under refrigeration (2–8° C.).

14.4.3 Supplier—Doxorubicin is commercially available.

14.4.4 Route of Administration—Doxorubicin is given as a slow IV injection over 5–7 minutes through an established line with a free flowing IV. Special precautions: Avoid extravasation and local contact with skin or conjunctiva.

14.4.5 Toxicity—Toxicities described with doxorubicin administration include myelosuppression, nausea, vomiting, mucositis, stomatitis, alopecia. diarrhea, facial flushing, dose-related congestive cardiomopathy, arrhythmias, vein streaking (hypersensitivity reaction), radiation-recall dermatitis, local cellulitis, vesication and tissue necrosis upon extravasation (SQ and dermal necrosis).

14.5 ID-KLH Vaccine 14.5.1 Source—Idiotype protein from the individual B cell lymphomas is obtained from tissue culture, purified, and covalently coupled to keyhole limpet hemocyanin (KLH) as previously described. Each batch is produced according to Good Manufacturing Practices standards and tested for sterility, endotoxin contamination, and general safety prior to its use in any patient. The preparation and quality control/quality assurance testing of the Id-KLH conjugate is performed by TSI Washington under CRB contract. The IND for the Id-KLH vaccine will be held by the Drug Regulatory Affairs Section, CTEP.

14.5.2 How supplied—Formulated product for subcutaneous administration contains 0.5 mg of Id and KLH each per ml of normal saline. Id-KLH is supplied as a 1 ml vial.

14.5.3 Storage—Prior to administration, Id-KLH is stored at –20° C.

14.5.4 Administration—After thawing and gentle agitation, the vial contents are drawn up using an 18-gauge needle on a syringe. After the entire contents have been drawn up, the 18-gauge needle is replaced by a 25-gauge needle for injection. This procedure is important to ensure that all particulates (normal components of this vaccine) are obtained from the vial.

14.5.5 Toxicity—Toxicities described with Id-KLH vaccine administration include local site reactions (erythema, induration, swelling and tenderness), fever,chills, rash, myalgias and arthralgias. Mild elevations in creatinine phosphokinase (CPK) have been observed.

14.6 GM-CSF (Sargramostim: NSC #613795; BB-IND 2632

14.6.1 Source and Pharmacology—The GM-CSF used in this study is glycosylated, recombinant human GM-CSF. This GM-CSF is an altered form of the native molecule; the position 23 arginine has been replaced with a leucine to facilitate expression of the protein in yeast (*Saccharomyces cerevisiae*).

14.6.2 Formulation and Stability—The GM-CSF is formulated as a white lyophilized cake and is provided in vials containing 500 $\mu$g of the GM-CSF protein as well as 10.0 mg of sucrose, 40.0 mg of mannitol, and 1.2 mg of Tris (Trimethamine).

To prepare a vial of GM-CSF for direct subcutaneous use, aseptically inject 1.0 ml of Sterile Water for Injection, USP, into the vial to dissolve the lyophilized cake. The diluent should be directed against the side of the vial to avoid excess foaming. Avoid vigorous agitation of the vial; do not shake. This yields a solution containing 500 $\mu$g/ml. The unreconstituted material should be kept refrigerated at 2–8° C. and is stable for at least eighteen months. Once reconstituted, the solution is stable for at least 24 hours at 2–8° C. or at 18–25° C. Because the product does not contain a preservative, vials should be treated as unit-dose containers; reconstituted solution should be held at 2–8° C. and discarded after no more than six hours. Do not freeze GM-CSF.

14.6.3 Supplier. Manufactured by Immunex.

14.6.4 Route of Administration—The appropriate total dose is withdrawn into and administered from a plastic tuberculin syringe. The GM-CSF is injected subcutaneously as close as possible to the Id-KLH injection site. All GM-CSF doses for each patient are administered by the nursing staff in the outpatient unit.

14.6.5 Toxicity—Toxicities described in patients receiving GM-CSF include: fever, chills, diaphoresis, myalgias, fatigue, malaise, headache, dizziness, dyspnea, bronchospasm, pleural effusion, anorexia, indigestion, nausea, vomiting, diarrhea, injection site tenderness, urticaria, rash, pruritus, hypersensitivity reaction, bone pain, thromboembolic events, phlebitis, hypotension, peripheral edema, leukocytosis, thrombocytosis or thrombocytopenia, hepatic enzyme abnormalities, and bilirubin elevation. The first administration of GM-CSF has provoked a syndrome of dyspnea and hypotension within two hours after GM-CSF injection in a single patient receiving yeast-derived GM-CSF; this type of reaction has more frequently been observed in patients receiving GM-CSF produced in *E. coli*. One report of a vascular leak-like syndrome occurring after autologous bone marrow transplant in a patient receiving continuous IV infusion of GM-CSF has been recorded.

14.7 Unconjugated Lymphoma Immunoglobulin Idiotype (for intradermal skin testing) NSC #684151

14.7.1 Source—The patient-specific purified idiotype protein, previously produced according to GMP standards as described above in 14.5, is vialed as a separate product by TSI Washington Laboratories and will be supplied by CTEP, DCT, NCI. This vialed product is tested separately for sterility, endotoxin, and mycoplasma, according to IND specifications previously discussed with the FDA. Each vial of patient-specific unconjugated idiotype will be labeled to include the following information:
Purified sterile immunoglobulin idiotype
patient-specific lot
final volume and concentration of product
patient-specific immunoglobulin subtype
storage conditions
fill date
patient identification (first name/last initial)

14.7.2 How Supplied—This product is available as a solution containing 0.2–0.3 ml of unconjugated idiotype diluted in sodium chloride 0.9%. The solution is contained inside a sterile vial. The final solution contains 0.5 mg of patient-specific immunoglobulin idiotype protein. Intact vials are stored at −20° C.

14.7.3 Toxicity—The toxicities associated with administration of unconjugated Id protein are anticipated to be identical to those described with the Id-KLH vaccine.
The safety issues regarding the injection of heterologous idiotype protein isolated from other patients' B-cell tumors have already been fully addressed in CRB #9407 (NCI T94-0085; Active immunization of Healthy Sibling Marrow Transplant Donors With Myeloma-derived Idiotype) and are felt to be minimal, because of the highly purified nature of the protein. Briefly, an immune response of any consequence to the isotype matched idiotype used as a negative control during the second skin test is not likely, based on:
1. The isotype matched idiotype will only be administered once and is not conjugated to a carrier protein. These minimize the chance of eliciting a sustained immune response to the protein.
2. Any immune response specifically directed against the idiotype (i.e., variable region) on the control idiotype protein is not likely to cross-react with host cells and is therefore not likely to be of any consequence.
3. An autoimmune response against constant region or allotype determinants shared between the idiotype of the patient's own tumor and that of the control idiotype tumor is theoretically possible. However no evidence of such autoimmune responses have been observed either in vivo or in vitro during the course of immunization of sibling bone marrow transplant donors with purified myeloma protein.

Furthermore, a safety precedent exists for immunizing patients with material derived from tumor cells from other patients. For example, in attempting to develop immune responses against metastatic melanomas, patients were immunized with 1) intact melanoma cells; 2) shed antigens fractionated by detergent treatment and ultracentrifugation; 3) melanoma cells infected with vaccinia virus and melanoma cells freeze thawed and mechanically disrupted, all using a pool of allogeneic melanoma cell lines (24–28).

14.8 Bactrim will be supplied by the Clinical Center.

14.9 Filgrastim (G-CSF)/Neupogen 14.9.1 Source and Pharmacology—The G-CSF to be used in this study is the recombinant methionyl human granulocyte-colony stimulating factor (r-methi-HuG-CSF). G-CSF is a hematopoietic growth factor with effects on both immature bone marrow progenitors and mature myeloid cells. It acts by supporting growth of human bone marrow derived colony forming units and enhancing neutrophil growth and proliferation.

14.9.2 Formulation and Stability—The G-CSF is formulated as a clear, sterile solution and is provided in vials at a final concentration of 300 mcg/ml. The commercial vials are available in 300 and 480 mcg sizes. The intact vials are stored under refrigeration (2–8° C.) prior to use and must not be frozen and are stable at this temperature for at least one year.

14.9.3 Supplier—Manufactured by Amgen; supplied by the Clinical Center.

14.9.4 Route of Administration—The appropriate total dose is withdrawn into and administered from a plastic tuberculin syringe. The G-CSF is injected as a subcutaneous injection. The patient or other caregiver is instructed on proper injection technique.

14.9.5 Toxicities—Toxicities described with G-CSF include: transient bone pain (sternal/pelvic) myalgias, fatigue, mild elevations in uric acid, LDH and alkaline phosphate, fluid retention, transient hypotension, local inflammation at injection site, rarely cutaneous vasculitis, rarely pericardial effusion and rare anaphylactic reactions with first dose.

15.0 Statistical Considerations

Statistical issues to be addressed include identification of significant endpoints, sample size determination, power considerations, stratification, randomization and design.

The design of this study is viewed primarily within the framework of a Single Arm Phase II trial. However, as the purpose is also to investigate possible differences between GM-CSF doses as adjuvants, it incorporates design elements characteristic of a Multiple Arm Phase II or a randomized Phase III trial. Statistical methods that are appropriate to both single and double arm designs are described.

Patients receive combination chemotherapy to best response followed by Id-KLH combined with GM-CSF. Several outcome measures (endpoints) are evaluated in order to meet the objectives of this study. They include:

1) The clinical complete response rate (in contradistinction to the molecular or PCR response rate) of all patients to ProMACE—a percentage indicated by the disappearance of all clinical and laboratory signs and symptoms of active disease, excluding PCR, for a minimum of one month.

2) The Polymerase Chain Reaction (PCR) response rate (molecular-complete response rate)—the percentage of patients who, having achieved a clinical complete response still remain PCR (+) at the end of chemotherapy, and who then become PCR (−) with the administration of immunotherapy.

3) Disease Free Survival Rate—computed by Kaplan-Meier curves and related survival measures.

The PCR response rate is taken as the primary outcome variable of interest to ascertain the following: (1) to determine the ability of Id immunization to eradicate bcl-2 positive tumor cells from the bone marrow and; (2) to identify the more biologically active of the two doses of GM-CSF. In this endeavor, the plan is to accrue 42 patients. It is estimated that approximately 38 (90%) of these patients will be bcl-2 (+) and thus evaluable for molecular response rate. The other four patients may still be evaluable for a molecular response rate based on Ig gene amplification using allele-specific (CDR3) primers by PCR. From previous experience with ProMACE-based regimens, it is estimated that 32 (85%) of these patients will achieve either a complete response (complete clinical response, CCR) or a partial response in which a >90% partial remission has been obtained (high partial response, HPR). The accuracy of these estimates are of some interest. For the 42 (90%) patients anticipated to be bcl-2 (+), lower and upper 95% confidence intervals are 77% and 96%. For the 38 (85%) patients anticipated to achieve either a complete clinical response or a high partial response, the lower and upper confidence intervals are 70% and 93%.

Patients are stratified on the basis of their ProMACE treatment performance as either a complete clinical responder (CCR) or as a high partial responder (HPR). It is not known exactly what percentage of these 32 patients will be CCRs and what percentage will be HPR'S. Hence a block size of four (4) is used in the randomization scheme to assure a reasonably balanced allocation to each dose group. Given the patients allocation stratum, he (she) is randomly assigned to one of the adjuvant groups according to the envelope method (29). Specifically, a block of four assignments is placed in four separate envelopes. The block of four is placed in one of the two allocation strata, say CCR. Another block of four is placed in the other allocation strata, say CCR. Another block of four is placed in the other allocation stratum, HPR. When a patient is to be randomized, a call is made to the biostatistician who, after being informed of the patients status as either a CCR or an HPR, randomly draws an envelope from the appropriate stratum to determine the patients dose group assignment. After the four envelopes pertinent to a particular stratum have been exhausted, the next batch of four envelopes is made available for use. This procedure is continued until a total of 32 patients have been assigned to the two dose groups.

For example, it is estimated that 50–80 percent of pathological complete responders will fall into the CCR category. If 75% of 32, or 24 patients were to be classified as CCRs, six blocks of four envelopes would be required to randomly assign 12 patients to cohort 1 and 12 patients to cohort 2. A similar procedure would occur concurrently with the 8 patients classified as HPRs. Two blocks of four envelopes would be required to randomly assign 4 patients to cohort 1 and 4 patients to cohort 2. At no time could the number of patients in each dose group differ by more than four.

At the time of data analysis, approximately 16 subjects will comprise each dose group and a test for the difference in PCR response rates between the two groups will be conducted. By hypothesis, neither dose group is predicted to have a higher PCR response rate than the other; hence, a two-tailed test is appropriate. Power calculations show that, with the groups limited to 16 patients, the difference in PCR response rates will have to be large (30, 31). For example, to detect a difference at the $\alpha=0.05$ level of significance with power (1-$\beta$) equal to 80%, the response rates must differ by 55%; with power equal to 50%, the response rates must differ by 50%. In the event that no significant difference is detected, the subjects will be pooled and the overall PCR response rate will be assessed. With a total of 32 CCRs and HPRs treated with vaccine, the width of a two-tailed 95% confidence interval for a response rate of 50% will not exceed 17 percentage points. If the actual response rate is higher or lower than 50%, the confidence interval will be smaller.

Disease-free survival distributions are estimated by the Kaplan-Meier (product-limit) method and dose groups are compared using the log rank test. If no dose group differences are detected, the subjects from both groups are pooled and the Kaplan-Meier estimate of the survivorship function and related functions are evaluated. If suggested by the data analysis, parametric distributions (e.g., Weibull, log-normal) are fit as well (32, 33).

15.1 Research ethics: Subjects from [both genders and] all racial/ethnic groups are eligible for this study if they meet the eligibility criteria outlined in Section 2.0. To date, there is not information that suggests that differences in grud metabolism or disease response would be expected in one group compared to another. Efforts are made to extend accrual to a representative population, but in this preliminary study, a balance must be struck between patient safety considerations and limitations on the number of individuals exposed to potentially toxic and/or ineffective treatments on the one hand and the need to explore gender and ethnic aspects of clinical research on the other hand. If differences in outcome that correlate to gender or to ethnic identity are noted, accrual can be expanded or a follow-up study can be written to investigate those differences more fully. Alternatively, substantial scientific data exist demonstrating that there is no significant difference in outcome between genders or various ethnic groups.

16.0 Records to be Kept and Quality Assurance 16.1 Consent form: The original signed informed consent documents will be kept with the patient's other study documentation (e.g., the research chart). A copy of the informed consent document will also be retained by the Data Management Section.

16.2 The Clinical Coordinator, Data Management Section, will ascertain the dates of the IRB approvals before registering the first patient.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Stevenson G T, Stevenson F K. Antibody to molecularly defined antigen confined to a tumor cell surface. *Nature*, 1975, 254:714–6.

2. Stevenson G T, Elliott E V, Stevenson F K. Idiotypic determinants on the surface Immunoglobulin of neoplastic lymphocytes: a therapeutic target. *Fed Proc*, 1977, 36:2268–71.
3. Miller P A, Maloney D G, Warnke R, Levy R. Treatment of B cell lymphoma with monoclonal anti-idiotype antibody. *N Engl J Med*, 1982, 306;517–22.
4. Sirisinha S, Eisen H N. Autoimmune-like antibodies to the ligand-binding sites of myeloma proteins. *Proc Natl Acad Sci USA*, 1971, 68:3130–5.
5. Jorgensen T, Gaudemack G, Hannestad K. Immunization with the light chain and the VL domain of the isologous myeloma protein 315 inhibits growth of mouse plasmacytoma MOPC-315. *Scand J Immunol*, 1980,11:29–35.
6. Daley M J, Gebel H M, Lynch R G. Idiotype-specific transplantation resistance to MOPC-315: Abrogation by post-immunization thymectomy. *J Immunol*, 1978, 120:1620–4.
7. Bridges S H. Participation of the humoral immune system in the myeloma-specific transplantation resistance. *J Immunol*, 1978, 121:479–83.
8. Freedman P M, Autry J R, Tokuda S, Williams R C, Jr. Tumor immunity induced by preimmunization with BALB/c mouse myeloma protein. *J Natl Cancer Inst.* 1976, 56:735–740.
9. Sugai S, Palmer D W, Taial N. Witz I P. Protective and cellular immune responses to idiotypic determinants on cells from a spontaneous lymphoma of NZB/NZWF1 mice. *J Exp Med*, 1974,140:1547–58.
10. Stevenson F K, Gordon J. Immunization with idiotypic immunoglobulin protects against development of B lymphocytic leukemia, but emerging tumor cells can evade antibody attack by modulation. *J Immunol*, 1983, 130:970–973.
11. George A J T, Tutt A L, Stevenson F K. Anti-idiotypic mechanisms involved in the suppression of a mouse B cell lymphoma, BCL. *J Immunol*, 1987,138:628–634.
12. Kaminski M S, Kitamura K, Maloney D G, Levy R. Idiotype vaccination against murine B cell lymphoma. Inhibition of tumor immunity by free idiotype protein. *J Immunol*, 1987,138:1289–1296.
13. Kwak L W, Campbell M J, Zelonetz A D, Levy R. Combined syngeneic bone marrow transplantation and immunotherapy of a murine B-cell lymphoma: Active immunization with tumor-derived idiotypic immunoglobulin. *Blood*, 1990, 76:2411–2417.
14. Campbell M J, Esserman L. Byars N E, Allison A C, Levy R. Development of a new therapeutic approach to B cell malignancy: the induction of immunity by the host against cell surface receptor on the tumor. *Int Rev immunol*, 1989, 4:251–70.
15. Kwak L W, Campbell M J, Czervwinski D K, Hart S, Miller R A, Levy R. Induction of immune responses in patients with B cell lymphoma against the surface immunoglobulin idiotype expressed by their tumors. *N Engl J Med*, 1992, 327:1209–1215.
16. Longo D L- Young R C, DeVita V T. What is so good about the "good prognosis" lymphoma? In Williams C G, Whithouse J M A (eds): *Recent Advances in Clinical Oncol* Edinburgh, Churchill-Livingstone, pp. 223–231, 1982.
17. Portlock C S. "Good risk" non-Hodgkin's lymphomas. Approaches to management. *Sem Hematol*, 1980. 20:25–34.
18. Portlock C S, Rosenberg S A. No initial therapy for stage III and IV non-Hodgldn's lymphomas of favorable histologic types. *Ann Intern Med*, 1979, 90:10–13.
19. Homing S J, Rosenberg S A. The natural history of initially untreated low-grade non-Hodgkin's lymphomas. *N Engl J Med*, 1984, 311:147–51.
20. Orentas R J. Hildreth J E K, Obah E, Polydefkis M. Smith G E, Clements M L, Siliciano R F. Induction of CD4+ human cytolytic T cells specific for HIV-infected cells by a gp160 subunit vaccine. *Science*, 1990, 248:1234–6.
21. Schwartzentruber D J, Stetter-Stevenson M. Rosenberg S A, Topalian S L. Tumor infiltrating lymphocytes derived from select B-cell lymphomas secrete granulocyte-macrophage colony-stimulating factor and tumor necrosis factor-α in response to autologous tumor stimulation. *Blood*, 1993, 82:1204–11.
22. Schlegal P G. Schmidt-Wolf G, Schmidt-Wolf G H, Kwak L W, Blume K G, Chao N J. Lymphokine-activated killer cell activity against autologous lymphoma cells following bone marrow transplantation. *Cancer Res.* 1993, in press.
23. Gribben J G, Freedman A S, Neuberg D, Roy D C, Blake K W, Woo S D, Grossard M L, Rabinow S N, Coral F, Freeman G J, Ritz J, Nadler L M. Immunologic purging of marrow assessed by PCR before autologous bone marrow transplantation for B-cell lymphoma. *N Engl J Med*, 1991, 325:1525.
24. Morton D L, et al. Annals New York Academy of Sciences. Polyvalent melanoma vaccine improves survival of patients with metastatic melanoma. 120; 1993.
25. Bystryn J C. Annals New York Academy of Sciences. Immunogenicity and clinical activity of a polyvalent melanoma antigen vaccine prepared from shed antigens. 190; 1993.
26. Wallack M K. Annals NewYork Academy of Sciences. Clinical trials withVMo for melanoma. 178;1993.
27. Hershey P. Annals New York Academy of Sciences. Evaluation of vaccinia viral lysates as therapeutic vaccines in the treatment of melanoma. 167; 1993.
28. Mitchell M S, et al. Annals New York Academy of Sciences. Active specific immunotherapy of melanoma with allogeneic cell lysates. 153;1993.
29. Lesser M L. Design and implementation of clinical trials. In: Statistics in Medical Research—Methods and Issues with Applications in Cancer Research. Ed: Mike V and Stanley K F, New York, Wiley. 1982.
30. Gehan E A, Schneiderman M A: Experimental Design of Clinical Trials, in Holland J F and Frei E, Ill, eds. *Cancer Medicine* (2nd ed.). Lea and Febinger, Philadelphia, 531–553,1982.
31. Gail M, Gart J J: The Determination of Sample Sizes for Use with the Exact Conditional Test in 2×2 Comparative Trials. *Biometrics*, 29, 441–448, 1973.
32. Lee E T: Statistical Methods for Survival Data Analysis, Wiley, New York, 1992.
33. Kalbfleisch J D, Prentice R L: The Statistical Analysis of Failure Time Data, New York, Wiley, 1980.
34. Current protocols in immunology. J. E. Coligan, A. D. Kruisbeek. D. H. Margulies, E. M. Sgevach and W. Strober, Eds. (J. Wiley & Sons, Inc., New York, 1994), p. 3–4.1.
35. B. A. Ben, et al, *J. Immunol.* 158, 5927 (1997).
36. Bergmanm Y., J. Haimovich, Characterization of a carcinogen-induced murine B lymphocyte cell line of C3H/eb origin. *J. Immunol.* (1977). 7: 413
37. Kwak et al. 1991. Transfer of specific immunity to B-cell lymphoma with syngeneic bone marrow in mice. *Blood* 78:2768–2772.
38. E-Blasi, et al. *Nature* 318, 667 (1985).

39. R. Bonecchi, et al. *J. Exp. Med.* 187,129 (1998).
40. J. Buchner, I. Pastan, U. Binkmann, *Anal. Biochem.* 205, 263 (1992).
41. E. C. Butcher, *Cell* 67,1033 (1991).
42. M. J. Campbell, et al, *J. Immunol.* 139. 2825 (1987).
43. M. J. Campbell, L. Esserman. N. E. Byars, A. C. Alison, R. Levy, Idiotype vaccination against murine B cell lymphoma. Humoral and cellular requirements for the full expression of antitumor immunity. *J. Immunol.* (1998) 145(3):1029–1036.
44. H. L. Davis et al. *Vaccine* 15, 849 (1997).
45. D. Dilloo et al. *Nature Medicine* 2, 1090 (1998).
46. R. J. Dyke, H. McBride, A. J. George, T. J. Hamblin, F. K. Stevenson, *Cell Immunol* 132, 70 (1991).
47. W. J. Fairbrother, N-J-Skelton, Chemoattractant ligands and their receptors., R. Horuk, Ed. (CRC, Boca Raton, NY, London, Tokyo, 1996), p. 55.
48. A. Haelens, et al. *Immunobiology* 195, 499 (1996).
49. I. Hakim, S. Levy, R. Levy, *J.Immunol* 157, 5503 (1 996).
50. J. S. Huston, H. Oppermann, inventors, Targeted multifunctional proteins. USA. wo88 09344. (198).
51. K. J. Kim, L. C. Kanellopoulos, R. M. Merwin, D. H. Sachs, R. Asofsky, *J. Immunol.* 122, 549 (1979).
52. L. W. Kwak et al. *N. Engl. J. Med.* 327, 1209 (1992).
53. L. W. Kwak, et al. Lancet 345, 1016 (1995).
54. L. W. Kwak, H. A. Young, R. W. Pennington, S. D. Weeks, *Proc. Natl. Acad. Sci. U.S.A.* 93, 10972 (1996).
55. M. Loetscher et al., *J Exp. Med.* 184, 963 (1995).
56. P. Loetscher, M. Seitz, L. I. Clark, M. Baggiolini, B. Moser, *J. Immunol.* 156, 322 (1996).
57. A. D. Luster, P. Leder, *J. Exp. Med.* 178, 1057 (1993).
58. A. D. Luster, *N. Eng. J. Med*, 338, 436 (1998).
59. B. J, Rollins, *Blood* 90, 909 (1997).
60. Y. Sato et al. *Science* 273, 352 (1996).
61. J. M. Schroder, *J. Invest. Dematol.* 105,20S (1995).
62. R. Solary et al, *J. Biol. Chem.* 272, 9617 (1997).
63. M. B. Spellerberg et al., *J. Immunol.* 159, 1885 (1997).
64. F. K. Stevenson et al., *Immunol. Rev.* 146. 211 (1996).
65. R. M. Strieter et al., *J. Biol. Chem.* 270, 27348 (1995).
66. C. J. Talpas, D. A. Walz, L. Lee, *Biochim. Biophys. Acta* 1078, 208 (1991).
67. Y. Tanaka, D. H. Adams, S. Shaw, *Immunol Today* 14, 111 (1993)
68. G. J. Weiner, H. M. Liu, J. E, Wooldridge, C. E. Dahle, A. M. Krieg, *Proc. Nat. Acad. Sci. U.S.A.* 94, 10833 (1997)
69. C. Winkler, et al, *Science* 279, 389 (1998).
70. M, Yokoyama, D. F. Hassett, J. Zhang, J. L. Whitton. *Vaccine* 15,. 553 (1997).
71. Finn et al., 1995. *Immunological Reviews* 145:61–88; "Partially purified tumor antigen vaccines" (section 23.4), In: *Biologic Therapy of Cancer: Principles and Practice*, 2nd ed. Edited by DeVita et al., J.B. Lippincott Co., 1995).
72. Old, L. J. "Cancer immunology: The search for specificity," GHA Clowes Memorial Lecture. *Cancer Res.* 41:361–375, 1981.
73. Livingston, P. In: *Biologic Therapy of Cancer: Principles and Practice*, 2nd ed. Edited by DeVita et al., J.B. Lippincott Co., 1995.
74. Harlow & Lane, *Antibodies, A Laboratory Manual*, Cold Spring Harbor Laboratory, Cold Spring Harbor, New York, 1988.
75. Baggioni, M., et al., 1994. IL-8 and related chemotactic cytokines-CXC and CC chemokines. *Adv. Immunol.* 55:97–179.
76. Garcia-Zepeda, E. A., et al., 1996. Human monocyte chemoattractant protein (MCP)-4 is a novel chemokine with activities on monocytes, eosinophils and basophils induced in allergic and nonallergic inflammation that signals through the CC chemokine receptors (CCR)-2 and -3. *J Immunol.* 157:5613–5626.
77. Clark-Lewis et al., 1991. Structure-activity relationship of IL-8 determined using chemically synthesized analogs: critical role of $NH_2$-terminal residues and evidence for uncoupling neutrophil chemotaxis, exocytosis and receptor binding. *J. Biol. Chem.* 266:128–134.
78. Weber, M., et al., 1996. Deletion of the $NH_2$-terminal residue converts MCP-1 from an activator of basophil mediator release to an eosinophil chemoattractant. *J. Exp. Med.* 183:681–685.
79. *The Oncogene Handbook*, T. Curran, E. P. Reddy, and A. Salka (ed.), Elsevier Science Publishers, The Netherlands (1988).
80. Dayhoff et al., in *Atlas of Protein Sequence and Structure* 1978, Nat'l Biomed. Res. Found., Washington, D.C.
81. Sambrook et al., *Molecular Cloning: A Laboratory Manual*, 2d. edition, Cold Spring Harbor Laboratory, Cold Spring Harbor, N.Y., 1989.
82. Brake et al., "Alpha-factor-directed synthesis and secretion of mature foreign proteins in *Saccharomyces cerevisiae*," PNAS 82:4642–4646, 1984.
83. U.S. Pat. No. 4,704,362.
84. *Remington's Pharmaceutical Sciences* (Martin, E. W., ed., latest edition, Mack Publishing Co., Easton, Pa.).
85. Harlow and Lane, *Antibodies, A Laboratory Manual*, Cold Spring Harbor Laboratory, Cold Spring Harbor, N.Y., 1988).
86. "Immunologic Studies in Humans," *Current Protocols in Immunology*, J. E. Coligan et al., eds. John Wiley & Sons, New York, 1991.
87. Yamamoto et al., "Highly sensitive qualitative and quantitative detection of reverse transcriptase activity: optimization, validation and comparative analysis of other detection systems." *J. Virol. Meth.* 61:135–143, 1996.
88. Kageyama, S. et al., "An improved method for the detection of HIV antigen in the blood of carriers," *J. Virol. Meth.* 22:125–131, 1988.
89. Ho, D. D. et al., "Quantitation of human immunodeficiency virus type 1 in the blood of infected persons," *N. Eng. J. Med.* 321:1621–1625, 1988.
90. Piatak, M. et al., "High levels of HIV-1 in plasma during all stages of infection determined by competitive PCR," *Science* 259:1749–1754, 1993.
91. Mulder, J. et al., "Rapid and simple PCR assay for quantitation of human immunodeficiency virus type 1 RNA in plasma: Application to acute retroviral infection," *J. Clin. Microbiol.* 32:292–300, 1994.
92. Arnon, R. (Ed.) *Synthetic Vaccines I*:83–92, CRC Press, Inc., Boca Raton, Fla., 1987.
93. Willis et al., *Gene* 128:79–83, 1993.
94. Jellis et al., *Gene* 137:63–68, 1993.
95. Barbas et al., PNAS 89:4457–4461, 1992.
96. Pastan et al. "A retrovirus carrying an MDR1 cDNA confers multidrug resistance and polarized expression of P-glycoprotein in MDCK cells." *Proc. Nat. Acad. Sci.* 85:4486 (1988).
97. Miller et al. "Redesign of retrovirus packaging cell lines to avoid recombination leading to helper virus production." *Mol. Cell Biol.* 6:2895 (1986).
98. Mitani et al. "Transduction of human bone marrow by adenoviral vector." *Human Gene Therapy* 5:941–948 (1994)).
99. Goodman et al. "Recombinant adeno-associated virus-mediated gene transfer into hematopoietic progenitor cells." *Blood* 84:1492–1500 (1994))

100. Naidini et al. "In vivo gene delivery and stable transduction of nondividing cells by a lentiviral vector." *Science* 272:263–267 (1996))
101. Agrawal et al. "Cell-cycle kinetics and VSV-G pseudotyped retrovirus mediated gene transfer in blood-derived CD34+ cells." *Exp. Hematol.* 24:738–747 (1996)).
102. Schwarzenberger et al. "Targeted gene transfer to human hematopoietic progenitor cell lines through the c-kit receptor." *Blood* 87:472–478 (1996)).
103. Fields, et al. (1990) Virology, Raven Press, New York).
104. Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985–1001.
105. Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229–242.
106. Bergman, Y. & Haimovich, J. Characterization of a carcinogen-induced murine B lymphocyte cell line of C3H/eB origin. *Eur. J. Immunol.* 7, 413–417, 1977.
107. Kim, K. J., Kanelloupolos-Langevin, C. Merwin, R. M., Sachs, D. H. & Asofsky, R. Establishment and characterization of BALB/c lymphoma lines with B cell properties. *J. Immunol.* 122, 549–554, 1979.
108. Huston, J. S., Levinson, D., Mudgett-Hunter, M., Tai, M. S., Novotny, J., Margolies, M. N., Ridge, R. J., Bruccoleri, R. E., Haber, E., Crea R., & Oppermann, H. Protein engineering of antibody binding sites: Recovery of specific activity in an anti-digoxin single-chain Fv analogue produced in *Escherichia coli*. *Proc. Natl Acad. Sci. USA* 85, 5879–5883, 1988.
109. Blasi, E., Matthieson, B. J. & Varesio, L. Selective immortalization of murine macrophages from fresh bone marrow by a raf/myc recombinant murine retrovirus. *Nature* 318, 667–670, 1985.
110. Buchner, J., Pastan, I. & Brinkmann, U. A method for increasing the yield of properly folded recombinant fusion proteins: Single-chain immunotoxins from renaturation of bacterial inclusion bodies. *Analytical Biochem.* 205, 263–270, 1992.
111. Kwak, L. W., Young, H. A., Pennington, R. W., & Weeks, S. W. Vaccination with syngeneic, lymphoma-derived immunoglobulin idiotype combined with granulocyte/macrophage colony-stimulating factor primes mice for a protective T-cell response. *Proc. Natl. Acad. Sci. USA* 93, 10972–10977, 1996.
112. Falk, W., Goodwin, R. H., & Leonard, E. J. A 48-well micro chemotaxis assembly for rapid and accurate measurement of leukocyte migration. *J. Immunol. Methods* 33, 239–247, 1980.
113. Solari, R., Offord, R. E., Remy, S., Aubry, J. P., Wells, T. N. C., Whitehorn, E., Oung, T., & Proudfoot, A. E. I. Receptor-mediated endocytosis of CC-chemokines. *J. Biol. Chem.* 272, 9617–9620, 1997.
114. Feltquate, D. M., Heaney, S., Webster, R. G., & Robinson, H. L. Different T helper cell types and antibody isotypes generated by saline and gene gun DNA immunization. *J. Immunol.* 158, 2278–2284, 1997.
115. Kwak, L. W., Campbell, M. J., Czerwinski, D. K., Hart, S., Miller, R. A., & Levy, R. Induction of immune responses in patients with B-cell lymphoma against the surface-immunoglobulin idiotype expressed by their tumors. *N. Engl. J Med.* 327, 1209–1215, 1992.
116. Kaminski, M. S., Kitamura, K., Maloney, D. G. & Levy, R. Idiotype vaccination against murine B cell lymphoma, inhibition of tumor immunity by free idiotype protein. *J. Immunol.* 138, 1289–1296, 1987.
117. Stevenson, G. T. & Stevenson, F. K. Antibody to a molecularly-defined antigen confined to a tumor cell surface. *Nature* 254, 714–716, 1975.
118. Xu, L. L., McVicar, D. W., Ben-Baruch, A., Kuhns, D. B., Johnston, J., Oppenheim, J. J. & Wang, J. M. Monocyte chemotactic protein-3 (MCP3) interacts with multiple leukocyte receptors: binding and signaling of MCP3 through shared as well as unique receptors on monocytes and neutrophils. *Eur. J. Immunol.* 25, 2612–2617, 1995.
119. Gong, J. H., Uguccioni, M., Dewald, B., Baggiolini, M. & Clark-Lewis, I. RANTES and MCP-3 antagonists bind multiple chemokine receptors. *J. Biol. Chem.* 271, 10521–10527, 1996.
120. Clore et al. 1990.
121. Lodi et al. 1994.
122. Skelton et al. 1995.
123. Fairbrother et al. 1994.
124. Horuk R, 1996.
125. Bergman and Haimovich, 1977. Characterization of a carcinogen-induced murine B lymphocyte cell line of C3H/eB origin. *Eur. J. Immunol.* 7:413–417.
126. Emini et al. 1992. Prevention of HIV-1 infection in chimpanzees by gp120 V3 domain-specific monoclonal antibody. *Nature*, 355:728–730.
127. Yarchoan et al. 1990. The National Cancer Institute Phase I Study of 2',3'-Dideoxyinosine Administration in Adults with AIDS or AIDS-related Complex: Analysis of Activity and Toxicity Profiles. *Reviews of Infectious Diseases*, 12(5):S522–S533.

What is claimed is:

1. A fusion polypeptide comprising the amino acid sequence of SEQ ID NO:2.

2. A composition comprising the fusion polypeptide of claim 1 in a pharmaceutically acceptable carrier.

3. A method of producing an immune response in a subject, wherein the immune response is an immune response against human Muc-1, comprising administering to the subject the composition of claim 2.

4. A method of inhibiting growth of tumor cells that express human Muc-1 in a subject comprising administering to the subject the composition of claim 2.

* * * * *